(12) United States Patent
Lagrange

(10) Patent No.: US 7,425,221 B2
(45) Date of Patent: Sep. 16, 2008

(54) COMPOSITION COMPRISING AT LEAST ONE SUBSTITUTED DERIVATIVE OF CARBOCYANINE, METHOD FOR TREATING KERATIN FIBERS USING IT, DEVICE AND USE

(75) Inventor: Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 332 days.

(21) Appl. No.: 11/223,149

(22) Filed: Sep. 12, 2005

(65) Prior Publication Data
US 2006/0195990 A1 Sep. 7, 2006

Related U.S. Application Data

(60) Provisional application No. 60/616,352, filed on Oct. 7, 2004.

(30) Foreign Application Priority Data
Sep. 13, 2004 (FR) .................. 04 09693

(51) Int. Cl.
*A61Q 5/10* (2006.01)
*C07D 277/08* (2006.01)
(52) U.S. Cl. ............ 8/405; 8/406; 8/407; 8/426; 8/431; 8/565; 8/568; 8/570; 8/575; 8/576; 548/146; 548/215
(58) Field of Classification Search .......... 8/405, 8/406, 407, 409, 426, 431, 565, 568, 570, 8/575, 576; 548/146, 215
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 2,798,053 A | 7/1957 | Brown | |
| 2,923,692 A | 2/1960 | Ackerman et al. | |
| 3,666,464 A | 5/1972 | Keller et al. | |
| 3,679,427 A | 7/1972 | Lincoln et al. | |
| 3,821,233 A | 6/1974 | Lincoln et al. | |
| 3,864,644 A | 2/1975 | Lincoln et al. | |
| 3,904,637 A | 9/1975 | Lincoln et al. | |
| 3,915,921 A | 10/1975 | Schlatzer, Jr. | |
| 4,011,086 A | 3/1977 | Simson | |
| 4,237,243 A | 12/1980 | Quack et al. | |
| 4,309,551 A | 1/1982 | Schonberger et al. | |
| 4,509,949 A | 4/1985 | Huang et al. | |
| 4,823,985 A | 4/1989 | Grollier et al. | |
| 5,089,578 A | 2/1992 | Valint et al. | |
| 5,474,578 A | 12/1995 | Chan et al. | |
| 5,708,151 A | 1/1998 | Möckli | |
| 5,733,343 A | 3/1998 | Mockli | |
| 5,734,058 A | 3/1998 | Lee | |
| 5,792,221 A | 8/1998 | Lagrange et al. | |
| 5,830,446 A | 11/1998 | Berthiaume et al. | |
| 5,914,373 A | 6/1999 | Glancy et al. | |
| 5,981,747 A | 11/1999 | Mujumdar et al. | |
| 5,986,093 A | 11/1999 | Mujumdar et al. | |
| 6,120,780 A | 9/2000 | Dupuis et al. | |
| 6,133,445 A | 10/2000 | Waggoner et al. | |
| 6,822,039 B1 | 11/2004 | Monfreux-Gaillard et al. | |
| 2003/0124079 A1 | 7/2003 | Mougin et al. | |
| 2003/0188390 A1 | 10/2003 | Matsunaga | |
| 2003/0224391 A1 | 12/2003 | Waggoner et al. | |
| 2004/0078906 A1 | 4/2004 | Plos et al. | |
| 2004/0205901 A1 | 10/2004 | Cottard et al. | |
| 2005/0028301 A1 | 2/2005 | Pastore | |

FOREIGN PATENT DOCUMENTS

| | | |
|---|---|---|
| DE | 38 29 870 | 4/1989 |
| DE | 197 32 016 | 1/1999 |
| EP | 0 121 326 | 10/1984 |
| EP | 0 173 109 B1 | 10/1989 |
| EP | 0 395 282 B1 | 3/1995 |
| EP | 0 503 853 B1 | 5/1996 |
| EP | 0 747 448 | 12/1996 |
| EP | 0 750 899 A2 | 1/1997 |
| EP | 0 815 828 B1 | 2/1999 |
| EP | 1 166 753 | 1/2001 |
| EP | 1 166 757 | 1/2001 |
| EP | 1 133 978 | 9/2001 |
| EP | 1 170 001 | 1/2002 |
| EP | 0 714 954 B1 | 9/2002 |

(Continued)

OTHER PUBLICATIONS

Cyanine Dyes from Dihydrooxazino-and Dihydrothiazino-Bennzthiazolium Salts, pp. 562-570, Mar. 1965.*

(Continued)

*Primary Examiner*—Eisa B Elhilo
(74) *Attorney, Agent, or Firm*—Finnegan, Henderson, Farabow, Garrett & Dunner, LLP

(57) ABSTRACT

The invention relates to a composition comprising, in a cosmetically acceptable medium, at least one particular direct dye.

The invention further relates to a method for treating keratin fibers, in particular human keratin fibers, using the above-mentioned composition, and a device comprising it.

Finally, its subject is the use of the composition according to the invention as agent for lightening and/or as agent for dyeing said fibers.

37 Claims, No Drawings

FOREIGN PATENT DOCUMENTS

| | | |
|---|---|---|
| EP | 1 352 632 | 10/2003 |
| EP | 1 415 643 A1 | 5/2004 |
| EP | 1634575 | 3/2006 |
| EP | 1652553 | 5/2006 |
| EP | 1652554 | 5/2006 |
| FR | 1 573 139 | 7/1969 |
| FR | 2 416 723 A1 | 9/1979 |
| FR | 2 586 913 A1 | 3/1987 |
| FR | 2 692 572 A1 | 12/1993 |
| FR | 2 741 261 | 5/1997 |
| FR | 2 811 993 A1 | 1/2002 |
| FR | 2 820 032 A1 | 8/2002 |
| FR | 2 875 130 | 3/2006 |
| FR | 2 875 131 | 3/2006 |
| FR | 2 875 132 | 3/2006 |
| GB | 1 529 807 | 10/1978 |
| JP | 80012407 | 4/1980 |
| JP | 2006-083170 | 3/2006 |
| WO | WO 95/01772 A1 | 1/1995 |
| WO | WO 95/15144 A1 | 6/1995 |
| WO | WO 97/17471 | 5/1997 |
| WO | WO 99/13849 | 3/1999 |
| WO | WO 99/31181 | 6/1999 |
| WO | WO 00/31154 A1 | 6/2000 |
| WO | WO 00/68282 A1 | 11/2000 |
| WO | WO 03/028685 A1 | 4/2003 |

OTHER PUBLICATIONS

STIC Search Report dated Jun. 5, 2007.*

Babichev, F.S. et al., "Cyanine Dyes from Dihydrooxazino- and Dihydrothiazino-Bennzthiazolium Salts," translated from *Zhurnal Organicheskoi Khimii*, vol. 1, No. 3, pp. 562-570, Mar. 1965.

Babichev, F.S. et al., Styryl Dyes, Mero- and Rhodacyanine from 2,3-Polymethylenebenzothiazolium Salts, translated from *Zhurnal Obshehei Khimii*, vol. 34, No. 7, pp. 2433-2440, Jul. 1964.

Eaves, J. et al., "An MNDO study of dipyridopyrazinium and relation cations: instability of certain fused heteroaromic dications with two bridgehead nitrogens" *Can. J. Chem. 64*:1711-13 (1986).

Fonnum, G. et al., "Associative thickeners. Part 1: Synthesis, rheology and aggregation behavior," *Colloid Polym. Sci. 271*(4):380-89 (1993).

Morishima, Y., "Self-assembling amphiphilic polyelectrolytes and their nanostructures," *Chinese J. Polymer Science 18*(40):323-36 (2000).

Noda, T. et al., "Micelle formation of random copolymers of sodium 2-(acrylamido)-2-methylpropanesulfonate and a nonionic surfactant macromonomer in water as studied by fluorescence and dynamic light scattering," *Macromolecules 33*(10):3694-3704 (2000).

Noda, T. et al., "Solution properties of micelle networks formed by nonionic surfactant moieties covalently bound to a polyelectrolyte: salt effects on rheological behavior," *Langmuir 16*(12):5324-32 (2000).

Noda, T. et al., "Stimuli responsive amphiphilic copolymers of sodium 2-(acrylamido)-2-methylpropanesulfonate and associative macromonomers," *Polymer Preprints 40*(2):220-221 (1999).

Tredwell, C. et al., "Picosecond time resolved fluorescence lifetimes of the polymethine and related dyes," *Chem. Phys. 43*(3):307-16 (1979).

Zviak, C., *The Science of Hair Care*, Masson, Paris, pp. 215, 278 (1988).

Yarmolyuk, S.M. "Interaction of Cyanine Dyes with Nucleic Acids: Investigation of Cyanine Dyes as Fluorescent Probes for the Nucleic Acids Detection," *Biopolimeriy I Kletka*, 15 (4):328-336 (1999).

Romanov, N.N. et al., "Cyanine Dyes with three cyclic groupings of dihydrooxazino-and dihydrothiazinobenzothiasolium salts," Dopovidi Akadermii Nauk Ukrains'Koi RSR, Seriya B: Geologichni, Khimichni Ta Biologichni Nauki, (7), 622-4 (1976).

Porter, M.R. "Handbook of Surfactants," Blackie & Son, Ltd., pp. 116-178 (1991).

Co--pending U.S. Appl. No. 11/223,962, filed Sep. 13, 2005.

Co-pending U.S. Appl. No. 11/223,961 filed Sep. 12, 2005.

French Search Report for French Appln. No. 04/09694, related to co-pending U.S. Appl. No. 11/223,962, (2005).

French Search Report for French Appln. No. 04/09693, related to present U.S. Appl. No. 11/223,149. (2005).

French Search Report for French Appln. No. 04/09695, related to co-pending U.S. Appl. No. 11/223,961, 2005.

English language Derwent Abstract for JP 80012407. (1980).

Office Action in co-pending U.S. Appl. No. 11/223,961 dated Oct. 23, 2007 (Ex. Elhilo).

Office Action in co-pending U.S. Appl. No. 11/223,962 dated Oct. 23, 2007 (Ex. Elhilo).

Daltrozzo E. et al., "Tautomerism of Qinoline Red dyes," STN Database accession No. 1966:104990.

Notice of Allowance and Fees Due dated Apr. 18, 2008, co-pending U.S. Appl. No. 11/223,962.

* cited by examiner

COMPOSITION COMPRISING AT LEAST ONE SUBSTITUTED DERIVATIVE OF CARBOCYANINE, METHOD FOR TREATING KERATIN FIBERS USING IT, DEVICE AND USE

FIELD OF THE INVENTION

The invention relates to a composition comprising, in a cosmetically acceptable medium, at least one particular direct dye which is a substituted derivative of carbocyanine. Likewise, its subject is a method for treating keratin fibers using this composition, and a device comprising it. Finally, its subject is the use of the composition according to the invention as lightening agent and/or as dyeing agent for said fibers.

The present invention relates to the field of dyeing of keratin fibers and more particularly of hair dyeing.

BACKGROUND OF THE INVENTION

There are essentially two types of dyeing.

The first is the so-called semipermanent dyeing or direct dyeing, which involves dyes capable of giving the natural coloration of the hair a more or less marked modification.

The dyes used are colored and coloring substances which exhibit a degree of affinity with the keratin fiber.

It should be noted that this type of coloration fades after several washings, which may represent a disadvantage.

In the case where it is desired to obtain a coloration which is lighter than the original color of the fibers, it is necessary to use with the direct dyes at least one oxidizing agent, under alkaline pH conditions.

However, these conditions for use are not without consequences on the properties of the fibers treated. Indeed, over time, the fibers are more or less degraded and tend to become rough, dull, brittle and difficult to style.

The second is permanent dyeing or oxidation dyeing. The latter is carried out with oxidation dye precursors which are colorless or faintly colored compounds comprising at least one oxidation base optionally combined with one or more couplers. Once mixed with oxidizing products, at the time of use, the precursors can give rise, through a process of oxidative condensation, to colored and coloring compounds.

Given the necessary presence of an oxidizing agent in this type of dyeing, the disadvantages mentioned above are also observed in this case.

It has recently been observed that compositions comprising at least one fluorescent compound represented an advantageous alternative to conventional methods using an oxidizing agent. Thus, for dark hair, more particularly whose tone height is less than or equal to 6 (dark blond), preferably less than or equal to 4 (chestnut brown), it was possible to observe that there were zones for which the curve of reflectance as a function of wavelength (between 500 and 700 nm) for hair treated with the composition comprising the fluorescent compound was superior to the curve corresponding to untreated hair. Consequently, the hair appears lightened, without the need to use an oxidizing agent.

It is recalled that the notion of "tone" is based on the classification of natural shades, a tone separating each shade from that immediately following it or preceding it. This definition and the classification of natural shades are well known to hair styling professionals and are published in the book "Sciences des traitements capillaires" [Science of hair treatment] by Charles Zviak 1986, Ed. Masson, pp. 215 and 278.

The tone heights range from 1 (black) to 10 (very light blond), one unit corresponding to a tone; the higher the figure, the lighter the shade.

While such compositions constitute a progress in this field, it is still the case however that the storage stability of these compositions can be improved.

Moreover, it would also be advantageous to further increase the fastness to washing and to shampoo of the colorations obtained by means of these compositions.

DETAILED DESCRIPTION OF THE INVENTION

It has been found, completely unexpectedly, that compositions comprising at least one particular direct compound derived from carbocyanine made it possible to obtain colorations whose properties are improved in particular in terms of fastness and selectivity (variation of coloration between the various parts of a hair strand or of a head of hair) while having improved stability of said composition.

These properties are most particularly advantageous for fluorescent compounds in the context of lightening without the need to use an oxidizing agent.

The first subject of the present invention is therefore a composition comprising, in a cosmetically acceptable medium, at least one direct dye of the following formula (I):

$$\text{(I)}$$

[Structural formula with substituents $R_1$, $R_2$, $R_3$, $R_3'$, $R_5$, $R_6$, $R_7$, X, W, Y, $(A^-)_p$, n, m]

in which:

X may represent O, S, CRR' or $NR_8$;

W may represent $CR_9R_4$ or O;

$R_1$, $R_2$, independently of each other, represent a hydrogen atom, a trihalomethyl group, a halogen atom, a $C_6$-$C_{30}$ aryl group, a cyano group, a sulfo group, an amino group, an acylamino group, a ($C_1$-$C_4$)alkoxycarbonyl group, a $C_1$-$C_6$ carboxyalkoxy group, a dialkylaminosulfonyl group for which the alkyl radicals form a 5- or 6-membered ring with the nitrogen atom to which they are attached, a linear, branched or cyclic alkyl radical comprising from 1 to 22 carbon atoms, more particularly from 1 to 6 carbon atoms, which is optionally substituted with at least one group chosen from a hydroxyl group, a linear or branched $C_1$-$C_6$ alkoxy group, a $C_1$-$C_6$ cycloalkoxy group, an optionally substituted aryl group, a carboxyl group, a sulfo group or a halogen atom, $R_1$, $R_2$, with the carbon atoms to which they are attached, can form a fused aromatic ring, R and R', independently of each other, represent a $C_1$-$C_4$ alkyl radical, $R_9$ represents a hydrogen atom, a $C_1$-$C_4$ alkyl radical, $R_3$, $R'_3$ and $R_4$ represent, independently of each other, a hydrogen atom, a $C_1$-$C_4$ alkyl radical or a ($C_2$-$C_6$)acyloxy radical, $R_3$ and $R_4$ can form, with each other and the carbon atoms bearing them, a $C_6$-$C_{30}$ aryl ring, $R_8$ denotes a radical chosen from $C_1$-$C_6$ alkyl, ($C_2$-$C_4$)acylaminosulfonyl ($C_1$-$C_6$) alkyl, ($C_1$-$C_6$)alkylsulfonylaminocarbonyl($C_1$-$C_6$)alkyl, ($C_1$-$C_6$)hydroxyalkyl, ($C_2$-$C_6$) acyloxy($C_1$-$C_6$)alkyl, ($C_1$-$C_6$)sulfatoalkyl and ($C_1$-$C_6$) cyanoalkyl radicals, $R_5$ represents a hydrogen atom, a linear or branched alkyl radical or a cycloalkyl radical comprising from 1 to 22 carbon atoms, more particularly from 1 to 6 carbon atoms, $R_7$, $R_6$, which are independent of each other, represent a hydrogen atom, a linear or branched alkyl radical or a cycloalkyl radical, an alkoxy radical, a (di)alkylamino radical, a thioalkyl radical, comprising from 1 to 22 carbon atoms, more particularly from 1 to 6 carbon atoms; a phenyl radical; a phenoxy radical; a diphenylamino radical; a halogen atom;

two substituents $R_6$ or $R_7$ belonging to two different double bonds may form with each other a ring optionally substituted with one or more phenyl or $C_1$-$C_4$ alkyl groups containing at least one double bond, optionally fused with a phenyl ring, $R_7$ and optionally R6 form(s) with Y an optionally fused heterocyclic residue containing in total from 5 to 30 members and from 1 to 5 heteroatoms, Y is a (di)alkylamino radical with identical or nonidentical, linear or branched $C_1$-$C_{10}$ alkyl radicals optionally substituted with a ($C_1$-$C_4$)alkylsulfonylamino group or with a ($C_1$-$C_4$)(di)alkylamino radical; or a residue of a heterocyclic or $C_6$-$C_{30}$ aromatic ring containing in total from 5 to 30 members and from 1 to 5 heteroatoms, which is optionally fused;

these rings being unsubstituted or substituted with at least one group chosen from $C_1$-$C_4$ alkyl, ($C_1$-$C_4$)alkoxy($C_1$-$C_4$) alkyl, amino, ($C_1$-$C_4$)dialkylamino, halogen, phenyl, carboxyl, ($C_1$-$C_4$)carboxyalkyl, ($C_1$-$C_4$)trialkylammonio($C_1$-$C_4$)alkyl, optionally substituted arylalkyl and haloalkyl groups, n may take the values from 1 to 3, m may take the values 0, 1, 2 or 3, p may take the values 0 or 1, $A^-$ represents an organic or inorganic anion.

Its subject is likewise a method for treating keratin fibers, more particularly human keratin fibers, in which the composition according to the invention is applied to said fibers, dry or wet, for a sufficient time to develop the coloration, after which the resulting fibers are rinsed, optionally washed with shampoo, rinsed again and dried or left to dry.

According to a variant of the method, the composition according to the invention is applied to said fibers, dry or wet, without a final rinse.

Another subject of the invention consists of a device comprising the composition according to the invention.

Finally, the invention relates to the use of the composition according to the invention as agent for lightening keratin fibers, and/or as agent for dyeing these fibers.

However, other characteristics and advantages of the invention will emerge more clearly on reading the description and the examples which follow.

In the text which follows, and unless otherwise stated, the limits of a range of values are understood to form part of this range.

The composition according to the invention makes it possible to obtain colorations which are lighter than the original color of the keratin fibers, when it is applied to dark fibers, without the presence of an oxidizing agent being necessary. However it is of course not out of the question for the composition according to the invention to comprise such an agent.

According to the present invention, the expression human keratin fibers is understood to mean the hair, the eyelashes and the eyebrows.

It should be noted that the composition is appropriate for the treatment of keratin fibers regardless of their coloration before treatment and whether this coloration is natural or obtained artificially.

According to one advantageous embodiment of the invention, the composition is intended to be applied to dark keratin fibers. More particularly, the dark keratin fibers are pigmented fibers or alternatively artificially dyed fibers, of which the tone height is less than or equal to 6, and preferably less than or equal to 4.

Also falling within the scope of the present invention are the mesomeric forms of the compounds of formula (I).

According to one variant of the invention, m is equal to 0 or 1.

In accordance with a more particular embodiment of the invention, $R'_3$ denotes a hydrogen atom.

Moreover, $R_3$ or $R_4$ denote more particularly a hydrogen atom or a $C_1$-$C_4$ alkyl radical.

The direct dye entering into the composition according to the invention is generally a fluorescent molecule, that is to say which dyes by itself, absorbs light from the visible spectrum and additionally optionally ultraviolet light (wavelengths ranging from 360 to 760 nanometers) but which, unlike a conventional dye, converts part of the absorbed energy into fluorescent light of longer wavelength than that absorbed, emitted in the visible part of the spectrum.

In addition, the fluorescent dye according to the invention is a dye which generates fluorescence on the support to which it is applied.

According to the present invention, the direct dye is preferably soluble in the medium of the composition at at least 1 gram per liter and preferably at at least 5 grams per liter at the temperature of 25° C.

It should be noted that $A^-$ may be an anion of inorganic origin, chosen in particular from halides, sulfates, bisulfates, nitrates, phosphates, hydrogen phosphates, dihydrogen phosphates, boronates, carbonates and bicarbonates.

The anion $A^-$ may also be of organic origin, and in this case, may be chosen more particularly from those obtained from salts of saturated or unsaturated, aromatic or nonaromatic, mono- or polycarboxylic, sulfonic or sulfuric acids, optionally substituted with at least one hydroxyl or amino radical, or halogen atoms.

Preferably, $A^-$ is chosen from chloride, iodide, sulfate, methosulfate and ethosulfate.

In accordance with a particularly advantageous embodiment of the invention, the direct dye of formula (I) corresponds to one of the following compounds:

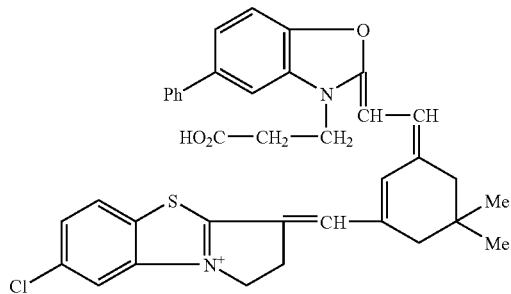
I⁻
Iodide of 1-[[3-[(3,4-dihydro[1,4]oxazino[3,4-b]-benzothiazol-1-yl)methylene]-1-cyclohexen-1-yl]methylene]-3,4-dihydro
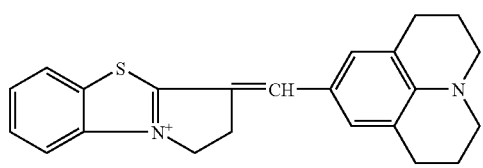
ClO₄⁻
Perchlorate of pyrrolo[2,1-b]benzothiazolium, 2,3-dihydro-3-[(2,3,6,7-tetrahydro-1H,5H-benzo[ij]quinolizin-9-yl)methylene]
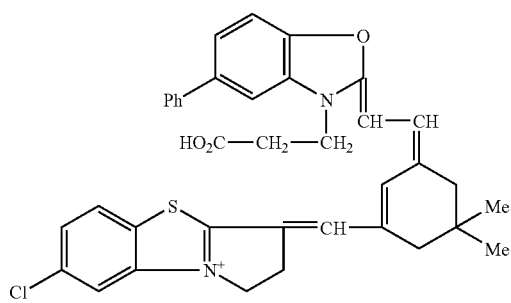
•Br⁻
Bromide of 1H-pyrrolo[2,1-b]-benzothiazolium, 3-[[3-[[3-(2-carboxyethyl)-5-phenyl-2(3H)-benzoxazolylidene)-ethylidene]-5,5-dimethyl-1-cyclohexen-1-yl]methylene]-7-chloro-2,3-dihydro -continued

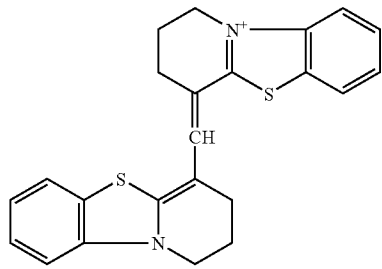

ClO$_4^-$
Perchlorate of pyrido[2,1-b]-
benzothiazolium, 4-[(2,3-
dihydro-1H-pyrido[2,1b]-
benzothiazol-4-yl)methylene]-
1,2,3,4-tetrahydro

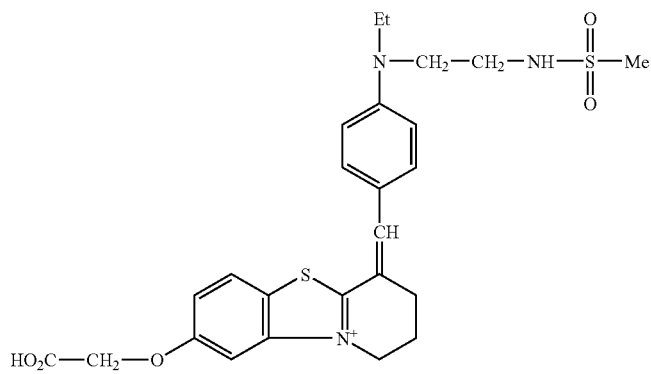

•Cl-
Chloride of pyrido[2,1-
b]benzothiazolium,
8-(carboxymethoxy)-4-[[4-
[ethyl[2-[(methylsulfonyl)-
amino]ethyl]amino]phenyl]-
methylene]-1,2,3,4-
tetrahydro-,

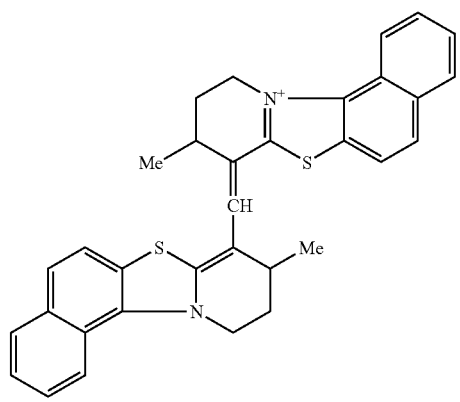

Cl-
Salt (for example chloride)
of naphtho[1',2':4,5]-
thiazolo[3,2-a]pyridinium,
8-[[10,11-dihydro-9-methyl-
9H-naphtho[1',2':4,5]-
thiazolo[3,2-a]pyridine-
8-yl)methylene]-8,9,10,11-
tetrahydro-9-methyl-

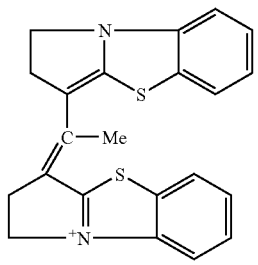
Cl⁻
Salt (for example chloride)
of 1H-pyrrolo[2,1-b]benzo-
thiazolium, 3-[1-(1,2-
dihydropyrrolo[2,1-b]benzo-
thiazol-3-yl)ethylidene]-
2,3-dihydro
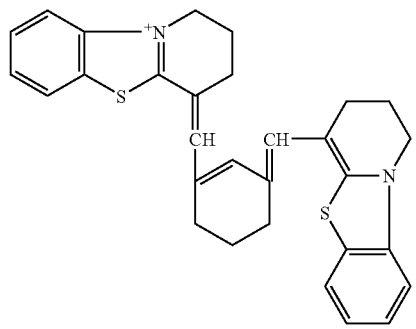
•I⁻
Iodide of pyrido[2,1-b]-
benzothiazolium, 4-[[3-[(2,3-
dihydro-1H-pyrido[2,1-b]-
benzothiazol-4-yl)methylene)-
1-cyclohexen-1-yl]methylene]-
1,2,3,4-tetrahydro
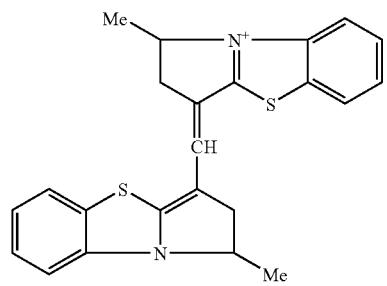
ClO₄⁻
Perchlorate of 3-[(1,2-
dihydro-1-methylpyrrolo[2,1-
b]benzothiazol-3-
yl)methylene]-2,3-dihydro-
1-methyl-1H-pyrrolo[2,1-
b]benzothiazolium -continued
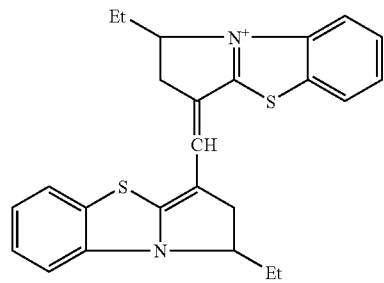
ClO$_4^-$
Perchlorate of 1-ethyl-3-[(1-ethyl-1,2-dihydropyrrolo[2,1-b]benzothiazol-3-yl)methylene]-2,3-dihydro-1H-pyrrolo[2,1-b]benzothiazolium
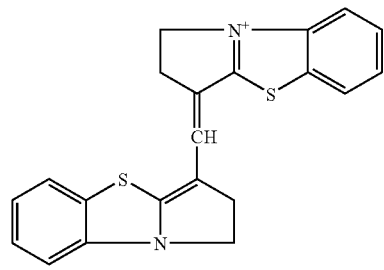
ClO$_4^-$
Perchlorate of 3-[(1,2-dihydropyrrolo[2,1-b]benzothiazol-3-yl)methylene]-2,3-dihydro-1H-pyrrolo[2,1-b]benzothiazolium
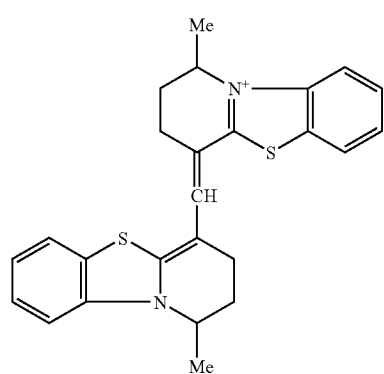
ClO$_4^-$
Perchlorate of 4-[(2,3-dihydro-1-methyl-1H-pyrido[2,1-b]benzothiazol-4-yl)methylene]-1,2,3,4-tetrahydro-1-methylpyrido[2,1-b]benzothiazolium

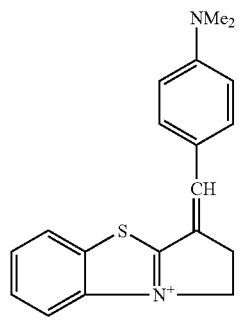
ClO₄⁻
Perchlorate of 1H-
pyrrolo[2,1-
b]benzothiazolium, 3-[[4-
(dimethylamino)phenyl]-
methylene]-2,3-dihydro
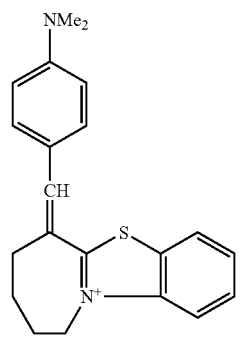
•Br-
Bromide of 6-[p-
(dimethylamino)benzylidene]-
7,8,9,10-tetrahydro-6H-
azepino[2,1-b]
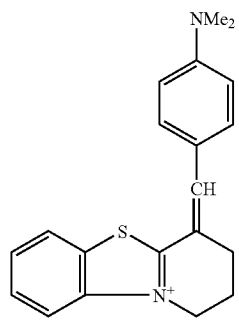
•Br-
Bromide of 4-[p-
(dimethylamino)benzylidene]-
1,2,3,4-tetrahydro-
pyrido[2,1-b]

-continued

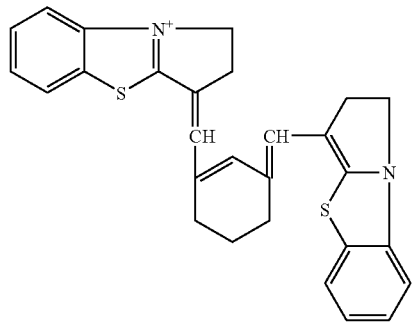

•Br-
Bromide of 1H-pyrrolo[2,1-b]benzothiazolium, 3-[[3-[(1,2-dihydropyrrolo[2,1-b]benzothiazol-3-yl)methylene]-1-cyclohexen-1-yl)methylene]-2,3-dihydro

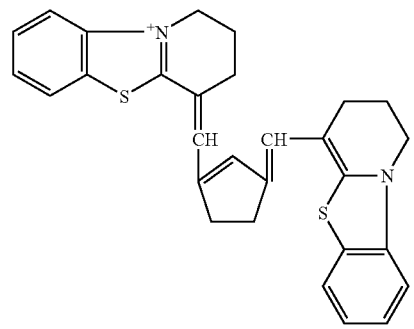

I-
Iodide of pyrido[2,1-b]benzothiazolium, 4-[[3-[(2,3-dihydro-1H-pyrido[2,1-b]benzothiazol-4-yl)methylene]-1-cyclopenten-1-yl]methylene]-1,2,3,4-tetrahydro

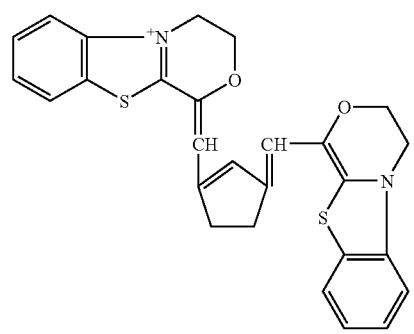

•I-
Iodide of 1H-[1,4]oxazino[3,4-b]benzo-thiazolium, 1-[[3-[(3,4-dihydro[1,4]oxazino[3,4-b]benzothiazol-1-yl)methylene]-1-cyclopenten-1-yl)methylene]-3,4-dihydro,

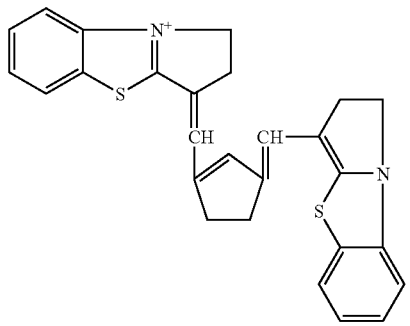
1H-Pyrrolo[2,1-
b]benzothiazolium, 3-[[3-
[(1,2-dihydropyrrolo[2,1-
b]benzothiazol-3-
yl)methylene]-1-cyclopenten-
1-yl]methylene]-2,3-dihydro-
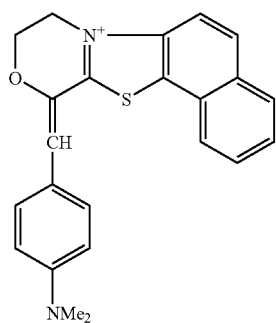
$ClO_4^-$
Perchlorate of 9H-naphtho-
[2',1':4,5]thiazolo[2,3-
c] [1,4-oxazinium, 11-[[4-
(dimethylamino)phenyl]-
methylene]-8,11-dihydro-,
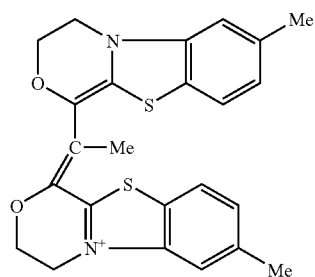
Cl-
Salt (for example chloride)
of 1H-[1,4]oxazino[3,4-
b]benzothiazolium, 1-[1-(3,4-
dihydro-7-methyl[1,4]oxazino
[3,4-b]benzothiazol-
1-yl)ethylidene]-3,4-dihydro-
7-methyl

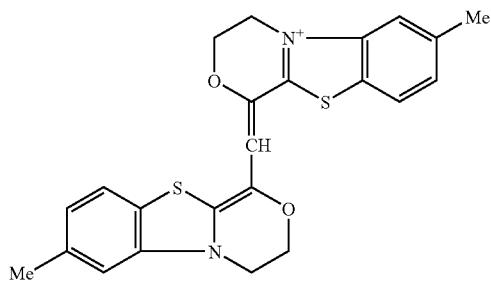

Cl-
Salt (for example chloride)
of 1H-[1,4]oxazino[3,4-
b]benzothiazolium, 1-[(3,4-
dihydro-7-methyl[1,4]oxazino-
[3,4-b]benzothiazol-
1-yl)methylene]-3,4-dihydro-
7-methyl

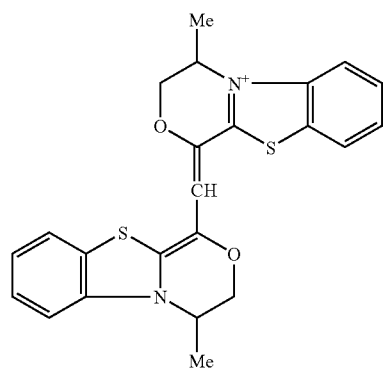

Cl-
Salt (for example chloride)
of 1H-[1,4]oxazino[3,4-
b]benzothiazolium, 1-[(3,4-
dihydro-4-methyl[1,4]oxazino-
[3,4-b]benzothiazol-1-
yl)methylene]-3,4-dihydro-
4-methyl

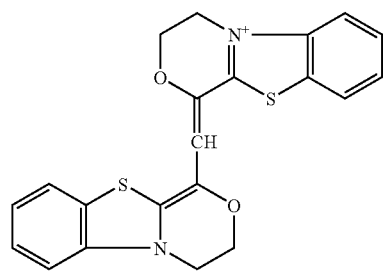

Methylbenzene sulfonate of
1H-[1,4]oxazino[3,4-
b]benzothiazolium, 1-[(3,4-
dihydro[1,4]oxazino[3,4-
b]benzothiazol-
1-yl)methylene]-3,4-dihydro

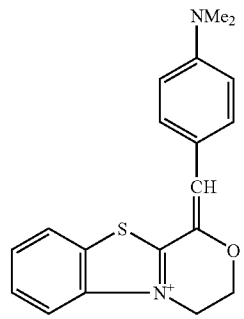
ClO$_4^-$
1H-[1,4]Oxazino[3,4-
b]benzothiazolium,
1-[[4-(dimethylamino)phenyl]-
methylene]-3,4-dihydro
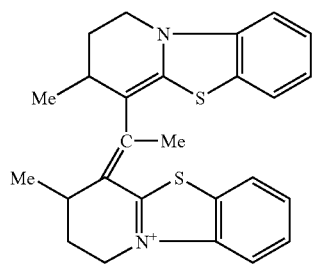
•I-
Iodide of pyrido[2,1-
b]benzothiazolium, 4-[1-(2,3-
dihydro-3-methyl-1H-
pyrido[2,1-b]benzothiazol-
4-yl)ethylidene]-1,2,3,4-
tetrahydro-3-methyl
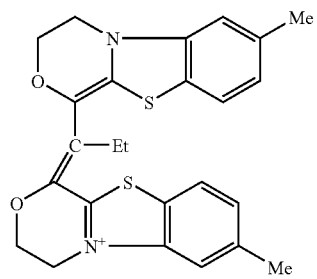
•I-
Iodide of 1H-
[1,4]oxazino[3,4-b]benzo-
thiazolium, 1-[1-(3,4-
dihydro-7-methyl[1,4]oxazino-
[3,4-b]benzothiazol-
1-yl)propylidene]-3,4-
dihydro-7-methyl

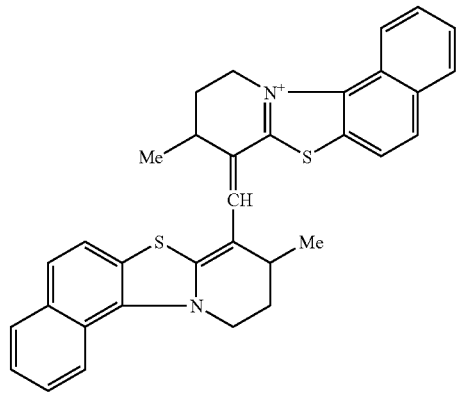
Iodide of
naphtho[1',2':4,5]thiazolo-
[3,2-a]pyridinium, 8-[(10,11-
dihydro-9-methyl-9H-
naphtho[1',2':4,5]thiazolo-
[3,2-a]pyridin-8-
yl)methylene]-8,9,10,11-
tetrahydro-9-methyl
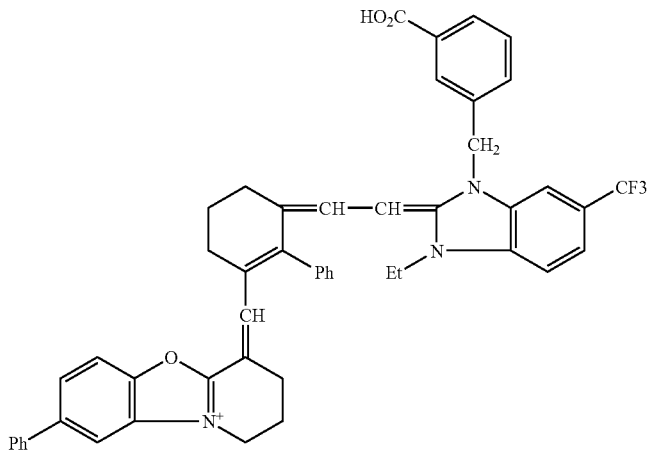
Cl-
Salt (for example chloride)
of pyrido[2,1-
b]benzoxazolium, 4-[[3-[[3-
[(3-carboxyphenyl)methyl]-1-
ethyl-1,3-dihydro-5-
(trifluoromethyl)-2H-
benzimidazol-2-
ylidene]ethylidene]-2-phenyl-
1-cyclohexen-1-yl]methylene]-
1,2,3,4-tetrahydro-8-phenyl
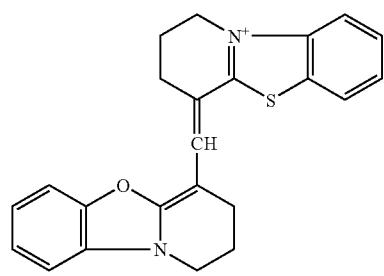
Tetrafluoroboronate of pyrido[2,1-b]benzoxazolium, 4-[(2,3-dihydro-1H-pyrido[2,1-b]benzoxazol-4-yl)methylene]-1,2,3,4-tetrahydro

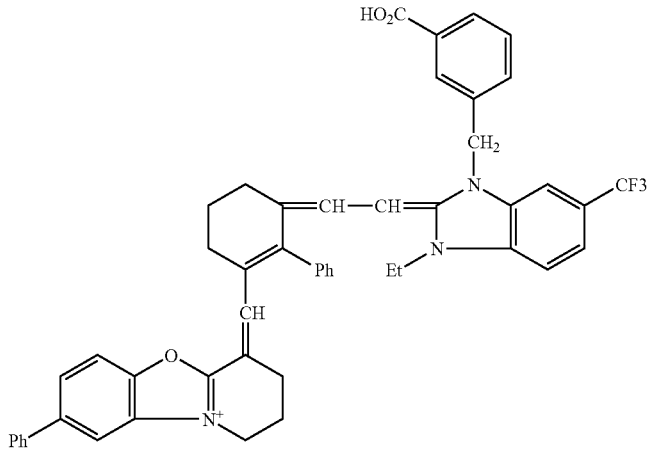

•I⁻
Iodide of pyrido[2,1-b]benzoxazolium, 4-[[3-[[3-(3-carboxyphenyl)methyl]-1-ethyl-1,3-dihydro-5-(trifluoromethyl)-2H-benzimidazol-2-ylidene]ethylidene]-2-phenyl-1-cyclohexen-1-yl]methylene]-1,2,3,4-tetrahydro-8-phenyl

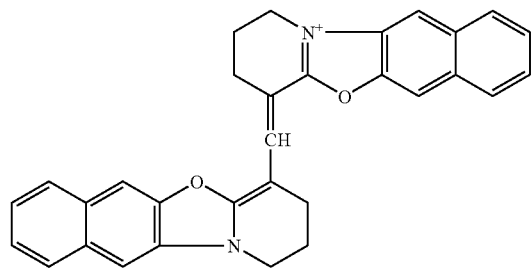

•I⁻
Iodide of naphth[2',3':4,5]oxazolol[3,2-a]pyridinium, 4[(2,3-dihydro-1H-naphthl[2',3':4,5]oxazolo[3,2-a]pyridin-4-yl)methylene]-1,2,3,4-tetrahydro

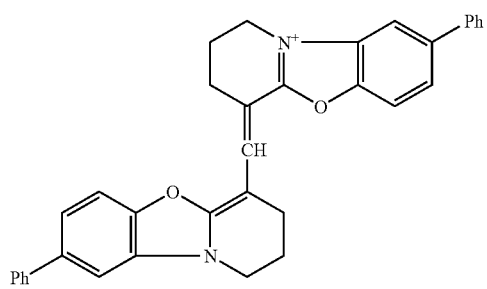

•Br⁻
Bromide of pyrido[2,1-b]benzoxazolium, 4-[(2,3- dihydro-8-phenyl-1H-
pyrido[2,1-b]benzoxazol-
4-yl)methylene]-1,2,3,4-
tetrahydro-8-phenyl
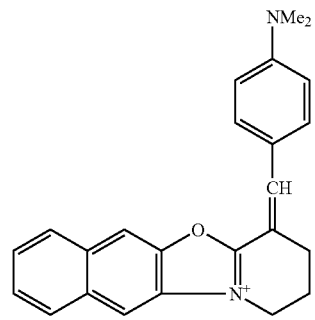
•I-
Iodide of
naphth[2',3':4,5]oxazolo[3,2-
a]pyridinium, 4-[p-
(dimethylamino)benzylidene]-
1,2,3,4-tetrahydro
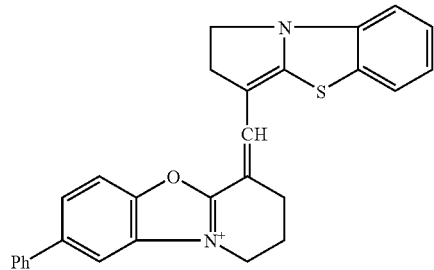
•Br-
Bromide of pyrido[2,1-
b]benzoxazolium, 4-[(1,2-
dihydropyrrolo[2,1-
b]benzothiazol-
3-yl)methylene]-1,2,3,4-
tetrahydro-8-phenyl
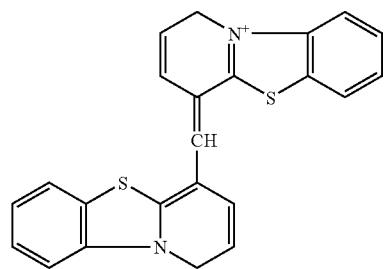
•I-
Iodide of pyrido[2,1-
b]benzothiazolium,
1,4-dihydro-4-(1H-pyrido[2,1-
b]benzothiazol-4-ylmethylene)

-continued
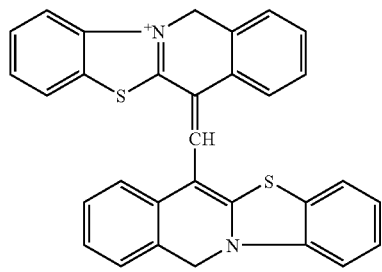
ClO$_4^-$
Perchlorate of
benzothiazolo[3,2-
b]isoquinolinium, 6-(11H-
benzothiazolo[3,2-
b]isoquinolin-6-ylmethylene)-
6,11-dihydro
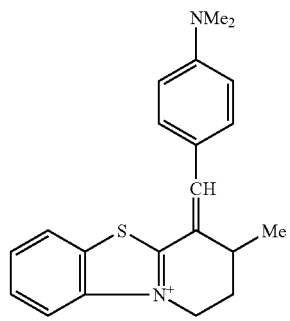
Iodide of pyrido[2,1-
b]benzothiazolium,
4-[[4-(dimethylamino)phenyl]-
methylene]-1,2,3,4-
tetrahydro-3-methyl
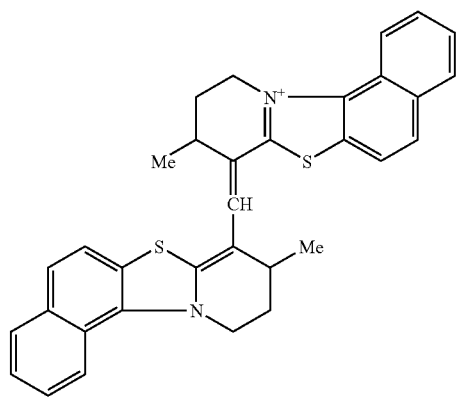
ClO$_4^-$
Perchlorate of pyrido[2,1-
b]berizothiazolium,
4-[[3-[(2,3-dihydro-1H-
pyrido[2,1-b]benzothiazol-
4-yl)methylene]-5-methyl-
1-cyclohexen-1-yl]methylene]-
1,2,3,4-tetrahydro-

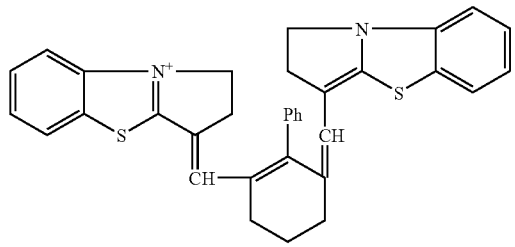

Tetrafluoroborate of 1H-
pyrrolo[2,1-
b]benzothiazolium, 3-[[3-
[(1,2-dihydropyrrolo[2,1-
b]benzothiazol-
3-yl)methylene]-2-phenyl-
1-cyclohexen-1-yl]methylene]-
2,3-dihydro

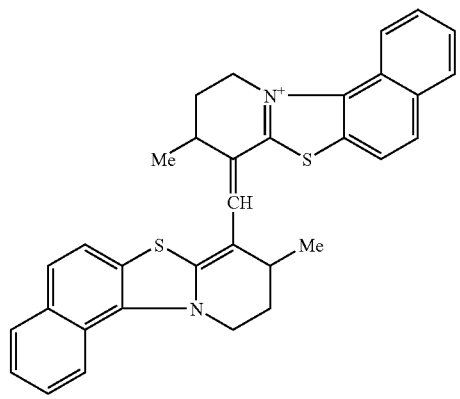

Cl-
Salt (for example chloride)
of naphtho[1',2':4,5]-
thiazolo[3,2-a]pyridinium,
8-[(10,11-dihydro-9-methyl-
9H-naphtho[1',2':4,5]-
thiazolo[3,2-a]pyridin-
8-yl)methylene]-8,9,10,11-
tetrahydro-9-methyl-

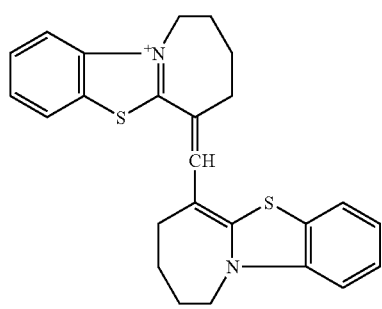

Perchlorate of 7,8,9,10-
tetrahydro-6-[(7,8,9,10-
tetrahydroazepino[2,1-
b]benzothiazol-
6-yl)methylene]-6H-
azepino[2,1-b]benzothiazolium

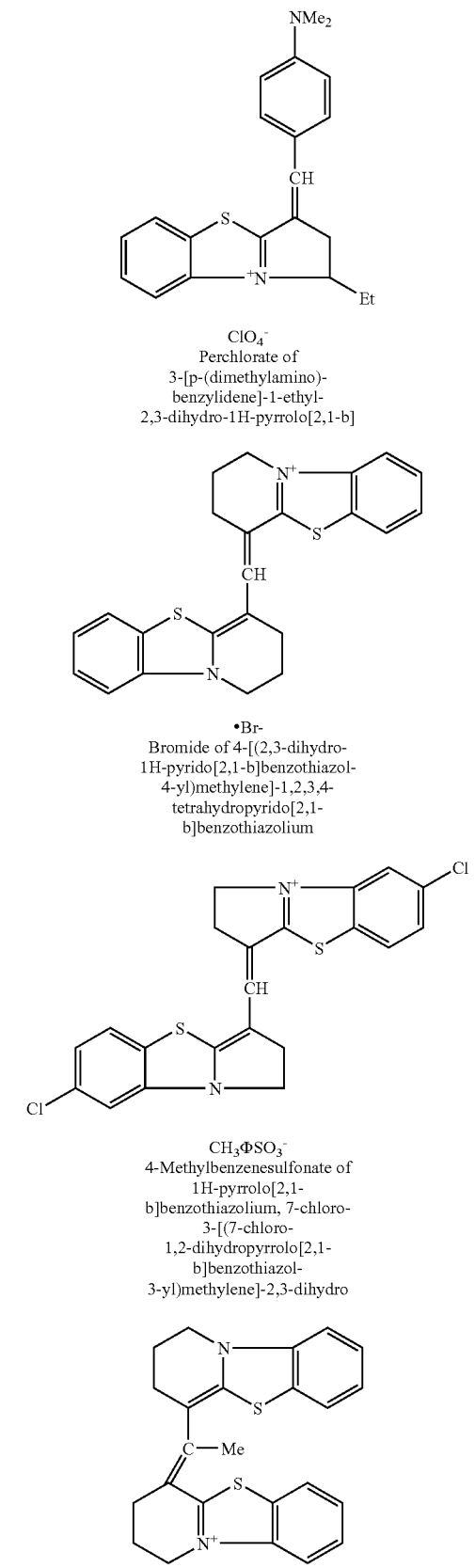

-continued

CH₃ΦSO₃⁻
4-Methylbenzenesulfonate of pyrido[2,1-b]benzothiazolium, 4-[1-(2,3-dihydro-1H-pyrido[2,1-b]benzothiazol-4-yl)ethylidene]-1,2,3,4-tetrahydro-

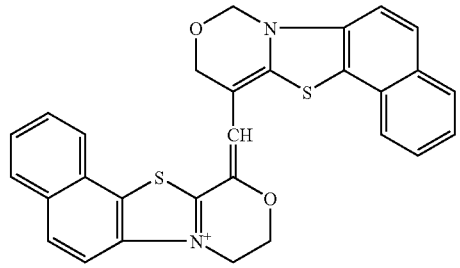

•Br⁻
Bromide of 9H-naphtho-[2',1':4,5]thiazolo[2,3-c] [1,4]oxazinium, 11-[(8,9-dihydronaphtho[2',1':4,5]-thiazolo[2,3-c] [1,4]oxazin-11-yl)methylene]-8,11-dihydro-,

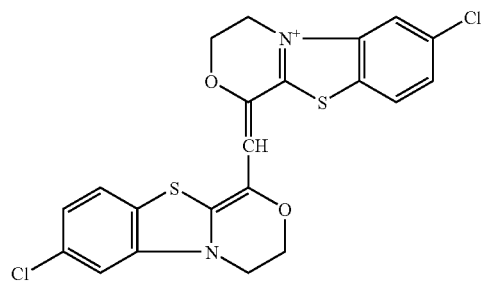

CH₃ΦSO₃⁻
Methylbenzenesulfonate of 1H-[1,4]oxazino[3,4-b]benzothiazolium, 7-chloro-1-[(7-chloro-3,4-dihydro[1,4]oxazino[3,4-b]benzothiazol-1-yl)methylene]-3,4-dihydro

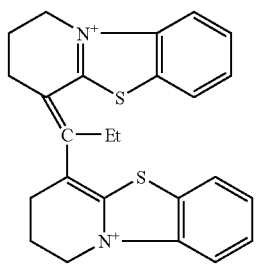

CH₃ΦSO₃⁻
Methylbenzenesulfonate of pyrido[2,1-b]benzothiazolium, 4-[1-(2,3-dihydro-1H-pyrido[2,1-b]benzothiazol-4-yl)propylidene]-1,2,3,4-tetrahydro -continued

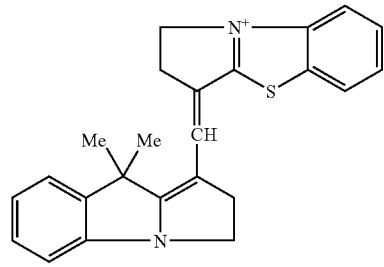

•Br⁻
Bromide of 1H-pyrrolo[2,1-b]benzothiazolium, 3-[(2,3-dihydro-9,9-dimethyl-9H-pyrrolo[1,2-a]indol-1-yl)methylene]-2,3-dihydro-,

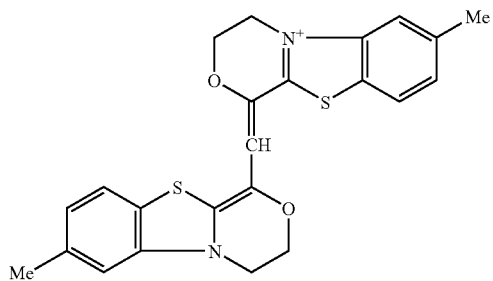

CH₃ΦSO₃⁻
4-Methylbenzenesulfonate of 1H-[1,4]oxazino[3,4-b]benzothiazolium, 1-[(3,4-dihydro-7-methyl[1,4]oxazino[3,4-b]benzothiazol-1-yl)methylene]-3,4-dihydro-7-methyl

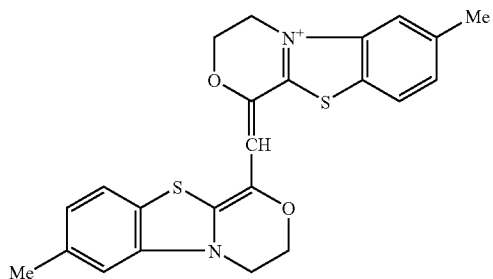

CH₃ΦSO₃⁻
4-Methylbenzenesulfonate of 1H-[1,4]oxazino[3,4-b]benzothiazolium, 1-[(3,4-dihydro-7-methyl[1,4]oxazino[3,4-b]benzothiazol-1-yl)methylene]-3,4-dihydro-7-methyl

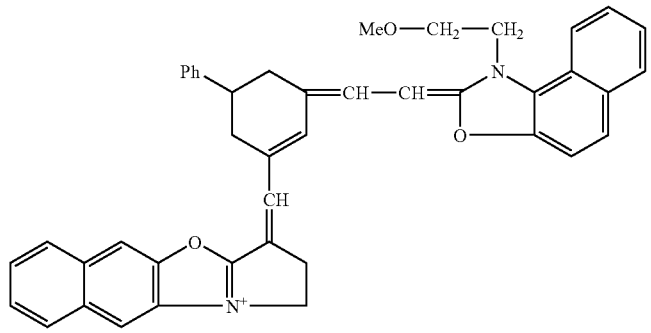
Tetrafluoroborate of
1H-naphtho[2,3-d]pyrrolo[2,1-
b]oxazolium, 2,3-dihydro-
3-[[3-([1-(2-
methoxyethyl)naphth[1,2-
d]oxazol-2-(1H)-
ylidene]ethylidene]-5-phenyl-
1-cyclohexen-1-yl]methylene]
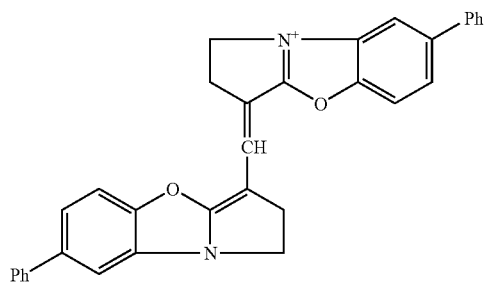
•Br-
Bromide of 1H-pyrrolo[2,1-
b]benzoxazolium, 3-[(1,2-
dihydro-1-phenylpyrrolo[2,1-
b]benzoxazol-3-yl)methylene]-
2,3-dihydro-7-phenyl
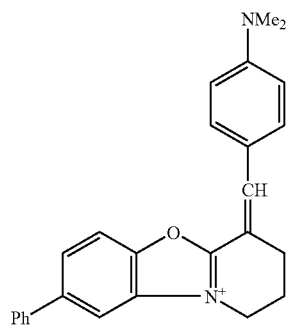
•I-
Iodide of pyrido[2,1-
b]benzoxazolium, 4-[p-
(dimethylamino)benzylidene]-
1,2,3,4-tetrahydro-8-phenyl -continued

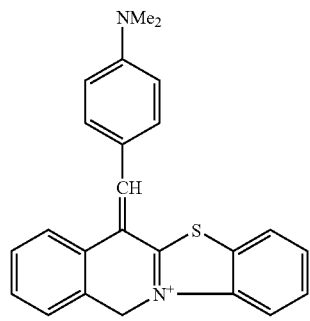

Perchlorate of
benzothiazolo[3,2-
b]isoquinolinium, 6-[[4-
(dimethylamino)phenyl]-
methylene]-6,11-dihydro-

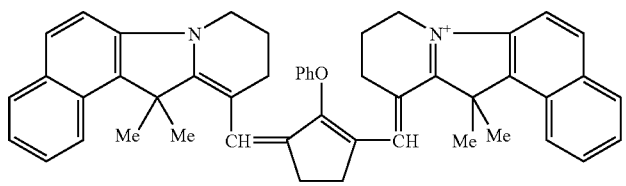

Hexafluorophosphate of
8H-benzo[e]pyrido[1,2-
a]indolium, 9,10,11,12-
tetrahydro-12,12-dimethyl-11-
[[2-phenoxy-3-[(8,9,10,12-
tetrahydro-12,12-
dimethylbenzo[e]pyrido[1,2-
a]indol-11-yl)methylene]-1-
cyclopenten-1-yl]methylene]

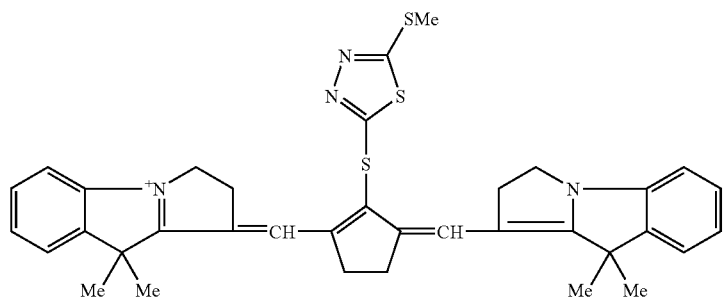

Trifluoromethanesulfonate of
pyrrolo[1,2-a]indolium,
1-[[3-[(2,9-dihydro-9,9-
dimethyl-3H-pyrrolo[1,2-
a]indol-1-yl)methylene]-2-
[[5-(methylthio)-1,3,4-
thiadiazol-2-yl]thio]-1-
cyclopenten-1-yl]methylene]-
1,2,3,9-tetrahydro-
9,9-dimethyl -continued

PAGE 1-A

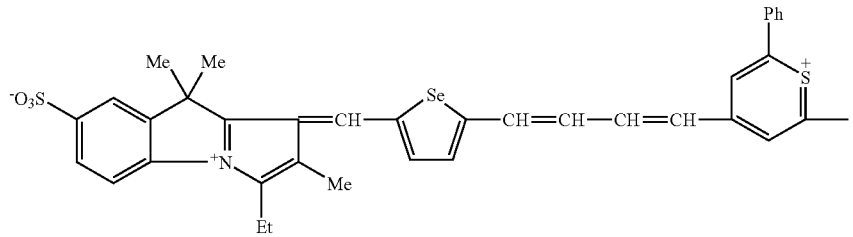

PAGE 1-B

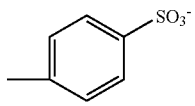

Inner salt of pyrrolo[1,2-a]indolium, 3-ethyl-1,9-dihydro-
2,9,9-trimethyl-1-[[5-[4-[2-phenyl-6-(4-
sulfophenyl)thiopyrylium-4-yl]-1,3-butadienyl]selenophene-2-
yl]methylene]-7-sulfo

PAGE 1-A

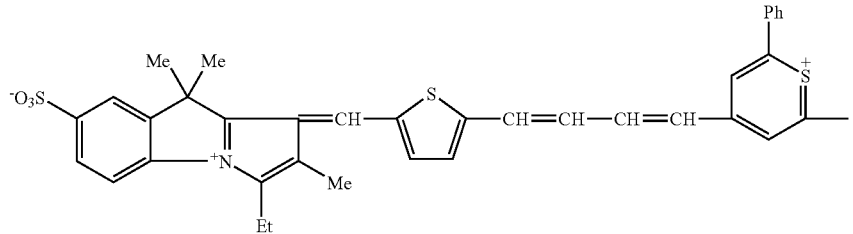

PAGE 1-B

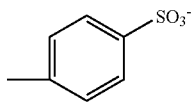

Inner salt of pyrrolo[1,2-a]indolium, 3-ethyl-1,9-dihydro-
2,9,9-trimethyl-1-[[5-[4-[2-phenyl-6-(4-
sulfophenyl)thiopyrylium-4-yl]-1,3-butadienyl-
2-thienyl]methylene]-7-sulfo

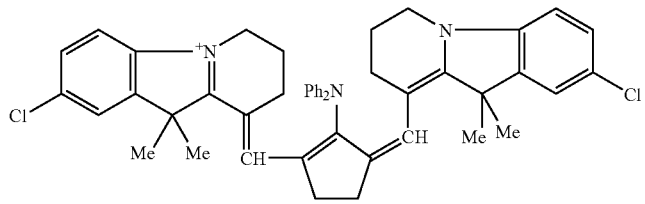

$CH_3SO_3^-$
Methanesulfonate of
6H-pyrido[1,2-a]indolium,
2-chloro-9-[[3-[(2-chloro-
6,7,8,10-tetrahydro-10,10-
dimethylpyrido[1,2-a]indol-
9-yl)methylene]-2-
(diphenylamino)-1-
cyclopenten-1-yl]methylene]-
7,8,9,10-tetrahydro-10,10-
dimethyl

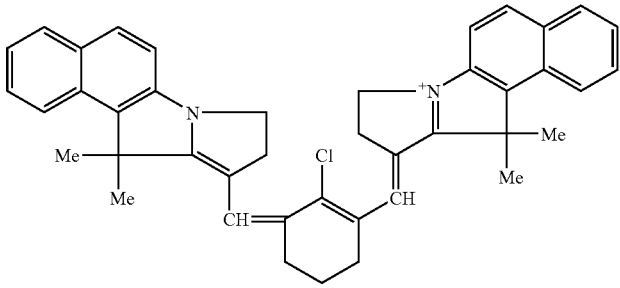

CH₃ΦSO₃⁻
4-Methylbenzenesulfonate of
benzo[e]pyrrolo[1,2-
a]indolium, 10-[[2-chloro-3-
[(9,11-dihydro-1,11-dimethyl-
8H-benzo[e]pyrrolo[1,2-
a]indol-10-yl)methylene]-1-
cyclohexen-1-yl]methylene]-
8,9,10,11-tetrahydro-11,11-
dimethyl

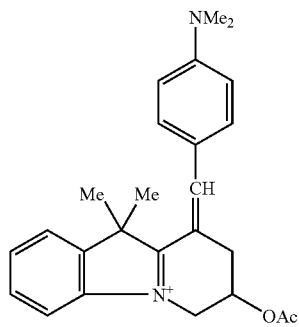

ClO₄⁻
Perchlorate of
6H-pyrido[1,2-a]indolium,
7-(acetyloxy)-9-[[4-
(dimethylamino)phenyl]-
methylene]-7,8,9,10-
tetrahydro-10,10-dimethyl

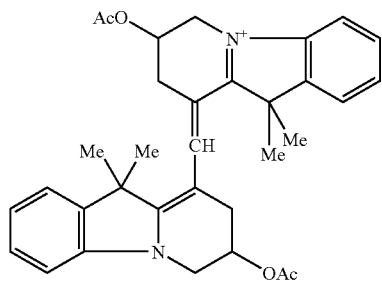

ClO₄⁻
Perchlorate of 6H-pyrido[1,2-
a]indolium, 7-(acetyloxy)-9-
[[7-(acetyloxy)-6,7,8,10-
tetrahydro-10,10-
dimethylpyrido[1,2-a]indol-
9-yl]methylene]-7,8,9,10-
tetrahydro-10,10-dimethyl -continued

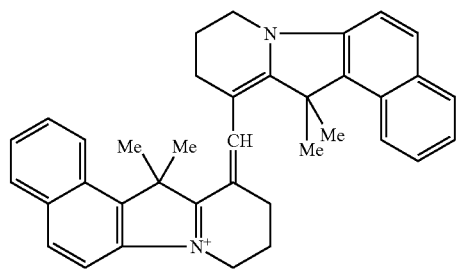

Cl⁻
Salt (for example chloride) of 8H-benzo[e]pyrido[1,2-a]indolium, 9,10,11,12-tetrahydro-12,12-dimethyl-11-[(8,9,10,12-tetrahydro-12,12-dimethylbenzo[e]pyrido[1,2-a]indol-11-yl)methylene]

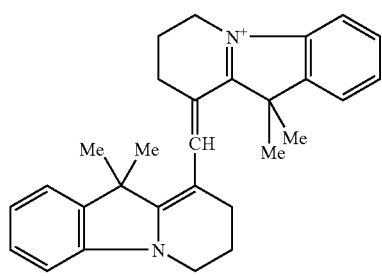

ClO₄⁻
Perchlorate of 6H-pyrido[1,2-a]indolium, 7,8,9,10-tetrahydro-10,10-dimethyl-9-[(6,7,8,10-tetrahydro-10,10-dimethylpyrido[1,2-a]indol-9-yl)methylene]

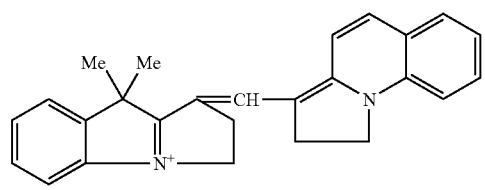

•Br⁻
Bromide of pyrrolo[1,2-a]indolium, 1-[(1,2-dihydropyrrolo[1,2-a]quinolin-3-yl)methylene]-1,2,3,9-tetrahydro-9,9-dimethyl

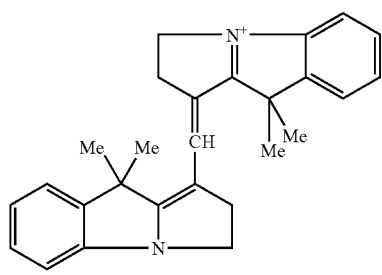

•I⁻
Iodide of pyrrolo[1,2-a]indolium, 1-[(2,9-dihydro-9,9-dimethyl- 3H-pyrrolo[1,2-a]indol-1-yl)methylene]-1,2,3,9-tetrahydro-9,9-dimethyl-

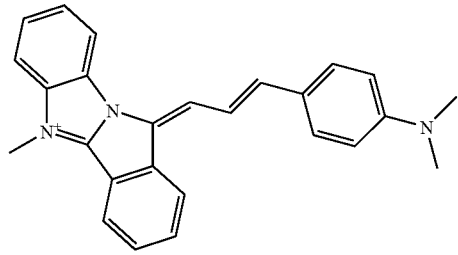

I−

Iodide of 11-[3-(4-dimethylaminophenyl)-allyidene]-5-methyl-11H-benzo[4,5]imidazo[2,1-a]isoindol-5-ium

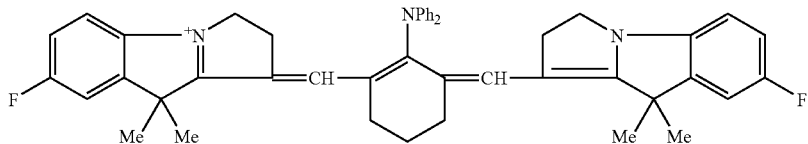

ClO₄⁻

Perchlorate of pyrrolo[1,2-a]indolium, 1-[[2-(diphenylamino)-3-[(7-fluoro-2,9-dihydro-9,9-dimethyl-3H-pyrrolo[1,2-a]indol-1-yl)methylene]-1-cyclohexen-1-yl]methylene]-7-fluoro-1,2,3,9-tetrahydro-9,9-dimethyl

PAGE 1-A

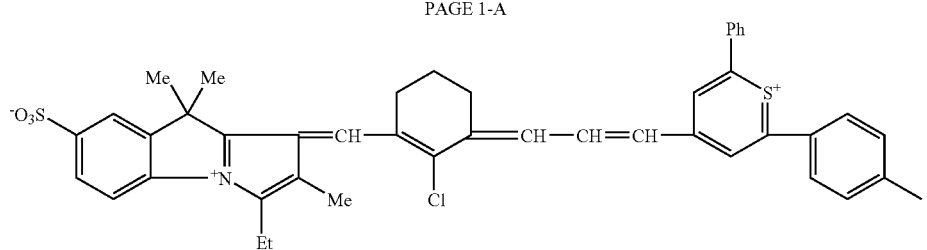

PAGE 1-B

—SO₃—

Inner salt of pyrrolo[1,2-a]indolium, 1-[[2-chloro-3-[3-[2-phenyl-6-(4-sulfophenyl)thiopyrylium-4-yl]-2-propenylidene]-1-cyclohexen-1-yl]methylene]-3-ethyl-1,9-dihydro-2,9,9-trimethyl-7-sulfo

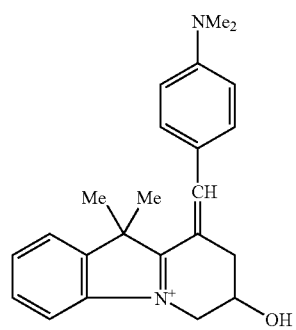

ClO$_4^-$
Perchlorate of
6H-pyrido[1,2-a]indolium,
9-[[4-(dimethylamino)phenyl]-
methylene]-7,8,9,10-
tetrahydro-7-hydroxy-10,10-
dimethyl
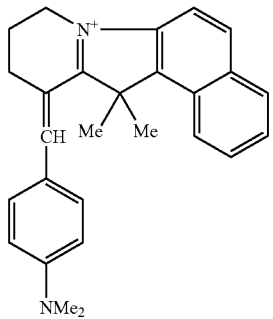
ClO$_4^-$
Perchlorate of
8H-benzo[e]pyrido[1,2-
a]indolium, 11-[[4-
(dimethylamino)phenyl]-
methylene]-9,10,11,12-
tetrahydro-12,12-dimethyl
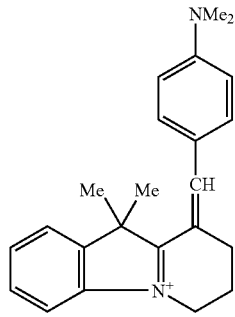
ClO$_4^-$
Perchlorate of
6H-pyrido[1,2-a]indolium,
9-[[4-(dimethylamino)phenyl]-
methylene]-7,8,9,10-
tetrahydro-10,10-dimethyl
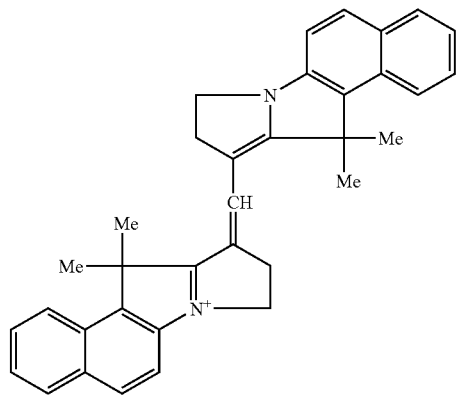
•Br-
Bromide of
benzo[e]pyrrolo[1,2- a]indolium, 10-[(9,11-dihydro-11,11-dimethyl-8H-benzo[e]pyrrolo[1,2-a]indol-10-yl)methylene]-8,9,10,11-tetrahydro-11,11-dimethyl
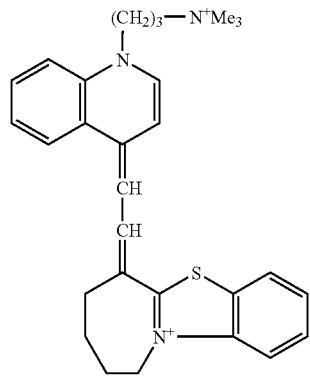
Iodide of 6H-azepino[2,1-b]benzothiazolium, 7,8,9,10-tetrahydro-6-[[1-[3-(trimethylammonio)propyl]-4(1H)-quinolinylidene]-ethylidene]
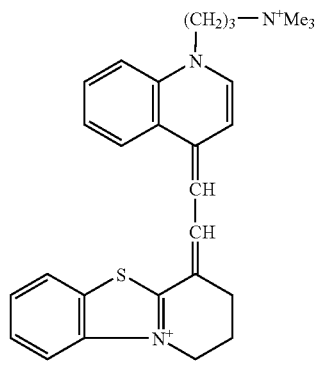
Iodide of pyrido[2,1-b]benzothiazolium, 1,2,3,4-tetrahydro-4-[[1-(3-(trimethylammonio)propyl]-4(1H)-quinolinylidene]-ethylidene]
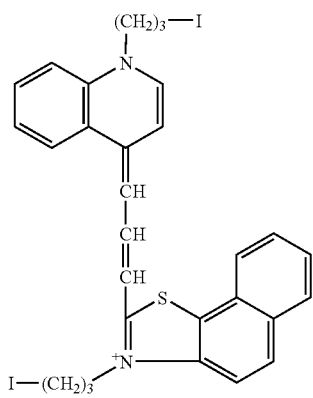

Iodide of
naphtho[2,1-d]thiazolium,
3-(3-iodopropyl)-2-[3-[1-
(3-iodopropyl)-4(1H)-
quinolinylidene]-1-propenyl]
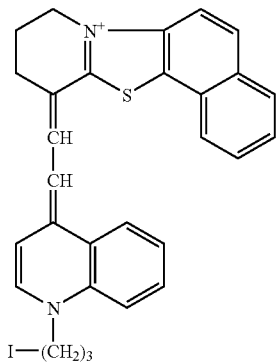
•I-
Iodide of
naphtho[2',1':4,5]thiazolo-
[3,2-a]pyridinium, 8,9,10,11-
tetrahydro-11-[[1-(3-
iodopropyl)-4(1H)-
quinolinylidene]ethylidene
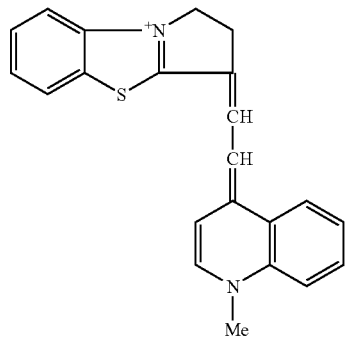
I-
Iodide of 1H-pyrrolo[2,1-
b]benzothiazolium, 2,3-
dihydro-3-[(1-methyl-4(1H)-
quinolinylidene)ethylidene]
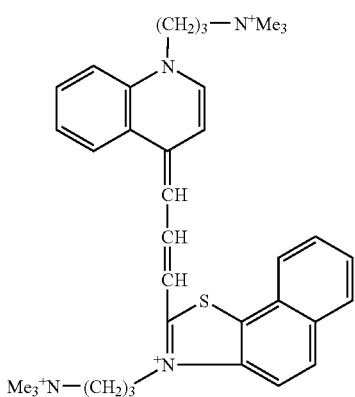
(Cl-)$_2$
Salt (for example chloride)
of naphtho[2,1-d]thiazolium,
3-[3-(trimethylammonio)- propyl]-2-[3-[1-[3-(trimethylammonio)propyl]-4(1H)-quinolinylidene]-1-propenyl]

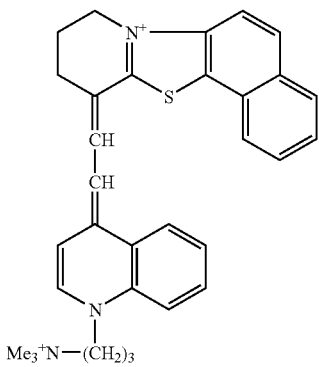

(Cl-)₂
Salt (for example chloride) of naphtho[2',1':4,5]-thiazolo[3,2-a]pyridinium, 8,9,10,11-tetrahydro-11-[[1-[3-(trimethylammonio)propyl]-4(1H)-quinolinylidene]-ethylidene]

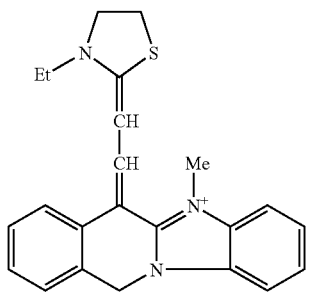

•I-
Iodide of benzimidazo[1,2-b]isoquinolinium, 6-[(3-ethyl-2-thiazolidinylidene)-ethylidene]-6,11-dihydro-5-methyl

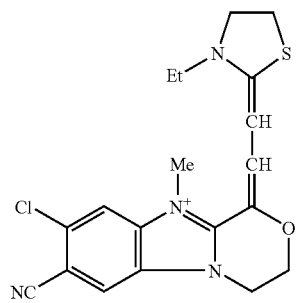

•I-
Iodide of 1H-[1,4]oxazino[4,3-a]benzimidazolium, 8-chloro-7-cyano-1-[(3-ethyl-2-thiazolidinylidene)ethylidene]-3,4-dihydro-10-methyl

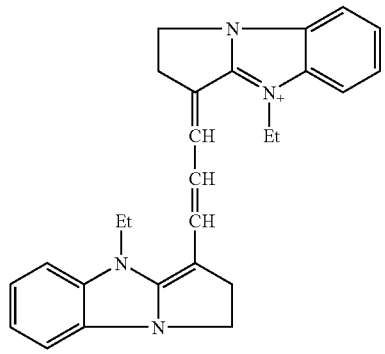
•I⁻
Iodide of 1H-pyrrolo[1,2-a]benzimidazolium, 4-ethyl-3-[3-(4-ethyl-2,4-dihydro-1H-pyrrolo[1,2-a]benzimidazol-3-yl)-2-propenylidene]-2,3-dihydro
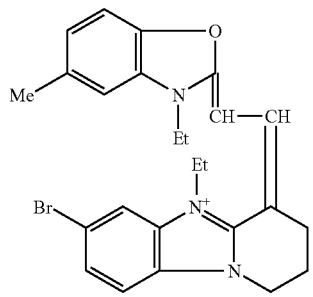
•I⁻
Iodide of pyrido[1,2-a]benzimidazolium, 7-bromo-5-ethyl-4-[(3-ethyl-5-methyl-2(3H)-benzoxazolylidene)-ethylidene]-1,2,3,4-tetrahydro
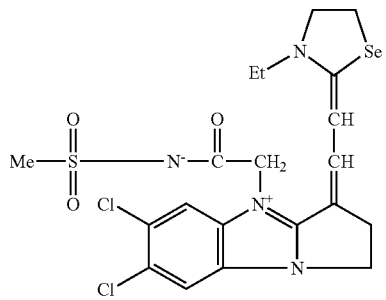
Inner salt of 1H-pyrrolo[1,2-a]benzimidazolium, 6,7-dichloro-3-[(3-ethyl-2-selenazolidinylidene)-ethylidene]-2,3-dihydro-4-[2-[(methylsulfonyl)amino]-2-oxoethyl]

-continued

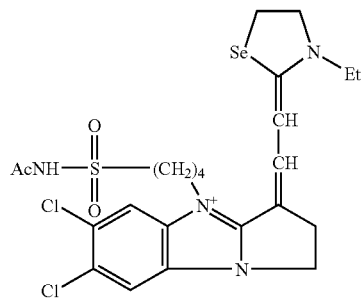

•I⁻
Iodide of 1H-pyrrolo[1,2-
a]benzimidazolium,
4-[4-[(acetylamino)sulfonyl]-
butyl]-6,7-dichloro-3-[(3-
ethyl-2-selenazolidinylidene)-
ethylidene]-2,3-dihydro

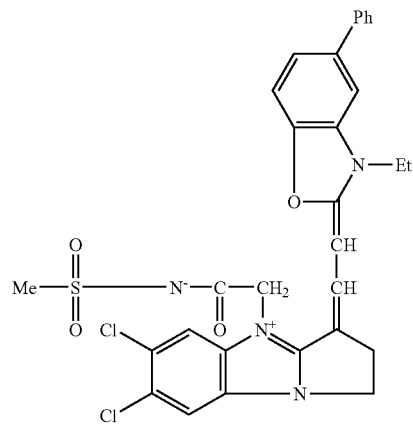

Inner salt of pyrido[1,2-
a]benzimidazolium,
7,8-dichloro-4-[(3-ethyl-
5-phenyl-2(3H)-
benzoxazolylidene)ethylidene]-
1,2,3,4-tetrahydro-5-
[2-[(methylsulfonyl)amino]-
2-oxoethyl]

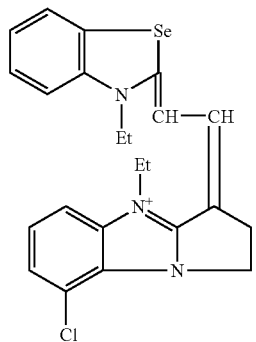

•I⁻
Iodide of 1H-pyrrolo[1,2-
a]benzimidazolium, 8-chloro-
4-ethyl-3-[(3-ethyl-2(3H)-
benzoselenazolylidene)-
ethylidene]-2,3-dihydro

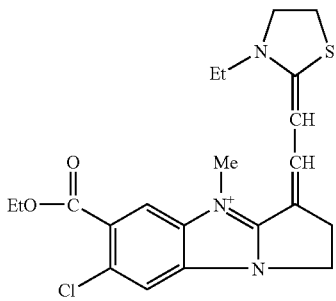

Iodide of 1H-pyrrolo[1,2-a]benzimidazolium, 7-chloro-6-(ethoxycarbonyl)-3-[(3-ethyl-2-thiazolidinylidene)-ethylidene]-2,3-dihydro-4-methyl

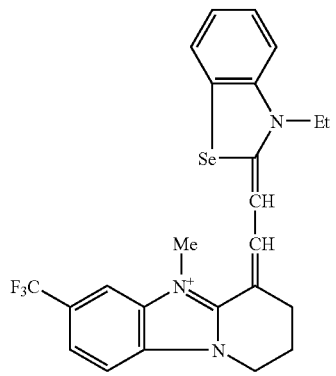

Iodide of pyrido[1,2-a]benzimidazolium, 4-[(3-ethyl-2(3H)-benzoselenazolylidene)-ethylidene]-1,2,3,4-tetrahydro-5-methyl-7-(trifluoromethyl)

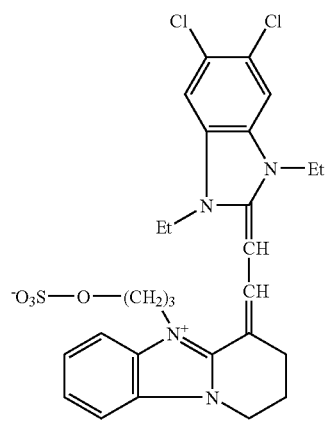

Inner salt of pyrido[1,2-a]benzimidazolium, 4-[(5,6-dichloro-1,3-diethyl-1,3-dihydro-2H-benzimidazol-2-ylidene)ethylidene]-1,2,3,4-tetrahydro-5-[3-sulfooxy)propyl]

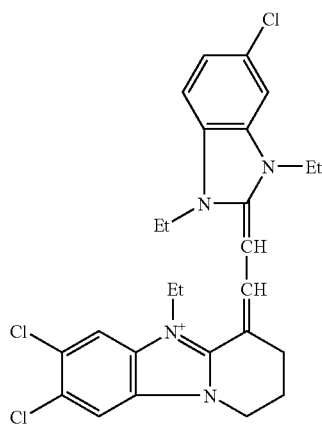
•I-
Iodide of
pyrido[1,2-a]benzimidazolium,
7,8-dichloro-4-[(5-chloro-
1,3-diethyl-1,3-dihydro-2H-
benzimidazol-2-ylidene)-
ethylidene]-5-ethyl-1,2,3,4-
tetrahydro
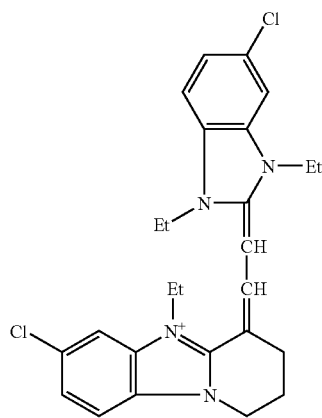
•I-
Iodide of pyrido[1,2-
a]benzimidazolium, 7-chloro-
4-[(5-chloro-1,3-diethyl-
1,3-dihydro-2H-benzimidazol-
2-ylidene)ethylidene]-
5-ethyl-1,2,3,4-tetrahydro

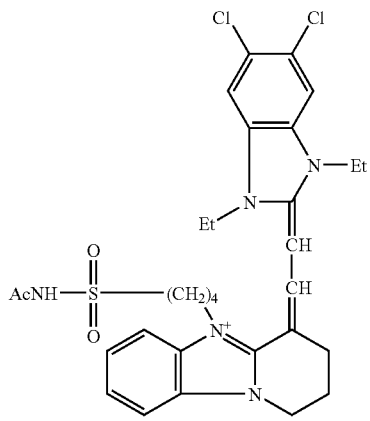

•I-
Iodide of
pyrido[1,2-a]benzimidazolium,
5-[4-[(acetylamino)sulfonyl]-
butyl]-4-[(5,6-dichloro-
1,3-diethyl-1,3-dihydro-2H-
benzimidazol-2-ylidene)-
ethylidene]-1,2,3,4-tetrahydro

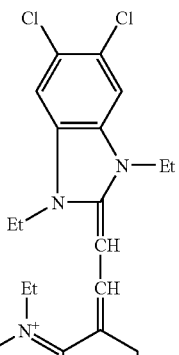

•I-
Iodide of 1H-pyrrolo[1,2-
a]benzimidazolium, 3-[(5,6-
dichloro-1,3-diethyl-1,3-
dihydro-2H-benzimidazol-
2-ylidene)ethylidene]-
4-ethyl-7-fluoro-2,3-dihydro

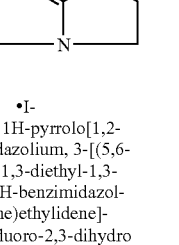

•I-
Iodide of 1H-pyrrolo[1,2-
a]benzimidazolium, 7-chloro-
3-[(5-chloro-1,3-diethyl-1,3-
dihydro-2H-benzimidazol-2-
ylidene)ethylidene]-4-ethyl-
2,3-dihydro

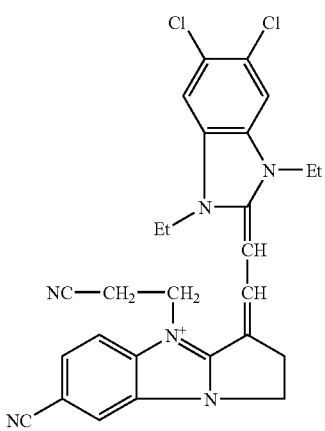

•Br-
Bromide of 1H-pyrrolo[1,2-
a]benzimidazolium, 7-cyano-4-
(2-cyanoethyl)-3-[(5,6-
dichloro-1,3-diethyl-
1,3-dihydro-2H-benzimidazol-
2-ylidene)ethylidene]-
2,3-dihydro

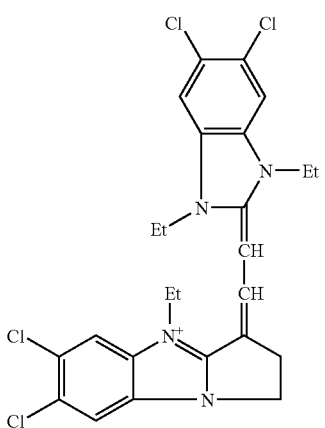

•I⁻
Iodide of 1H-pyrrolo[1,2-a]benzimidazolium, 6,7-dichloro-3-[(5,6-dichloro-1,3-diethyl-1,3-dihydro-2H-benzimidazol-2-ylidene)ethylidene]-4-ethyl-2,3-dihydro

•I⁻
Iodide of 1H-[1,4]oxazino[4,3-a]benzimidazolium, 8-chloro-1-[(5-chloro-1,3-diethyl-1,3-dihydro-2H-benzimidazol-2-ylidene)ethylidene]-10-ethyl-3,4-dihydro

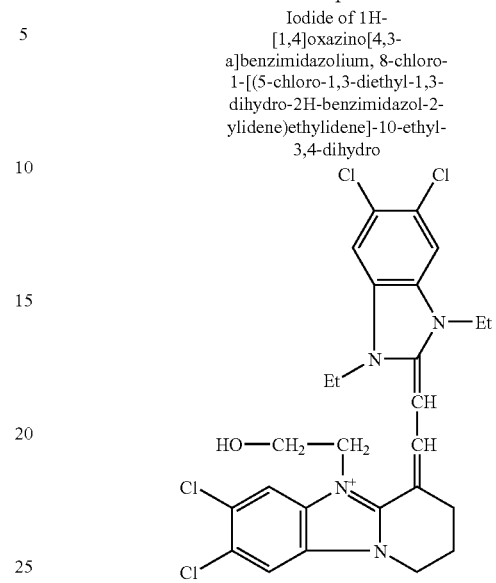

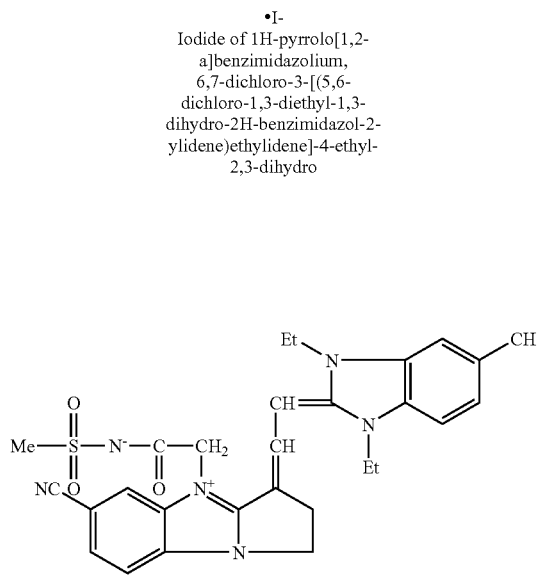

Inner salt of 1H-pyrrolo[1,2-a]benzimidazolium, 6-cyano-3-[(5-cyano-1,3-diethyl-1,3-dihydro-2H-benzimidazol-2-ylidene)ethylidene]-2,3-dihydro-4-[2-[(methylsulfonyl)amino]-2-oxoethyl]

•I⁻
Iodide of pyrido[1,2-a]benzimidazolium, 7,8-dichloro-4-[(5,6-dichloro-1,3-diethyl-1,3-dihydro-2H-benzimidazol-2-ylidene)ethylidene]-1,2,3,4-tetrahydro-5-(2-hydroxyethyl)

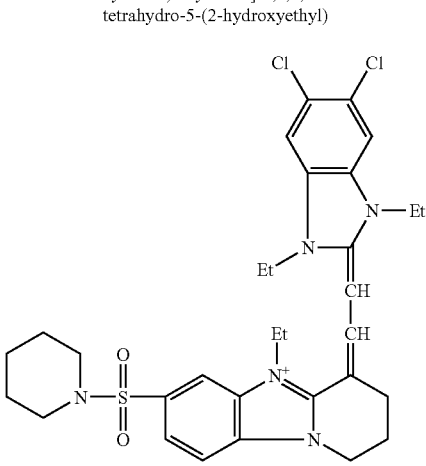

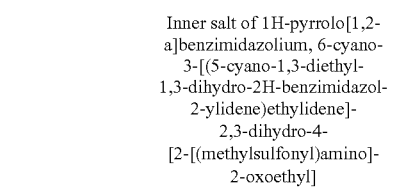

•I⁻
Cl⁻
Salt (for example chloride) of pyrido[1,2-a]benzimidazolium, 4-[(5,6-dichloro-1,3-diethyl-1,3-dihydro-2H-benzimidazol-2-ylidene)ethylidene]-5-ethyl-1,2,3,4-tetrahydro-7-(1-piperidinylsulfonyl)

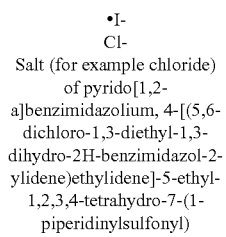

-continued

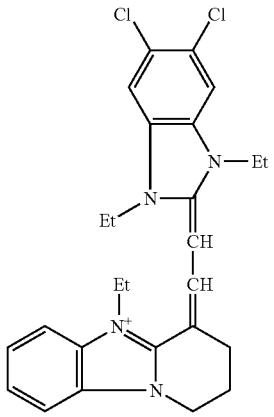

•I-
Iodide of pyrido[1,2-a]benzimidazolium, 4-[(5,6-dichloro-1,3-diethyl-1,3-dihydro-2H-benzimidazol-2-ylidene)ethylidene]-5-ethyl-1,2,3,4-tetrahydro

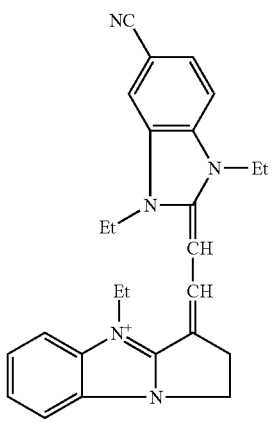

•I-
Iodide of 1H-pyrrolo[1,2-a]benzimidazolium, 3-[(5-cyano-1,3-diethyl-1,3-dihydro-2H-benzimidazol-2-ylidene)ethylidene]-4-ethyl-2,3-dihydro

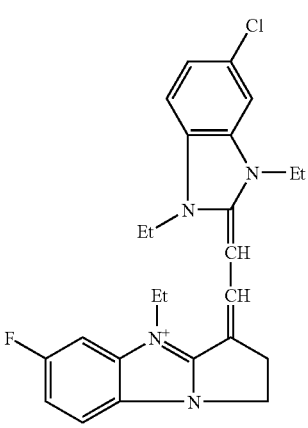

•I-

Iodide of 1H-pyrrolo[1,2-a]benzimidazolium, 3-[(5-chloro-1,3-diethyl-1,3-dihydro-2H-benzimidazol-2-ylidene)ethylidene]-4-ethyl-6-fluoro-2,3-dihydro

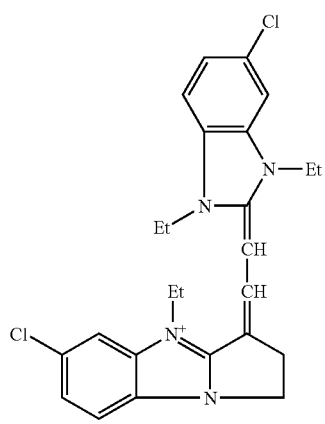

•I-
Iodide of 1H-pyrrolo[1,2-a]benzimidazolium, 6-chloro-3-[(5-chloro-1,3-diethyl-1,3-dihydro-2H-benzimidazol-2-ylidene)ethylidene]-4-ethyl-2,3-dihydro

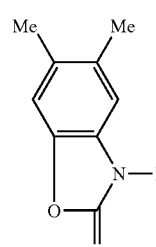

•I-
Iodide of 1H-[1,4]oxazino[4,3-a]benzimidazolium, 7,8-dichloro-10-ethyl-1-[(3-ethyl-5,6-dimethyl-2(3H)-berizoxazolylidene)ethylidene]-3,4-dihydro -continued

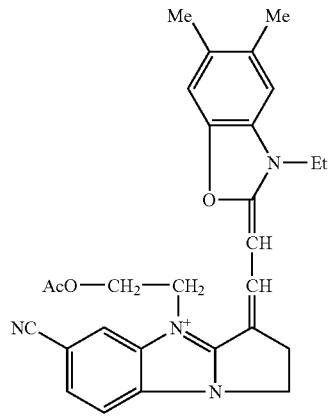

•I-
Iodide of 1H-pyrrolo[1,2-a]benzimidazolium, 4-[2-(acetyloxy)ethyl]-6-cyano-3-[(3-ethyl-5,6-dimethyl-2(3H)-benzoxazolylidene)-ethylidene]-2,3-dihydro

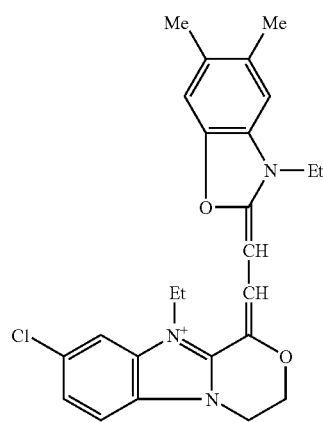

•I-
Iodide of 1H-[1,4]oxazino[4,3-a]benzimidazolium, 8-chloro-10-ethyl-1-[(3-ethyl-5,6-dimethyl-2(3H)-benzoxazolylidene)-ethylidene]-3,4-dihydro -continued

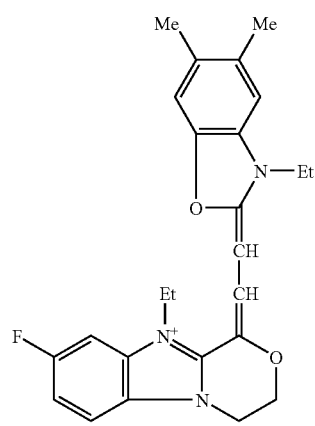

•I-
Iodide of pyrido[1,2-a]benzimidazolium, 5-ethyl-4-[(3-ethyl-5,6-dimethyl-2(3H)-benzoxazolylidene)-ethylidene]-7-fluoro-1,2,3,4-tetrahydro

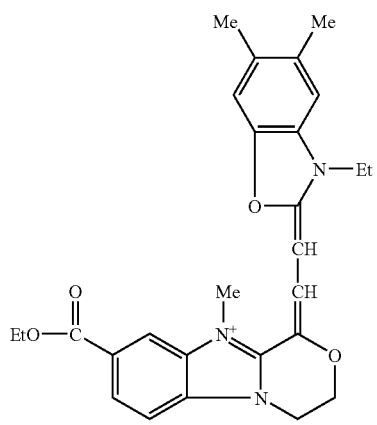

•I-
Iodide of 1H-pyrrolo[1,2-a]benzimidazolium, 6-(ethoxycarbonyl)-3-[(3-ethyl-5,6-dimethyl-2(3H)-benzoxazolylidene)ethylidene]-2,3-dihydro-4-methyl -continued

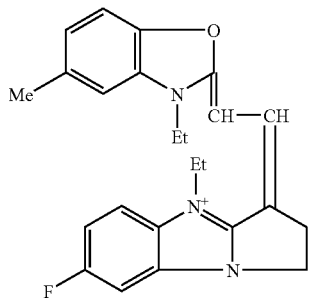

ClO4−
Perchlorate of
1H-pyrrolo[1,2-
a]benzimidazolium, 4-ethyl-
3-[(3-ethyl-5-methyl-2(3H)-
benzoxazolylidene)-
ethylidene]-7-fluoro-
2,3-dihydro

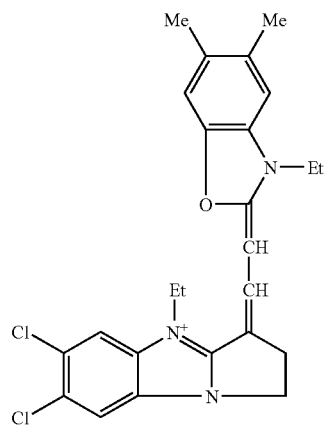

•I−
Iodide of 1H-pyrrolo[1,2-
a]benzimidazolium,
6,7-dichloro-4-ethyl-3-
[(3-ethyl-5,6-dimethyl-2(3H)-
benzoxazolylidene)-
ethylidene]-2,3-dihydro

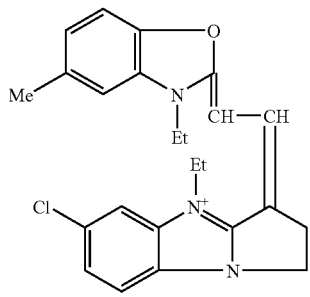

•I−
Iodide of 1H-pyrrolo[1,2-
a]benzimidazolium, 6-chloro-
4-ethyl-3-[(3-ethyl-5-methyl-
2(3H)-benzoxazolylidene)-
ethylidene]-2,3-dihydro -continued

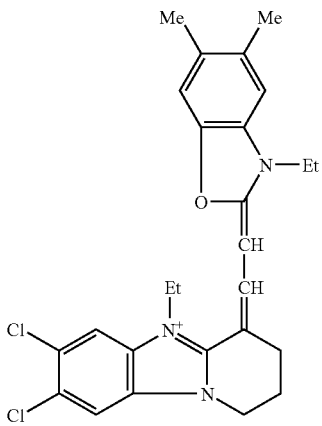

•I−
Iodide of pyrido[1,2-
a]benzimidazolium,
7,8-dichloro-5-ethyl-4-
[(3-ethyl-5,6-dimethyl-2(3H)-
benzoxazolylidene)ethylidene]-
1,2,3,4-tetrahydro

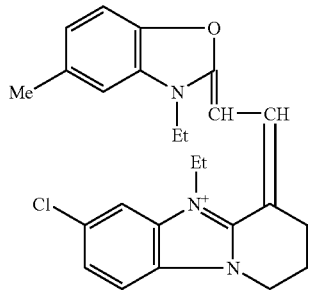

•I−
Iodide of pyrido[1,2-
a]benzimidazolium, 7-chloro-
5-ethyl-4-[(3-ethyl-5-methyl-
2(3H)-benzoxazolylidene)-
ethylidene]-1,2,3,4-
tetrahydro

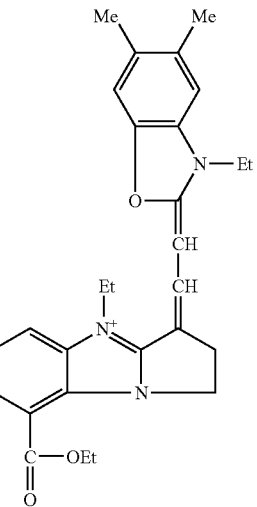

-continued

•I⁻
Iodide of 1H-pyrrolo[1,2-a]benzimidazolium, 8-(ethoxycarbonyl)-3-[(3-ethyl-5,6-dimethyl-2(3H)-benzoxazolylidene)ethylidene]-2,3-dihydro-4-methyl

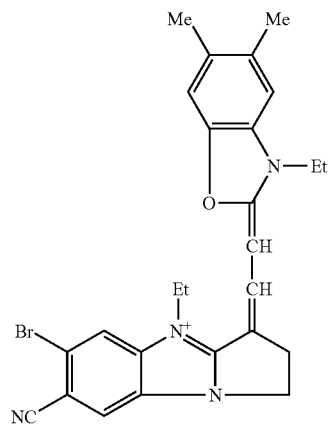

•I⁻
Iodide of 1H-pyrrolo[1,2-a]benzimidazolium, 6-bromo-7-cyano-4-ethyl-3-[(3-ethyl-5,6-dimethyl-2(3H)-benzoxazolylidene)ethylidene]-2,3-dihydro

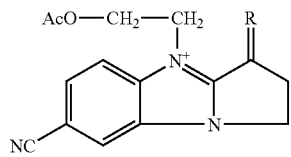

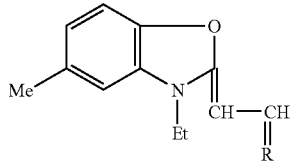

ClO₄⁻
Perchlorate of 1H-pyrrolo[1,2-a]benzimidazolium, 4-[2-(acetyloxy)ethyl]-7-cyano-3-[(3-ethyl-5-methyl-2(3H)-benzoxazolylidene)-ethylidene]-2,3-dihydro

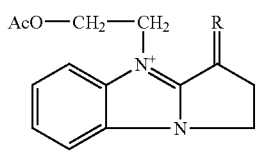

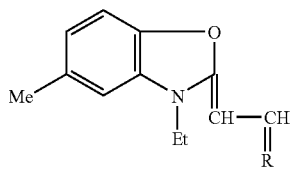

-continued

ClO₄⁻
Perchlorate of 1H-pyrrolo[1,2-a]benzimidazolium, 4-[2-(acetyloxy)ethyl]-3-[(3-ethyl-5-methyl-2(3H)-benzoxazolylidene)ethylidene]-2,3-dihydro

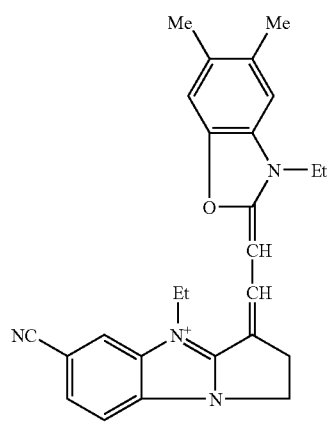

•I⁻
Iodide of 1H-pyrrolo[1,2-a]benzimidazolium, 6-cyano-4-ethyl-3-[(3-ethyl-5,6-dimethyl-2(3H)-benzoxazolylidene)-ethylidene]-2,3-dihydro

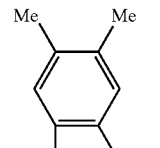

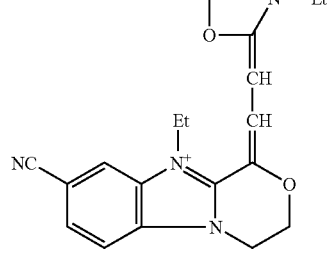

•I⁻
Iodide of 1H-[1,4]oxazino[4,3-a]benzimidazolium, 8-cyano-10-ethyl-1-[(3-ethyl-5,6-dimethyl-2(3H)-benzoxazolylidene)-ethylidene]-3,4-dihydro -continued

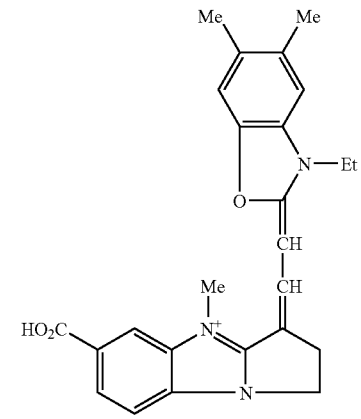

•I⁻
Iodide of 1H-pyrrolo[1,2-a]benzimidazolium, 6-carboxy-3-[(3-ethyl-5,6-dimethyl-2(3H)-benzoxazolylidene)-ethylidene]-2,3-dihydro-4-methyl

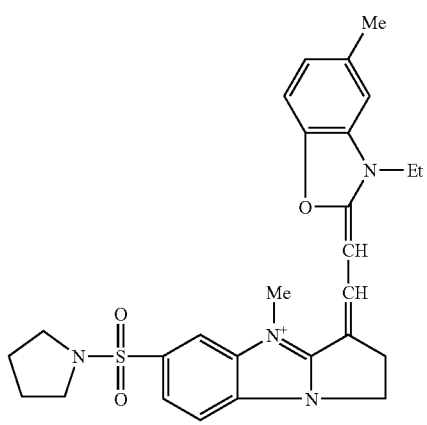

•I⁻
Iodide of 1H-pyrrolo[1,2-a]benzimidazolium, 3-[(3-ethyl-5-methyl-2(3H)-benzoxazolylidene)ethylidene]-2,3-dihydro-4-methyl-6-(1-pyrrolidinylsulfonyl)

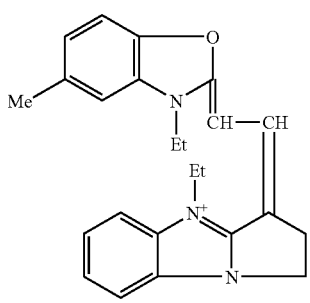

ClO₄⁻
Perchlorate of 1H-pyrrolo[1,2-a]benzimidazolium, 4-ethyl-3-[(3-ethyl-5-methyl-2(3H)-benzoxazolylidene)ethylidene]-2,3-dihydro

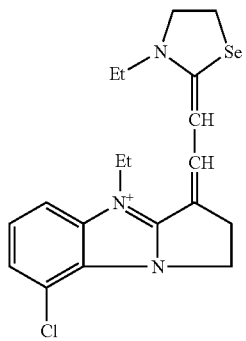

•I⁻
Iodide of 1H-pyrrolo[1,2-a]benzimidazolium, 8-chloro-4-ethyl-3-[(3-ethyl-2-selenazolidinylidene)-ethylidene]-2,3-dihydro

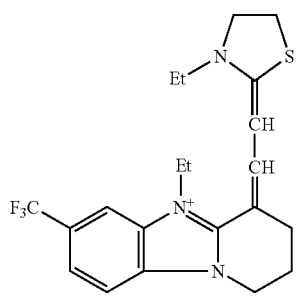

•I⁻
Iodide of pyrido[1,2-a]benzimidazolium, 5-ethyl-4-[(3-ethyl-2-thiazolidinylidene)-ethylidene]-1,2,3,4-tetrahydro-7-(trifluoromethyl)

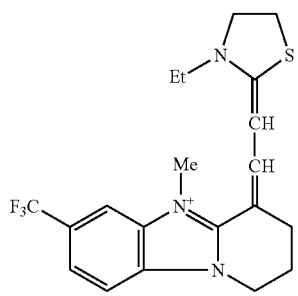

•I⁻
Iodide of pyrido[1,2-a]benzimidazolium, 4-[(3-ethyl-2-thiazolidinylidene)-ethylidene]-1,2,3,4-tetrahydro-5-methyl-7-(trifluoromethyl)

-continued

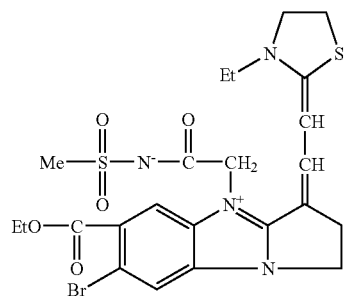

Inner salt of 1H-pyrrolo[1,2-
a]benzimidazolium, 7-bromo-6-
(ethoxycarbonyl)-3-[(3-ethyl-
2-thiazolidinylidene)-
ethylidene]-2,3-dihydro-4-[2-
[(methylsulfonyl)amino]-
2-oxoethyl]-

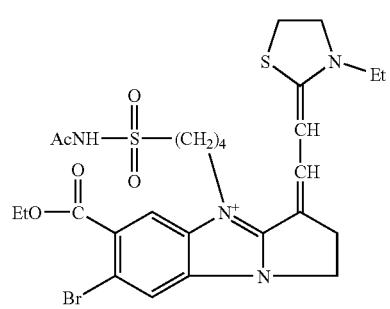

•Br-
Bromide of 1H-pyrrolo[1,2-
a]benzimidazolium,
4-[4-[(acetylamino)sulfonyl]-
butyl]-7-bromo-6-
(ethoxycarbonyl)-3-[(3-ethyl-
2-thiazolidinylidene)-
ethylidene]-2,3-dihydro

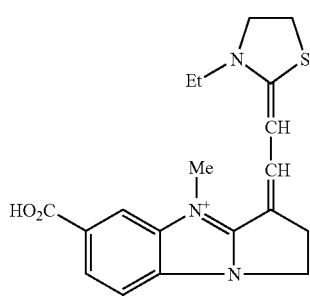

•I-
Iodide of 1H-pyrrolo[1,2-
a]benzimidazolium, 6-carboxy-
3-[(3-ethyl-2-
thiazolidinylidene)-
ethylidene]-2,3-dihydro-
4-methyl -continued

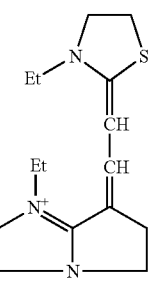

•I-
Iodide of 1H-pyrrolo[1,2-
a]benzimidazolium, 6-cyano-
4-ethyl-3-[(3-ethyl-
2-thiazolidinylidene)-
ethylidene]-2,3-dihydro

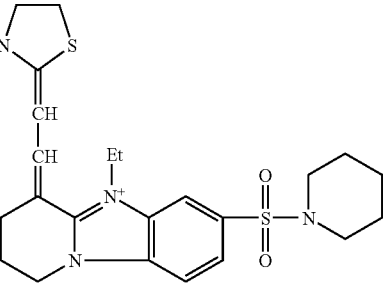

•I-
Iodide of pyrido[1,2-
a]benzimidazolium, 5-ethyl-
4-[(3-ethyl-2-
thiazolidinylidene)-
ethylidene]-1,2,3,4-
tetrahydro-7-
(1-piperidinylsulfonyl)

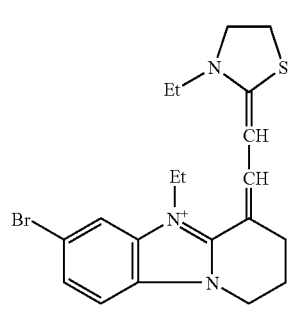

•I-
Iodide of pyrido[1,2-
a]benzimidazolium, 7-bromo-5-
ethyl-4-[(3-ethyl-2-
thiazolidinylidene)ethylidene]-
1,2,3,4-tetrahydro

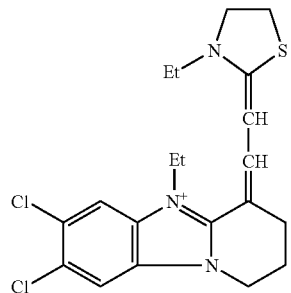

•I-

Iodide of pyrido[1,2-a]benzimidazolium, 7,8-dichloro-5-ethyl-4-[(3-ethyl-2-thiazolidinylidene)-ethylidene]-1,2,3,4-tetrahydro

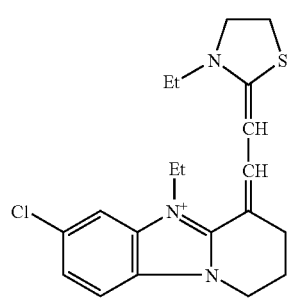

•I-

Iodide of pyrido[1,2-a]benzimidazolium, 7-chloro-5-ethyl-4-[(3-ethyl-2-thiazolidinylidene)-ethylidene]-1,2,3,4-tetrahydro

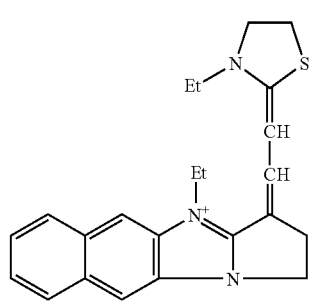

•I-

Iodide of 1H-naphtho[2,3-d]pyrrolo[1,2-a]imidazolium, 4-ethyl-3-[(3-ethyl-2-thiazolidinylidene)-ethylidene]-2,3-dihydro

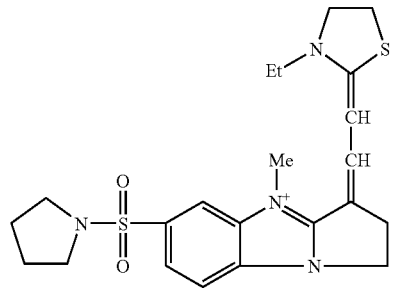

•I-

Iodide of 1H-pyrrolo[1,2-a]benzimidazolium, 3-[(3-ethyl-2-thiazolidinylidene)ethylidene]-2,3-dihydro-4-methyl-6-(1-pyrrolidinylsulfonyl)

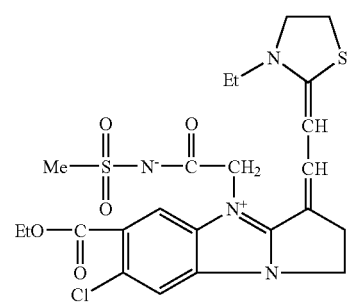

Inner salt of 1H-pyrrolo[1,2-a]benzimidazolium, 7-chloro-6-(ethoxycarbonyl)-3-[(3-ethyl-2-thiazolidinylidene)-ethylidene]-2,3-dihydro-4-[2-[(methylsulfonyl)amino]-2-oxoethyl]

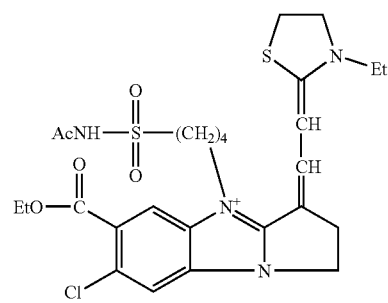

•Br-

Bromide of 1H-pyrrolo[1,2-a]benzimidazolium, 4-[4-[(acetylamino)sulfonyl]-butyl]-7-chloro-6-(ethoxycarbonyl)-3-[(3-ethyl-2-thiazolidinylidene)-ethylidene]-2,3-dihydro -continued

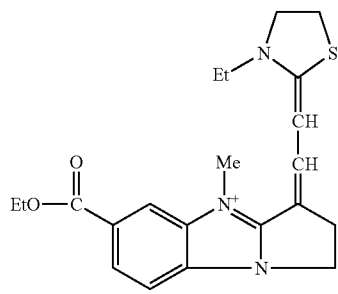

•I⁻

Iodide of 1H-pyrrolo[1,2-a]benzimidazolium, 6-(ethoxycarbonyl)-3-[(3-ethyl-2-thiazolidinylidene) ethylidene]-2,3-dihydro-4-methyl

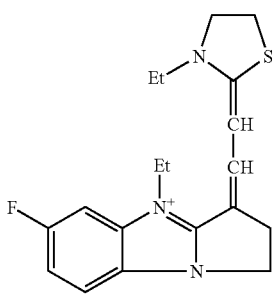

•I⁻

Iodide of 1H-pyrrolo[1,2-a]benzimidazolium, 4-ethyl-3-[(3-ethyl-2-thiazolidinylidene]-6-fluoro-2,3-dihydro

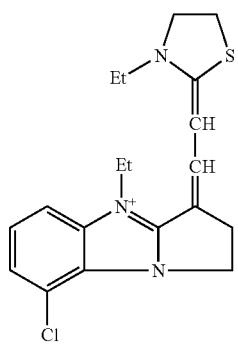

•I⁻

Iodide of 1H-pyrrolo[1,2-a]benzimidazolium, 8-chloro-4-ethyl-3-[(3-ethyl-2-thiazolidinylidene)-ethylidene]-2,3-dihydro -continued

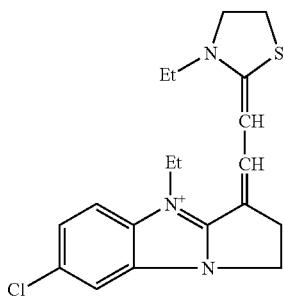

•I⁻

Iodide of 1H-pyrrolo[1,2-a]benzimidazolium, 7-chloro-4-ethyl-3-[(3-ethyl-2-thiazolidinylidene)-ethylidene]-2,3-dihydro

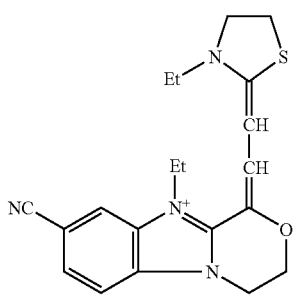

•I⁻

Iodide of 1H-[1,4]oxazino[4,3-a]benzimidazolium, 8-cyano-10-ethyl-1-[(3-ethyl-2-thiazolidinylidene)-ethylidene]-3,4-dihydro

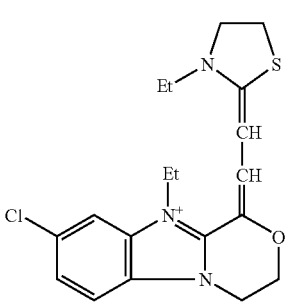

•I⁻

Iodide of 1H-[1,4]oxazino[4,3-a]benzimidazolium, 8-chloro-10-ethyl-1-[(3-ethyl-2-thiazolidinylidene)-ethylidene]-3,4-dihydro

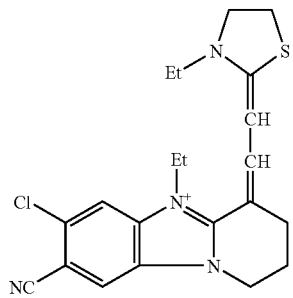

•I-
Iodide of pyrido[1,2-a]benzimidazolium, 7-chloro-8-cyano-5-ethyl-4-[(3-ethyl-2-thiazolidinylidene)-ethylidene]-1,2,3,4-tetrahydro

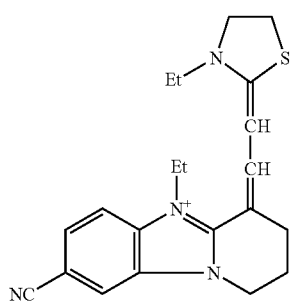

•I-
Iodide of pyrido[1,2-a]benzimidazolium, 8-cyano-5-ethyl-4-[(3-ethyl-2-thiazolidinylidene)-ethylidene]-1,2,3,4-tetrahydro

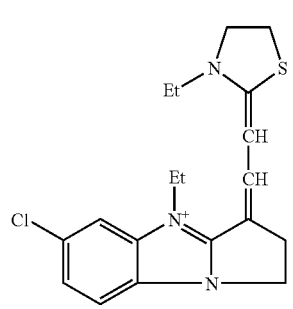

•I-
Iodide of 1H-pyrrolo[1,2-a]benzimidazolium, 6-chloro-4-ethyl-3[(3-ethyl-2-thiazolidinylidene)-ethylidene]-2,3-dihydro

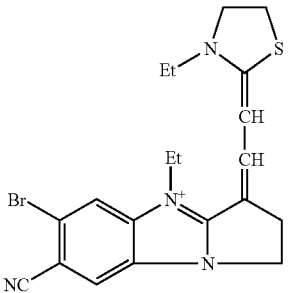

•I-
Iodide of 1H-pyrrolo[1,2-a]benzimidazolium, 6-bromo-7-cyano-4-ethyl-3-[(3-ethyl-2-thiazolidinylidene)-ethylidene]-2,3-dihydro

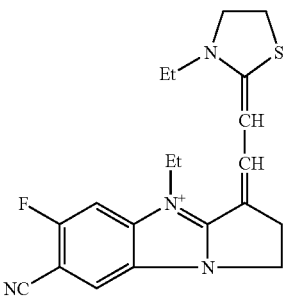

•I-
Iodide of 1H-pyrrolo[1,2-a]benzimidazolium, 7-cyano-4-ethyl-3-[(3-ethyl-2-thiazolidinylidene)-ethylidene]-6-fluoro-2,3-dihydro

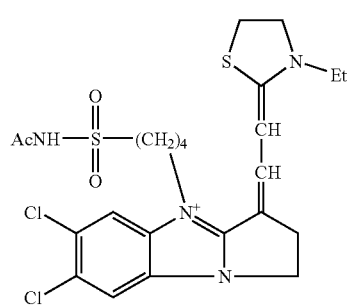

•Br-
Bromide of 1H-pyrrolo[1,2-a]benzimidazolium, 4-[4-[(acetylamino)sulfonyl]-butyl]-6,7-dichloro-3-[(3-ethyl-2-selenazolidinylidene)-ethylidene]-2,3-dihydro -continued

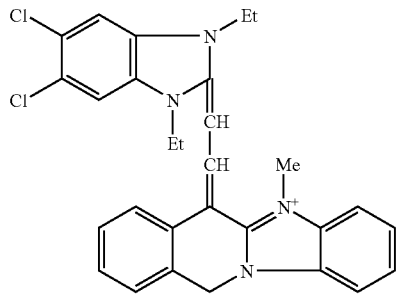

•I⁻
Iodide of benzimidazo[1,2-b]isoquinolinium, 6-[(5,6-dichloro-1,3-diethyl-1,3-dihydro-2H-benzimidazol-2-ylidene)ethylidene]-6,11-dihydro-5-methyl

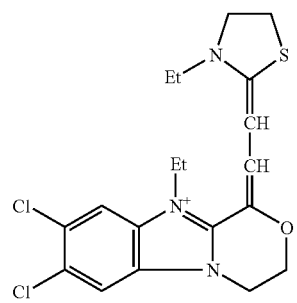

•I⁻
Iodide of 1H-[1,4]oxazino[4,3-a]benzimidazolium, 7,8-dichloro-10-ethyl-1-[(3-ethyl-2-thiazolidinylidene)-ethylidenel-3,4-dihydro

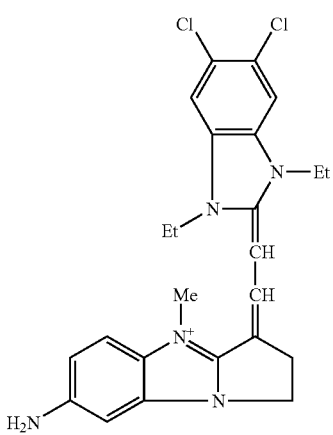

•I⁻
Iodide of 1H-pyrrolo[1,2-a]benzimidazolium, 7-amino-3-[(5,6-dichloro-1,3-diethyl-1,3-dihydro-2H-benzimidazol-2-ylidene)ethylidene]-2,3-dihydro-4-methyl -continued

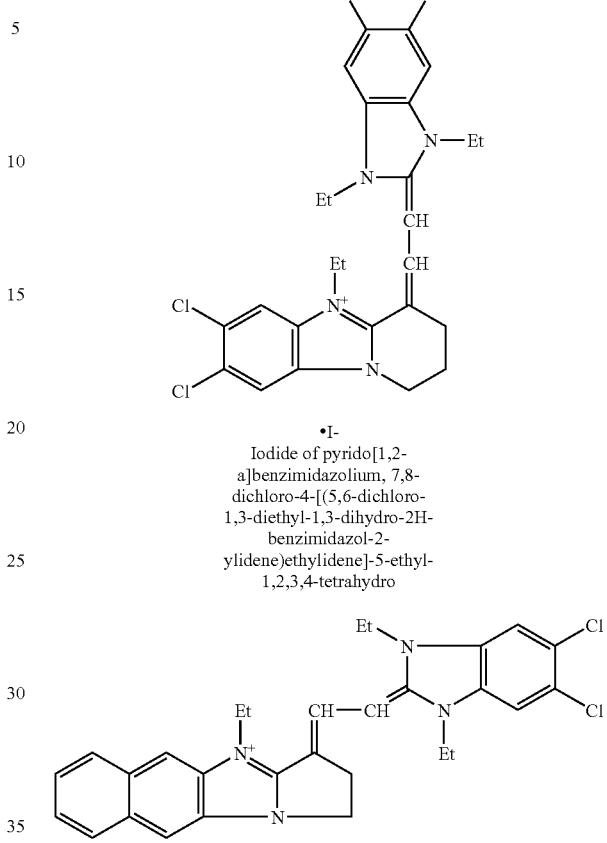

•I⁻
Iodide of pyrido[1,2-a]benzimidazolium, 7,8-dichloro-4-[(5,6-dichloro-1,3-diethyl-1,3-dihydro-2H-benzimidazol-2-ylidene)ethylidene]-5-ethyl-1,2,3,4-tetrahydro

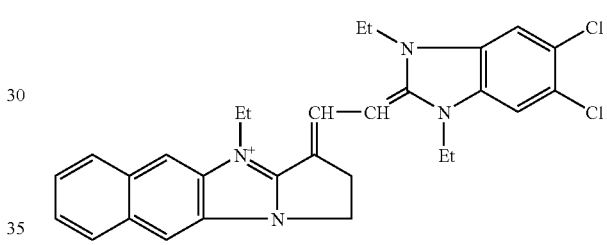

•I⁻
Iodide of 1H-naphtho[2,3-d]pyrrolo[1,2-a]imidazolium, 3-[(5,6-dichloro-1,3-diethyl-1,3-dihydro-2H-benzimidazol-2-ylidene)ethylidene]-4-ethyl-2,3-dihydro

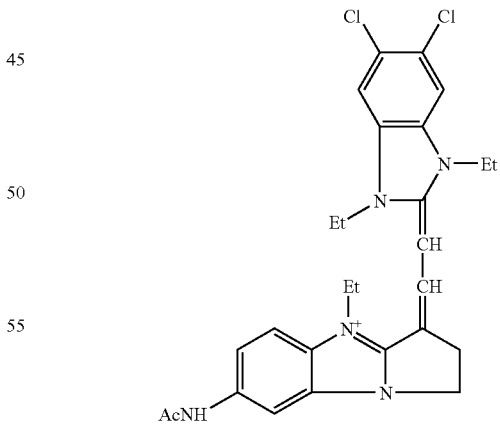

•I⁻
Iodide of 1H-pyrrolo[1,2-a]benzimidazolium, 7-(acetylamino)-3-[(5,6-dichloro-1,3-diethyl-1,3-dihydro-2H-benzimidazol-2-ylidene)ethylidene]-4-ethyl-2,3-dihydro

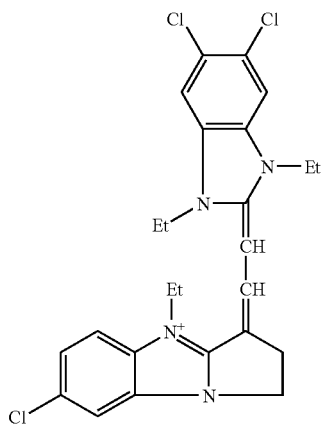

•I⁻
Iodide of 1H-pyrrolo[1,2-
a]benzimidazolium, 7-chloro-
3-[(5,6-dichloro-1,3-diethyl-
1,3-dihydro-2H-benzimidazol-
2-ylidene)ethylidene]-4-
ethyl-2,3-dihydro

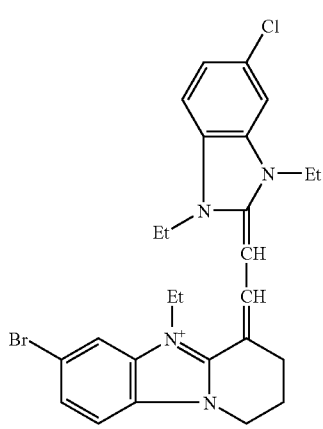

•I⁻
Iodide of pyrido[1,2-
a]benzimidazolium, 7-bromo-4-
[(5-chloro-1,3-diethyl-1,3-
dihydro-2H-benzimidazol-2-
ylidene)ethylidene]-5-ethyl-
1,2,3,4-tetrahydro

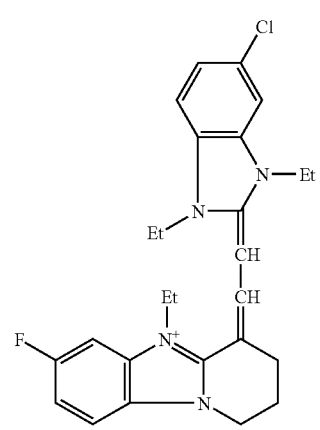

•I⁻
Iodide of pyrido[1,2-
a]benzimidazolium, 4-[(5-
chloro-1,3-diethyl-1,3-
dihydro-2H-benzimidazol-2-
ylidene)ethylidene]-5-ethyl-
7-fluoro-1,2,3,4-tetrahydro

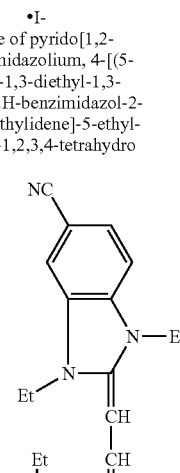

•I⁻
Iodide of 1H-pyrrolo[1,2-
a]benzimidazolium, 3-[(5-
cyano-1,3-diethyl-1,3-
dihydro-2H-benzimidazol-2-
ylidene)ethylidene]-4-ethyl-
7-fluoro-2,3-dihydro

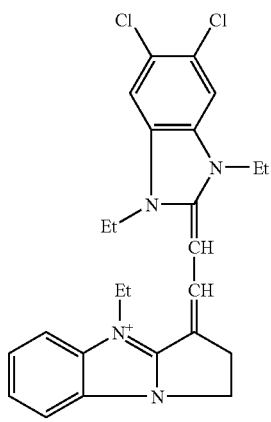

•I⁻
Iodide of 1H-pyrrolo[1,2-
a]benzimidazolium, 3-[(5,6-
dichloro-1,3-diethyl-1,3-
dihydro-2H-benzimidazol-2-
ylidene)ethylidene]-4-ethyl-
2,3-dihydro

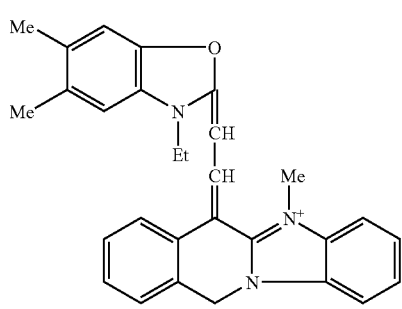

-continued

Iodide of benzimidazo[1,2-b]isoquinolinium, 6-[(3-ethyl-5,6-dimethyl-2(3H)-benzoxazolylidene)ethylidene]-6,11-dihydro-5-methyl

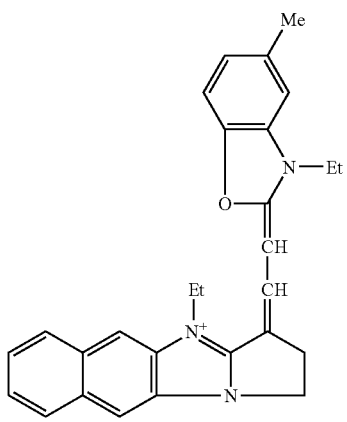

•I-
Iodide of 1H-naphtho[2,3-d]pyrrolo[1,2-a]imidazolium, 4-ethyl-3-[(3-ethyl-5-methyl-2(3H)-benzoxazolylidene)-ethylidene]-2,3-dihydro

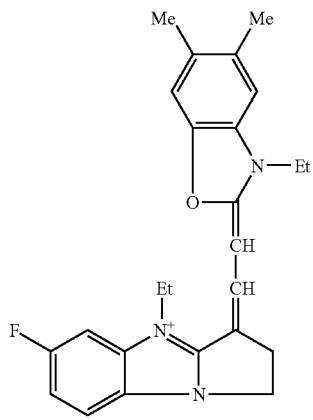

•I-
Iodide of 1H-pyrrolo[1,2-a]benzimidazolium, 4-ethyl-3-[(3-ethyl-5,6-dimethyl-2(3H)-benzoxazolylidene) ethylidene]-6-fluoro-2,3-dihydro

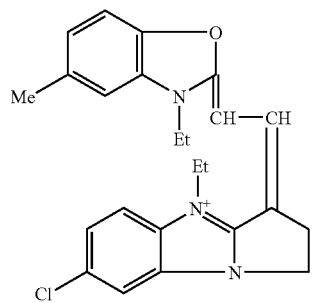

•I-

-continued

Iodide of 1H-pyrrolo[1,2-a]benzimidazolium, 7-chloro-4-ethyl-3-[(3-ethyl-5-methyl-2(3H)-benzoxazolylidene)-ethylidene]-2,3-dihydro

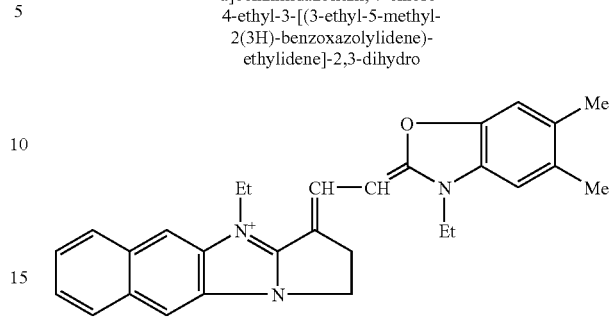

•I-
Iodide of 1H-naphtho[2,3-d]pyrrolo[1,2-a]imidazolium, 4-ethyl-3-[(3-ethyl-5,6-dimethyl-2(3H)-benzoxazolylidene)-ethylidene]-2,3-dihydro

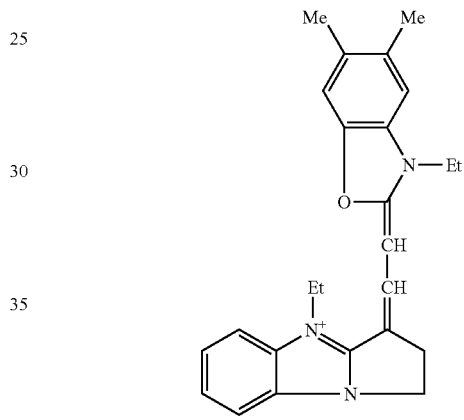

•I-
Iodide of 1H-pyrrolo[1,2-a]benzimidazolium, 4-ethyl-3-[(3-ethyl-5,6-dimethyl-2(3H)-benzoxazolylidene)-ethylidene]-2,3-dihydro

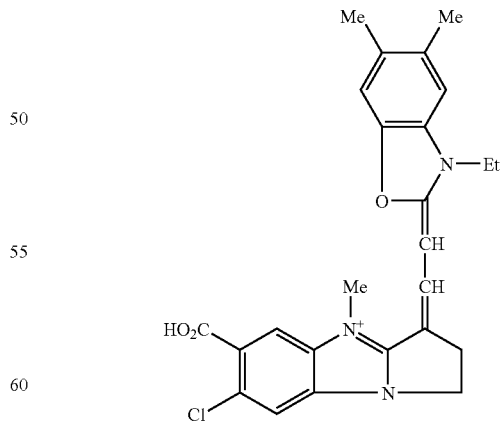

•I-
Iodide of 1H-pyrrolo[1,2-a]benzimidazolium, 6-carboxy-7-chloro-3-[(3-ethyl-5,6-dimethyl-2(3H)-

-continued benzoxazolylidene)-
ethylidene]-2,3-dihydro-
4-methyl

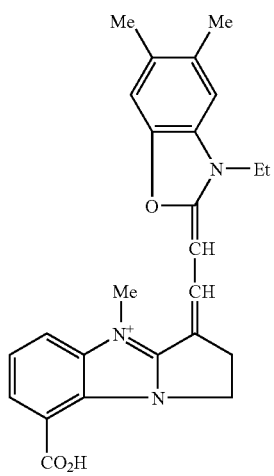

•I-
Iodide of 1H-pyrrolo[1,2-
a]benzimidazolium, 8-carboxy-
3-[(3-ethyl-5,6-dimethyl-
2(3H)-benzoxazolylidene)-
ethylidene]-2,3-dihydro-
4-methyl

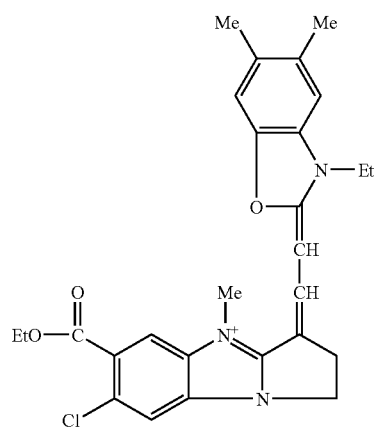

•I-
Iodide of 1H-pyrrolo[1,2-
a]benzimidazolium, 7-chloro-6-
(ethoxycarbonyl)-3-[(3-ethyl-
5,6-dimethyl-2(3H)-
benzoxazolylidene)ethylidene]-
2,3-dihydro-4-methyl

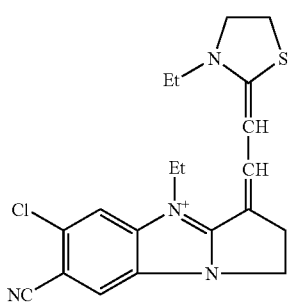

-continued

•I-
Iodide of 1H-pyrrolo[1,2-
a]benzimidazolium, 6-chloro-
7-cyano-4-ethyl-3-[(3-ethyl-
2-thiazolidinylidene)-
ethylidene]-2,3-dihydro

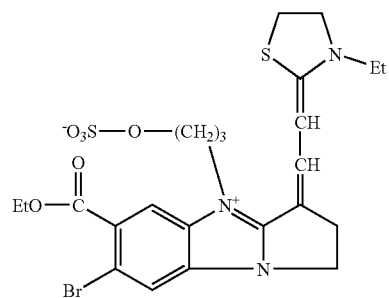

Inner salt of 1H-pyrrolo[1,2-
a]benzimidazolium, 7-bromo-6-
(ethoxycarbonyl)-3-[(3-ethyl-
2-thiazolidinylidene)-
ethylidene]-2,3-dihydro-4-[3-
(sulfooxy)propyl]

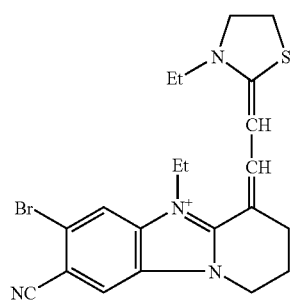

•I-
Iodide of pyrido[1,2-
a]benzimidazolium, 7-bromo-
8-cyano-5-ethyl-4-[(3-ethyl-
2-thiazolidinylidene)-
ethylidene]-1,2,3,4-
tetrahydro

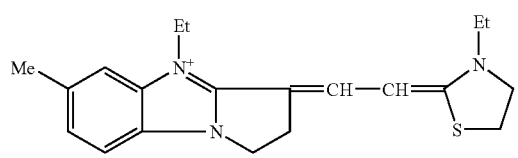

•I-
Iodide of 1H-pyrrolo[1,2-
a]benzimidazolium, 4-ethyl-3-
[(3-ethyl-2-
thiazolidinylidene)ethylidene]-
2,3-dihydro-6-methyl -continued

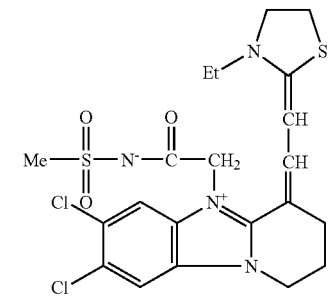

Inner salt of pyrido[1,2-a]benzimidazolium, 7,8-dichloro-4-[(3-ethyl-2-thiazolidinylidene)ethylidene]-1,2,3,4-tetrahydro-5-[2-[(methylsulfonyl)amino]-2-oxoethyl]-

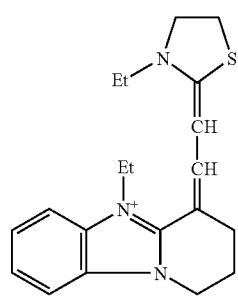

•I⁻
Iodide of pyrido[1,2-a]benzimidazolium, 5-ethyl-4-[(3-ethyl-2-thiazolidinylidene)-ethylidene]-1,2,3,4-tetrahydro

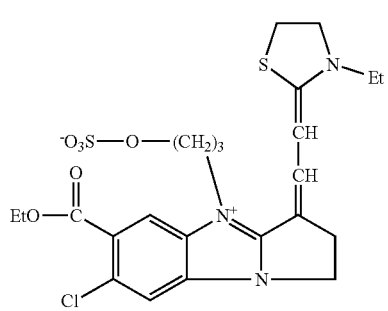

Inner salt of 1H-pyrrolo[1,2-a]benzimidazolium, 7-chloro-6-(ethoxycarbonyl)-3-[(3-ethyl-2-thiazolidinylidene)-ethylidene]-2,3-dihydro-4-[3-sulfooxy)propyl -continued

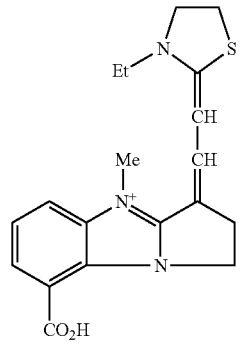

•I⁻
Iodide of 1H-pyrrolo[1,2-a]benzimidazolium, 8-carboxy-3-[(3-ethyl-2-thiazolidinylidene)-ethylidene]-2,3-dihydro-4-methyl

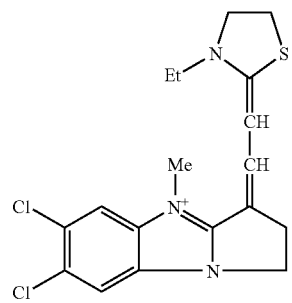

•I⁻
Iodide of 1H-pyrrolo[1,2-a]benzimidazolium, 6,7-dichloro-4-ethyl-3-[(3-ethyl-2-thiazolidinylidene)-ethylidene]-2,3-dihydro

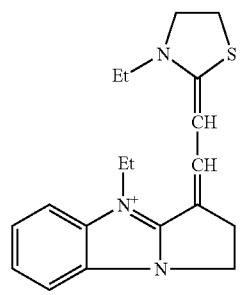

•I⁻
Iodide of 1H-pyrrolo[1,2-a]benzimidazolium, 4-ethyl-3-[(3-ethyl-2-thiazolidinylidene)-ethylidene]-2,3-dihydro -continued

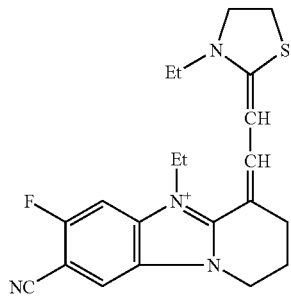

•I-
Iodide of pyrido[1,2-a]benzimidazolium, 8-cyano-5-ethyl-4-[(3-ethyl-2-thiazolidinylidene)-ethylidene]-7-fluoro-1,2,3,4-tetrahydro

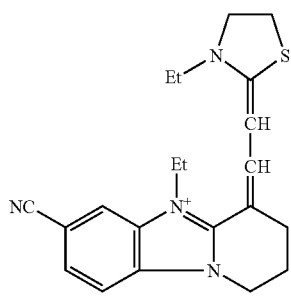

•I-
Iodide of pyrido[1,2-a]benzimidazolium, 7-cyano-5-ethyl-4-[(3-ethyl-2-thiazolidinylidene)ethylidene]-1,2,3,4-tetrahydro

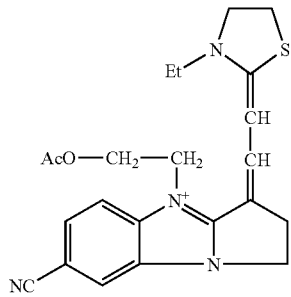

Perchlorate of 1H-pyrrolo[1,2-a]benzimidazolium, 4-[2-(acetyloxy)ethyl]-7-cyano-3-[(3-ethyl-2-thiazolidinylidene)-ethylidene]-2,3-dihydro The nature of the counterion is not critical. Thus, the anions mentioned in this table above are only given by way of example.

The direct dye(s) of formula (I) represent more particularly from 0.01 to 20% by weight, preferably from 0.1 to 5% by weight relative to the total weight of the composition.

The cosmetically acceptable medium generally consists of water or of a mixture of water and at least one organic solvent.

As organic solvent, there may be mentioned for example linear or branched $C_1$-$C_4$ alkanols such as ethanol and isopropanol; glycerol; glycols and glycol ethers such as 2-butoxyethanol, propylene glycol, dipropylene glycol, propylene glycol monomethyl ether, diethylene glycol monoethyl ether and monomethyl ether, and aromatic alcohols such as benzyl alcohol or phenoxyethanol, analogous products and mixtures thereof.

The solvent(s) may be present in proportions preferably ranging from about 1 to 40% by weight relative to the total weight of the dyeing composition, and more preferably still from about 5 to 30% by weight.

The pH of the composition in accordance with the invention is generally between about 3 and 12, and preferably between about 5 and 11. It may be adjusted to the desired value by means of acidifying or alkalinizing agents customarily used in the field.

Among the acidifying agents, there may be mentioned, by way of example, inorganic or organic acids such as hydrochloric acid, orthophosphoric acid, sulfuric acid, carboxylic acids such as acetic acid, tartaric acid, citric acid, lactic acid, sulfonic acids.

Among the alkalinizing agents, there may be mentioned, by way of example, aqueous ammonia, alkali metal carbonates, alkanolamines such as mono-, di- and triethanolamines and derivatives thereof, sodium or potassium hydroxides and compounds of the following formula (II):

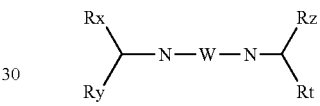

in which W is a propylene residue optionally substituted with a hydroxyl group or a $C_1$-$C_6$ alkyl radical; Rx, Ry, Rz and Rt, which are identical or different, represent a hydrogen atom, a $C_1$-$C_6$ alkyl or $C_1$-$C_6$ hydroxyalkyl radical.

The cosmetic composition may also comprise one or more additional direct dyes of a nonionic, cationic or anionic, and preferably cationic or nonionic nature, or combinations thereof.

Generally, these direct dyes are chosen from nitrobenzene dyes, azo, azomethine, methine, anthraquinone, naphthoquinone, benzoquinone, phenothiazine, indigoid, xanthene, phenanthridine and phthalocyanine dyes, those derived from triarylmethane, natural dyes, alone or as mixtures.

It may for example be chosen from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitroparaphenylenediamine,
1-amino-2-nitro-4-(β-hydroxyethyl-)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)-benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene, 2-nitro-4'-hydroxydiphenylamine,
1-amino-2-nitro-4-hydroxy-5-methylbenzene.

The composition used in the context of this first variant may also comprise, in addition to or as a replacement of these nitrobenzene dyes, one or more direct dyes chosen from yellow, green-yellow, blue or purple nitrobenzene dyes, azo dyes, anthraquinone, naphthoquinone or benzoquinone dyes, indigoid dyes or dyes derived from triarylmethane.

These direct dyes may be in particular basic dyes among which there may be mentioned more particularly the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes among which there may be mentioned more particularly the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in patent applications WO 95/01772, WO 95/15144 and EP 714954 and the contents of which form an integral part of the present invention.

Among the additional yellow and green-yellow nitrobenzene direct dyes, there may be mentioned for example the compounds chosen from:

1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene,
4-(β-hydroxyethyl)amino-3-nitrobenzamide.

Among the additional blue or purple nitrobenzene direct dyes, there may be mentioned for example the compounds chosen from:

1-(β-hydroxyethyl)amino-4-N,N-bis(β-hydroxyethyl)-amino-2-nitrobenzene,
1-(γ-hydroxypropyl)amino-4-N,N-bis(β-hydroxyethyl)-amino-2-nitrobenzene,
1-(β-hydroxyethyl)amino-4-(N-methyl, N-β-hydroxyethyl)amino-2-nitrobenzene,
1-(β-hydroxyethyl)amino-4-(N-ethyl-N-β-hydroxyethyl)-amino-2-nitrobenzene,
1-(β,γ-dihydroxypropyl)amino-4-(N-ethyl-N-β-hydroxyethyl)amino-2-nitrobenzene,
the 2-nitro-para-phenylenediamines of the following formula:

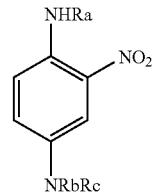

in which:
Rb represents a $C_1$-$C_4$ alkyl radical, a β-hydroxyethyl or β-hydroxypropyl or γ-hydroxypropyl radical;
Ra and Rc, which are identical or different, represent a β-hydroxyethyl, β-hydroxypropyl, γ-hydroxypropyl or β,γ-dihydroxypropyl radical, at least one of the radicals Rb, Rc or Ra representing a γ-hydroxypropyl radical and Rb and Rc not being able to simultaneously denote a β-hydroxyethyl radical when Rb is a γ-hydroxypropyl radical, such as those described in French patent FR 2 692 572.

Among the natural direct dyes, there may be mentioned henna, camomile, indigo, inter alia.

When they are present, the additional direct dye(s) preferably represent from 0.0005 to 12% by weight, and more preferably still from 0.005 to 6% by weight relative to the total weight of the composition.

When it is intended for oxidation dyeing, the cosmetic composition in accordance with the invention further comprises at least one oxidation base chosen from the oxidation bases conventionally used for oxidation dyeing and among which there may be mentioned in particular para-phenylenediamines, bisphenylalkylenediamines, para-aminophenols, ortho-aminophenols and heterocyclic bases and their addition salts with an acid or with an alkaline agent.

Among the para-phenylenediamines, there may be mentioned more particularly, by way of example, para-phenylenediamine, para-tolylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy) pyrrolidine and their addition salts with an acid or with an alkaline agent.

Among the para-phenylenediamines cited above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylene-diamine, 2,6-dimethyl-paraphenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethoxy-para-phenylenediamine and their addition salts with an acid or with an alkaline agent.

Among the bisphenylalkylenediamines, there may be mentioned more particularly, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylene-diamine, N,N'-bis(4-methylaminophenyl)tetramethylene-diamine, N,N'-bis(ethyl)-N,N'-bis(4'-amino-3'-methylphenyl) ethylenediamine, 1,8-bis(2,5-diamino-phenoxy)-3,5-dioxaoctane and their addition salts with an acid or with an alkaline agent.

Among the para-aminophenols, there may be mentioned more particularly, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol and their addition salts with an acid or with an alkaline agent.

Among the ortho-aminophenols, there may be mentioned more particularly, by way of example, 2-aminophenol, 2-amino-5-methylphenol, 2-amino-6-methylphenol, 5-acetamido-2-aminophenol and their addition salts with an acid or with an alkaline agent.

Among the heterocyclic bases, there may be mentioned more particularly, by way of example, pyridine derivatives, pyrimidine derivatives and pyrazole derivatives and their addition salts with an acid or with an alkaline agent.

When they are used, the oxidation base(s) preferably represent from 0.0005 to 12% by weight, and more preferably still from 0.005 to 6% by weight, relative to the total weight of the composition.

When it is intended for oxidation dyeing, the composition according to the invention may also comprise at least one coupler so as to modify or enrich with glints the shades obtained using the direct dyes and the oxidation base(s).

The couplers which can be used may be chosen from the couplers conventionally used in oxidation dyeing, and among which there may be mentioned in particular meta-phenylenediamines, meta-aminophenols, meta-diphenols and heterocyclic couplers and their addition salts with an acid or with an alkaline agent.

These couplers are more particularly chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole and their addition salts with an acid or with an alkaline agent.

When they are present, the coupler(s) preferably represent from 0.0001 to 10% by weight, and still more preferably from 0.005 to 5% by weight relative to the total weight of the composition.

In general, the addition salts with an acid which can be used in the context of the compositions of the invention (oxidation bases and couplers) are chosen in particular from the hydrochlorides, the hydrobromides, the sulfates, the citrates, the succinates, the tartrates, the tosylates, the benzenesulfonates, the lactates and the acetates.

The addition salts with an alkaline agent which can be used in the context of the compositions of the invention (oxidation bases and couplers) are chosen in particular from the addition salts with alkali or alkaline-earth metals, with aqueous ammonia, with organic amines including alkanolamines and the compounds of formula (II).

The cosmetic composition in accordance with the invention may also comprise various adjuvants which are conventionally used in cosmetic compositions in particular for dyeing human keratin fibers, such as anionic, cationic, nonionic, amphoteric or zwitterionic polymers or mixtures thereof; inorganic thickening agents; antioxidants; penetrating agents; sequestering agents; perfumes; dispersing agents; conditioning agents such as for example cations, cationic or amphoteric polymers, chitosans, modified or unmodified, volatile or nonvolatile silicones; film-forming agents; ceramides; preservatives; stabilizers; opacifying agents.

The composition may comprise one or more surfactants. The latter may be chosen indistinguishably, alone or as mixtures, from anionic, amphoteric, nonionic, zwitterionic and cationic surfactants.

The surfactants which are suitable for carrying out the present invention are in particular the following:

(i) Anionic Surfactant(s):

By way of example of anionic surfactants which can be used, alone or as mixtures, in the context of the present invention there may be mentioned in particular (nonlimiting list) the salts (in particular alkali metal, especially sodium, salts, ammonium salts, amine salts, amino alcohol salts or magnesium salts) of the following compounds: alkyl sulfates, alkyl ether sulfates, alkylamido ether sulfates, alkylaryl polyether sulfates, monoglyceride sulfates; alkyl sulfonates, alkyl phosphates, alkylamidesulfonates, alkylaryl sulfonates, α-olefinsulfonates, paraffinsulfonates; $(C_6-C_{24})$alkyl sulfosuccinates, $(C_6-C_{24})$alkyl ether sulfosuccinates, $(C_6-C_{24})$alkylamide sulfosuccinates; $(C_6-C_{24})$alkyl sulfoacetates; $(C_6-C_{24})$acyl sarcosinates and $(C_6-C_{24})$acyl glutamates. It is also possible to use $(C_6-C_{24})$alkyl polyglycoside carboxylic esters such as alkyl glucoside citrates, alkyl polyglycoside tartrate and alkyl polyglycoside sulfosuccinates, alkyl sulfosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can still be used, there may also be mentioned the salts of fatty acids such as the salts of oleic, ricinoleic, palmitic and stearic acids, the acids of copra oil or of hydrogenated copra oil; the acyllactylates whose acyl radical comprises 8 to 20 carbon atoms. It is also possible to use the alkyl D-galactosideuronic acids and their salts, the polyoxyalkylenated $(C_6-C_{24})$alkyl ether carboxylic acids, the polyoxyalkylenated $(C_6-C_{24})$alkylaryl ether carboxylic acids, the polyoxyalkylenated $(C_6-C_{24})$alkyl amidoether carboxylic acids and salts thereof, in particular those comprising from 2 to 50 alkylene, in particular ethylene, oxide groups, and mixtures thereof.

(ii) Nonionic Surfactant(s):

The nonionic surfactants themselves are also compounds which are well known per se (in this respect see especially the "Handbook of Surfactants" by M. R. Porter, published by Blackie & Son (Glasgow and London), 1991, pp. 116-178)

and, in the context of the present invention, their nature does not assume any critical character. They can thus be chosen especially from (nonlimiting list) alcohols, alpha-diols or polyethoxylated or polypropoxylated alkylphenols which have a fatty chain containing, for example, 8 to 18 carbon atoms, it being possible for the number of ethylene oxide or propylene oxide groups to range especially from 2 to 50. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides containing on average 1 to 5 glycerol groups and in particular 1.5 to 4; the polyethoxylated fatty amines preferably containing 2 to 30 mol of ethylene oxide; the oxyethylenated fatty acid esters of sorbitan containing from 2 to 30 mol of ethylene oxide; the fatty acid esters of sucrose, the fatty acid esters of polyethylene glycol, the alkylpolyglycosides, the N-alkylglucamine derivatives, amine oxides such as the oxides of $(C_{10}-C_{14})$-alkylamines or the N-acylaminopropylmorpholine oxides.

(iii) Amphoteric or Zwitterionic Surfactant(s):

The amphoteric or zwitterionic surfactants may be chosen in particular from the derivatives of aliphatic secondary or tertiary amines in which the aliphatic radical is a linear or branched chain containing 8 to 18 carbon atoms and containing at least one water-solubilizing anionic group (for example carboxylate, sulfonate, sulfate, phosphate or phosphonate); $(C_8-C_{20})$alkylbetaines, sulfobetaines, $(C_8-C_{20})$alkylamido $(C_1-C_6)$alkylbetaines or $(C_8-C_{20})$alkyl-amido$(C_1-C_6)$alkyl-sulfobetaines may further be mentioned.

Among the amine derivatives, there may be mentioned the products sold under the name MIRANOL, as described in patents U.S. Pat. No. 2,528,378 and U.S. Pat. No. 2,781,354 and classified in the CTFA dictionary, 3rd edition, 1982, under the names Amphocarboxyglycinates and Amphocarboxypropionates having the respective structures:

in which: Rd denotes an alkyl radical of an acid Rd-COOH present in hydrolyzed copra oil, a heptyl, nonyl or undecyl radical, Re denotes a beta-hydroxyethyl group and Rf a carboxymethyl group; and

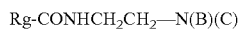

in which:
B represents —CH$_2$CH$_2$OX, C represents —(CH$_2$)$_z$—Y, with z=1 or 2,
X denotes the —CH$_2$CH$_2$—COOH group or a hydrogen atom
Y denotes —COOH or the radical —CH$_2$—CHOH—SO$_3$H
Rg denotes an alkyl radical of an acid Rh-COOH present in copra oil or in hydrolyzed linseed oil, a saturated radical or a radical comprising one or more unsaturations, in particular as $C_7$ to $C_{17}$, more particularly a $C_9$, $C_{11}$, $C_{13}$ or $C_{17}$ alkyl radical or its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, Cocoamphodipropionic acid.

By way of example, there may be mentioned the cocoamphodiacetate marketed under the trade name Miranol® C2M concentrate by the company Rhodia Chimie.

(iv) Cationic Surfactants:

Among the cationic surfactants, there may be mentioned in particular the salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of a cationic nature.

Preferably, the surfactants are nonionic, anionic or amphoteric.

Usually, the surfactants are present in a quantity of between 0.01 to 50% by weight, preferably between 0.1 and 25% by weight relative to the total weight of the composition.

The composition may further comprise one or more thickening polymers. These polymers may be ionic or nonionic, associative or nonassociative.

As regards the nonassociative thickening polymers, it is first of all recalled that for the purposes of the present invention, nonassociative thickening polymers are thickening polymers which do not contain a $C_{10}-C_{30}$ fatty chain.

Among the nonassociative thickening polymers present, there may be mentioned crosslinked homopolymers of acrylic acid, crosslinked homopolymers of 2-acrylamido-2-methylpropanesulfonic acid and their crosslinked copolymers of acrylamide, homopolymers of ammonium acrylate or copolymers of ammonium acrylate and acrylamide, nonionic guar gums, biopolysaccharide gums of microbial origin, gums derived from plant exudates, hydroxypropyl- or carboxymethylcelluloses; pectins and alginates, alone or as mixtures.

A first family of suitable nonassociative thickening polymers is represented by crosslinked homopolymers of acrylic acid.

Among the homopolymers of this type, there may be mentioned those crosslinked with an allyl ether of an alcohol of the sugar series, such as, for example, the products sold under the names CARBOPOLS 980, 981, 954, 2984 and 5984 by the company NOVEON or the products sold under the names SYNTHALEN M and SYNTHALEN K by the company 3 VSA.

The nonassociative thickening polymers may also be chosen from crosslinked homopolymers of 2-acrylamido-2-methylpropanesulfonic acid and their crosslinked copolymers of acrylamide.

As regards these homopolymers and copolymers, which may be partially or totally neutralized, there may be mentioned polymers comprising from 90 to 99.9% by weight, relative to the total weight of the polymer, of motifs of the following formula (j):

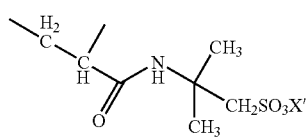

in which X' denotes a cation or a mixture of cations, or a proton.

More particularly, the cations are chosen from alkali metals (such as sodium, potassium), ammonium ions which are unsubstituted or substituted with one to three alkyl radicals, which are identical or different, comprising 1 to 6 carbon atoms, optionally bearing at least one hydroxyl radical, the cations being derived from N-methylglucamine, basic amino acids such as arginine and lysine. Preferably, the cation is an ammonium or sodium ion.

Moreover, the polymer comprises from 0.01 to 10% by weight, relative to the total weight of the polymer, of crosslinking units obtained from at least one monomer having at least two ethylenic unsaturations (carbon-carbon double bond).

The crosslinking monomers having at least two ethylenic unsaturations are chosen for example from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraalllyloxethanoyl, tetra- or diethylene glycol di(meth)acrylate, triallylamine, tetraallylethylenediamine, trimethylolpropane diallyl ether, trimethylolpropane triacrylate, methylenebis(meth)acrylamide or divinylbenzene, allyl ethers of alcohols of the sugar series, or other allyl or vinyl ethers of polyfunctional alcohols, and the allyl esters of derivatives of phosphoric and/or vinyl phosphonic acid, or mixtures of these compounds. For further details regarding these polymers, reference may be made to the document EP 815828.

Among the partially or totally neutralized crosslinked copolymers of 2-acrylamido-2-methylpropanesulfonic acid and acrylamide, there may be mentioned in particular the product described in example 1 of the document EP 503 853 and reference may be made to this document regarding these polymers.

The composition may even comprise, as nonassociative thickening polymers, homopolymers of ammonium acrylate or copolymers of ammonium acrylate and acrylamide.

By way of examples of homopolymers of ammonium acrylate, there may be mentioned the product sold under the name MICROSAP PAS 5193 by the company HOECHST. Among the copolymers of ammonium acrylate and acrylamide, there may be mentioned the product sold under the name BOZEPOL C NOUVEAU or the product PAS 5193 sold by the company HOECHST. Reference may be made in particular to the documents FR 2 416 723, U.S. Pat. No. 2,798,053 and U.S. Pat. No. 2,923,692 regarding the description and the preparation of such compounds.

The composition may also comprise homopolymers of dimethylaminoethyl methacrylate quaternized with methyl chloride or the copolymers of dimethylaminoethyl methacrylate, quaternized with methyl chloride, and acrylamide. Among the homopolymers of this type, there may be mentioned the products sold under the names SALCARE 95 and SALCARE 96 by the company CIBA-ALLIED COLLOIDS. Among the copolymers of this family, there may be mentioned the product SALCARE SC92 sold by CIBA-ALLIED COLLOIDS or the product PAS 5194 sold by HOECHST. These polymers are described and prepared in particular in the document EP 395282 to which reference may be made.

The composition may also comprise nonionic guar gums, such as for example the unmodified nonionic guar gums sold under the name VIDOGUM GH 175 by the company UNIPECTINE or under the name JAGUAR C by the company MEYHALL.

The nonionic guar gums which can be used according to the invention are preferably modified with $C_1$-$C_6$ hydroxyalkyl groups. Among the hydroxyalkyl groups, there may be mentioned, by way of example, hydroxymethyl, hydroxyethyl, hydroxypropyl and hydroxybutyl groups.

These guar gums are well known in the state of the art and may be prepared for example by relaxing the corresponding alkene oxides, such as for example propylene oxides, with the guar gum, so as to obtain a guar gum modified with hydroxypropyl groups.

The degree of hydroxyalkylation, which corresponds to the number of alkylene oxide molecules consumed by the number of free hydroxyl functional groups present on the guar gum preferably varies from 0.4 to 1.2.

Such nonionic guar gums, optionally modified with hydroxyalkyl groups, are for example sold under the trade names JAGUAR HP8, JAGUAR HP60 and JAGUAR HP120, JAGUAR DC 293 and JAGUAR HP 105 by the company MEYHALL or under the name GALACTASOL 4H4FD2 by the company AQUALON.

As suitable nonassociative thickening polymers, there may also be mentioned biopolysaccharide gums of microbial origin such as scleroglucan or xanthan gums.

Also suitable are the gums derived from plant exudates, such as gums arabic, Ghatti gums, Karaya and tragacanth gums; hydroxypropyl- or carboxymethylcelluloses; pectins and alginates.

These polymers are well known to persons skilled in the art and are described in particular in the book by Robert L. DAVIDSON entitled "Handbook of Water Soluble Gums and Resins" published by McGraw Hill Book Company (1980).

Among the thickening agents, the use of thickening systems based on associative polymers well known to a person skilled in the art and in particular of a nonionic, anionic, cationic or amphoteric nature is more particularly preferred.

It is recalled that associative polymers are hydrophilic polymers capable, in an aqueous medium, of reversibly combining with each other or with other molecules. Their chemical structure comprises more particularly at least one hydrophilic region and at least one hydrophobic region. The expression hydrophobic group is understood to mean a radical or polymer with a linear or branched, saturated or unsaturated hydrocarbon chain, comprising at least 10 carbon atoms, preferably from 10 to 30 carbon atoms, in particular from 12 to 30 carbon atoms and more preferably from 18 to 30 carbon atoms. Preferably, the hydrocarbon group is derived from a monofunctional compound. By way of example, the hydrophobic group may be derived from a fatty alcohol such as stearyl alcohol, dodecyl alcohol, decyl alcohol. It may also denote a hydrocarbon polymer such as for example polybutadiene.

The composition may therefore comprise at least one associative polymer chosen from associative, more particularly cationic or nonionic, polyurethanes, associative, more particularly cationic or nonionic, cellulose derivatives, associative vinyllactams, associative unsaturated polyacids, associative aminoplast-ethers, associative polymers or copolymers comprising at least one sulfonic group-containing ethylenically unsaturated monomer, alone or as mixtures.

Among the associative thickening polymers, there may be mentioned the associative polyurethane derivatives such as those obtained by polymerization:
- about 20% to 70% by weight of a carboxylic acid containing an $\alpha,\beta$-monoethylenic unsaturation,
- about 20 to 80% by weight of a nonsurfactant monomer containing an $\alpha,\beta$-monoethylenic unsaturation, different from the preceding one,
- about 0.5 to 60% by weight of a nonionic mono-urethane which is the product of the reaction of a monohydroxylated surfactant with a monoethylenically unsaturated monoisocyanate.

The like are described in particular in EP 173109 and more particularly in example 3. More precisely, this polymer is a methacrylic acid/methyl acrylate/dimethyl metaisopropenyl benzyl isocyanate of ethoxylated behenyl alcohol (40EO) terpolymer as an aqueous dispersion at 25%. This product is provided under the reference VISCOPHOBE DB1000 by the company AMERCHOL.

Also suitable are the cationic associative polyurethanes the family of which has been described by the Applicant in French Patent Application No. 0009609. It can be represented more particularly by the following general formula (A):

$$R-X-(P)_n-[L-(Y)_m]_r-L'-(P')_p-X'-R' \quad (A)$$

in which:
R and R', which are identical or different, represent a hydrophobic group or a hydrogen atom;
X and X', which are identical or different, represent a group containing an amine functional group carrying or otherwise a hydrophobic group, or alternatively the group L";
L, L' and L", which are identical or different, represent a group derived from a diisocyanate;
P and P', which are identical or different, represent a group containing an amine functional group carrying or otherwise a hydrophobic group;
Y represents a hydrophilic group;
r is an integer between 1 and 100, preferably between 1 and 50 and in particular between 1 and 25;
n, m and p are each independently of the others between 0 and 1000;
the molecule containing at least one protonated or quaternized amine functional group and at least one hydrophobic group.

In a very advantageous embodiment, the only hydrophobic groups of these polyurethanes are the groups R and R' at the chain ends.

According to a first preferred embodiment, the associative polyurethane corresponds to the formula (A) in which R and R' both represent independently a hydrophobic group, X, X' each represent a group L", n and p are between 1 and 1000, and L, L', L", P, P', Y and m have the meaning indicated in formula (A).

According to another preferred embodiment of the invention, the associative polyurethane corresponds to the formula (A) in which R and R' both represent independently a hydrophobic group, X, X' each represent a group L", n and p are equal to 0, and L, L', L", Y and m have the meaning in formula (A) indicated above.

The fact that n and p are equal to 0 means that these polymers do not contain units derived from a monomer containing an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents containing a hydrophobic group, that is to say compounds of the RQ or R'Q type, in which R and R' are as defined above and Q denotes a leaving group such as a halide, a sulfate and the like.

In accordance with another preferred embodiment of the invention, the associative polyurethane corresponds to formula (A) in which R and R' both represent independently a hydrophobic group, X and X' both represent independently a group containing a quaternary amine, n and p are equal to zero, and L, L', Y and m have the meaning indicated in formula (A).

The number-average molecular mass of the cationic associative polyurethanes is usually between 400 and 500 000, in particular between 1000 and 400 000, and ideally between 1000 and 300 000 g/mol.

When X and/or X' denote a group containing a tertiary or quaternary amine, X and/or X' may represent one of the following formulae:

in which:
$R_2$ represents a linear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;
$R_1$ and $R_3$, which are identical or different, denote a linear or branched, $C_1$-$C_{30}$ alkyl or alkenyl radical, an aryl radical, it being possible for at least one of the carbon atoms to be replaced by a heteroatom chosen from N, S, O, P;
$A^-$ is a physiologically acceptable counterion.

The groups L, L' and L" represent a group of formula:

in which:
Z represents —O—, —S— or —NH—; and
$R_4$ represents a linear or branched alkylene radical having from 1 to 20 carbon atoms, containing or otherwise a saturated or unsaturated ring, an arylene radical, it being possible for one or more of the carbon atoms to be replaced by a heteroatom chosen from N, S, O and P.

The groups P and P', comprising an amine functional group, may represent at least one of the following formulae:

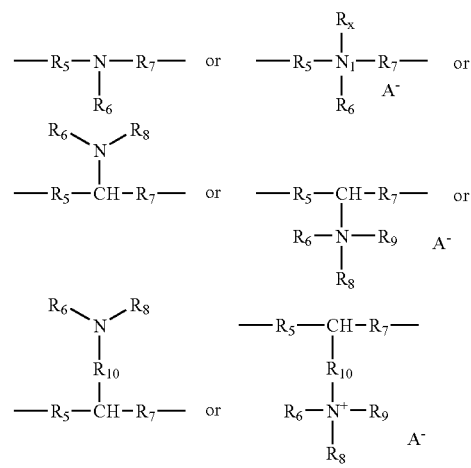

in which:
$R_5$ and $R_7$ have the same meanings as $R_2$ defined above;
$R_6$, $R_8$ and $R_9$ have the same meanings as $R_1$ and $R_3$ defined above;
$R_{10}$ represents a linear or branched alkylene group, which is optionally unsaturated and which may contain one or more heteroatoms chosen from N, O, S and P;
$A^-$ is a physiologically acceptable counterion.

As regards the meaning of Y, the expression hydrophilic group is understood to mean a polymeric or nonpolymeric water-soluble group. By way of example, there may be mentioned, when polymers are not involved, ethylene glycol, diethylene glycol and propylene glycol. In the case, in accordance with a preferred embodiment, of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The cationic associative polyurethanes of formula (A) are formed from diisocyanates and from various compounds possessing functional groups containing a labile hydrogen. The functional groups containing a labile hydrogen may be alcohol functional groups, primary or secondary amine functional groups or thiol functional groups which give, after reaction with the diisocyanate functional groups, polyurethanes, polyureas and polythioureas, respectively. The term "polyurethanes" of the present invention covers these three types of polymer, namely polyurethanes proper, polyureas and polythioureas and copolymers thereof.

A first type of compounds entering into the preparation of the polyurethane of formula (A) is a compound containing at least one unit containing an amine functional group. This compound may be multifunctional, but preferably the compound is difunctional, that is to say that according to a preferred embodiment, this compound contains two labile hydrogen atoms carried for example by a hydroxyl, primary amine, secondary amine or thiol functional group. It is also possible to use a mixture of multifunctional and difunctional compounds in which the percentage of multifunctional compounds is low.

As indicated above, this compound may contain more than one unit containing an amine functional group. It is then a polymer carrying a repeat of the unit containing an amine functional group.

This type of compounds may be represented by one of the following formulae:

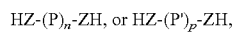
HZ-(P)$_n$-ZH, or HZ-(P')$_p$-ZH, in which Z, P, P', n and p are as defined above.

By way of examples of a compound containing an amine functional group, there may be mentioned N-methyldiethanolamine, N-tert-butyldiethanolamine, N-sulfoethyldiethanolamine.

The second compound entering into the preparation of the polyurethane of formula (A) is a diisocyanate corresponding to the formula O═C═N—R$_4$—N═C═O in which R$_4$ is defined above.

By way of example, there may be mentioned methylenediphenyl diisocyanate, methylenecyclohexane diisocyanate, isophorone diisocyanate, toluene diisocyanate, naphthalene diisocyanate, butane diisocyanate, hexane diisocyanate.

A third compound entering into the preparation of the polyurethane of formula (A) is a hydrophobic compound intended to form the terminal hydrophobic groups of the polymer of formula (A).

This compound consists of a hydrophobic group and a functional group containing a labile hydrogen, for example a hydroxyl, primary or secondary amine, or thiol functional group.

By way of example, this compound may be a fatty alcohol, such as in particular stearyl alcohol, dodecyl alcohol, decyl alcohol. When this compound contains a polymeric chain, it may be for example α-hydroxyl hydrogenated polybutadiene.

The hydrophobic group of the polyurethane of formula (A) may also result from the quaternization reaction of the tertiary amine of the compound containing at least one tertiary amine unit. Thus, the hydrophobic group is introduced by the quaternizing agent. This quaternizing agent is a compound of the RQ or R'Q type, in which R and R' are as defined above and Q denotes a leaving group such as a halide, a sulfate, and the like.

The cationic associative polyurethane may additionally comprise a hydrophilic sequence. This sequence is provided by a fourth type of compound entering into the preparation of the polymer. This compound may be multifunctional. It is preferably difunctional. It is also possible to have a mixture where the percentage of multifunctional compound is low.

The functional groups containing a labile hydrogen are alcohol, primary or secondary amine, or thiol functional groups. This compound may be a polymer terminated at the chain ends by one of these functional groups containing a labile hydrogen.

By way of example, there may be mentioned, when polymers are not involved, ethylene glycol, diethylene glycol and propylene glycol.

In the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The hydrophilic group noted Y in formula (A) is optional. Indeed, the units containing a quaternary or protonated amine functional group may suffice to provide the solubility or water-dispersibility necessary for this type of polymer in an aqueous solution. Although the presence of a hydrophilic group Y is optional, cationic associative polyurethanes are nevertheless preferred which contain such a group.

The associative polyurethane derivatives of the invention may also be nonionic polyurethane-polyethers. More particularly, said polymers contain in their chain both hydrophilic sequences most often of a polyoxyethylenated nature and hydrophobic sequences which may be aliphatic linkages alone and/or cycloaliphatic and/or aromatic linkages.

Preferably, these polyether-polyurethanes comprise at least two lipophilic hydrocarbon chains, having from 6 to 30 carbon atoms, separated by a hydrophilic sequence, it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymer for example). These same polymers may also be in the form of graft units or may be star-shaped.

The nonionic polyether-polyurethanes containing a fatty chain may be triblock copolymers whose hydrophilic sequence is a polyoxyethylenated chain comprising from 50 to 1000 oxyethylenated groups.

The nonionic polyether-polyurethanes comprise a urethane bond between the hydrophilic sequences, hence the origin of the name.

By extension, those whose hydrophilic sequences are linked by other chemical bonds to the hydrophobic sequences are also included among the nonionic polyether-polyurethanes containing a hydrophobic chain.

By way of examples of nonionic polyether-polyurethanes containing a hydrophobic chain which can be used in the invention, it is also possible to use Rhéolate® 205 containing a urea functional group sold by the company RHEOX or else the Rhéolates® 208, 204 or 212, as well as Acrysol RM 184®.

There may also be mentioned the product ELFACOS T210® containing a C$_{12}$-C$_{14}$ alkyl chain and the product ELFACOS T212® containing a C$_{18}$ alkyl chain from AKZO.

The product DW 1206B® from ROHM & HAAS containing a C$_{20}$ alkyl chain and with a urethane bond, sold at 20% dry matter content in water, may also be used.

It is also possible to use solutions or dispersions of these polymers in particular in water or in an aqueous-alcoholic medium. By way of examples of such polymers, there may be mentioned Rhéolate® 255, Rhéolate® 278 and Rhéolate® 244 sold by the company RHEOX. It is also possible to use the product DW 1206F and DW 1206J provided by the company ROHM & HAAS.

The above-described polyether-polyurethanes which can be used can also be chosen from those described in the article by G. Fonnum, J. Bakke and Fk. Hansen—Colloid Polym. Sci 271, 380-389 (1993).

Still more particularly, according to the invention, it is preferable to use a polyether-polyurethane which can be obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Such polyether-polyurethanes are sold in particular by the company ROHM & HAAS under the names Aculyn 46® and Aculyn 44® [ACULYN 46® is a polycondensate of polyethylene glycol containing 150 or 180 mol of ethylene oxide, stearyl alcohol and methylenebis(4-cyclohexyl isocyanate) (SMDI), at 15% by weight in a matrix of maltodextrin (4%) and water (81%); ACULYN 440 is a polycondensate of polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%)].

The composition may likewise comprise polymers derived from associative celluloses such as:
the quaternized cationic celluloses modified by groups comprising at least one hydrophobic chain, such as the alkyl, arylalkyl or alkylaryl groups comprising at least 8 carbon atoms, or mixtures thereof,
the quaternized cationic hydroxyethylcelluloses modified by groups comprising at least one hydrophobic chain, such as the alkyl, arylalkyl or alkylaryl groups comprising at least 8 carbon atoms, or mixtures thereof.

The alkyl radicals carried by the above-quaternized celluloses or hydroxyethylcelluloses preferably comprise from 8 to 30 carbon atoms. The aryl radicals preferably denote phenyl, benzyl, naphthyl or anthryl groups.

There may be mentioned as examples of quaternized alkylhydroxyethylcelluloses containing $C_8$-$C_{30}$ hydrophobic chains, the products QUATRISOFT LM 200®, QUATRISOFT LM-X 529-18-A®, QUATRISOFT LM-X 529-18B® ($C_{12}$ alkyl) and QUATRISOFT LM-X 529-8® ($C_{18}$ alkyl) marketed by the company AMERCHOL and the products CRODACEL QM®, CRODACEL QL® ($C_{12}$ alkyl) and CRODACEL QS(® ($C_{18}$ alkyl) marketed by the company CRODA,
the nonionic cellulose derivatives such as the hydroxyethylcelluloses modified by groups comprising at least one hydrophobic chain such as alkyl, arylalkyl or alkylaryl groups, or mixtures thereof, and in which the alkyl groups are preferably $C_8$-$C_{22}$, such as the product NATROSOL PLUS GRADE 330 CS® ($C_{16}$ alkyls) sold by the company AQUALON, or the product BERMOCOLL EHM 100® sold by the company BEROL NOBEL,
the cellulose derivatives modified by polyalkylene glycol ether of alkylphenol groups, such as the product AMERCELL POLYMER HM-1500® sold by the company AMERCHOL.

As regards the associative polyvinyl lactams, there may be mentioned for example the polymers described in particular in FR 0101106. Said polymers are more particularly cationic polymers and comprise:
a) at least one, monomer of the vinyllactam or alkylvinyllactam type;
b) at least one monomer of the following structures (a) or (b):

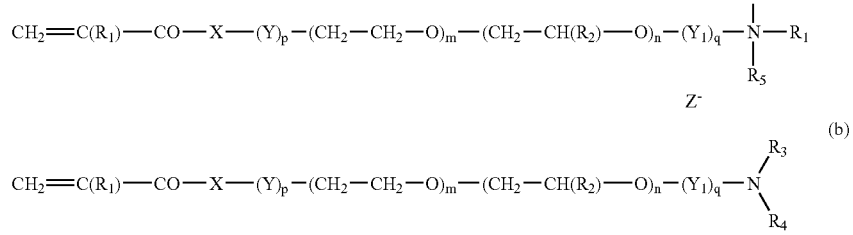

in which:
X denotes an oxygen atom or a radical $NR_6$,
R, and $R_6$ denote, independently of each other, a hydrogen atom or a linear or branched $C_1$-$C_5$ alkyl radical,
$R_2$ denotes a linear or branched $C_1$-$C_4$ alkyl radical,
$R_3$, $R_4$ and $R_5$ denote, independently of each other, a hydrogen atom, a linear or branched $C_1$-$C_{30}$ alkyl radical or a radical of formula (IV):

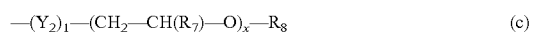

Y, $Y_1$ and $Y_2$ denote, independently of each other, a linear or branched $C_2$-$C_{16}$ alkylene radical,
$R_7$ denotes a hydrogen atom, or a linear or branched $C_1$-$C_4$ alkyl radical or a linear or branched $C_1$-$C_4$ hydroxyalkyl radical,
$R_8$ denotes a hydrogen atom or a linear or branched $C_1$-$C_{30}$ alkyl radical,
p, q and r denote, independently of each other, either the value 0, or the value 1,
m and n denote, independently of each other, an integer ranging from 0 to 100,
x denotes an integer ranging from 1 to 100,
Z denotes an anion of an organic or inorganic acid, with the proviso that:
at least one of the substituents $R_3$, $R_4$, $R_5$ or $R_8$ denotes a linear or branched $C_9$-$C_{30}$ alkyl radical,
if m or n is different from zero, then q is equal to 1,
if m or n are equal to zero, then p or q is equal to 0.

The poly(vinyllactam) polymers may be crosslinked or noncrosslinked and may also be block polymers.

Preferably, the counterion $Z^-$ of the monomers of formula (b) is chosen from the halide ions, the phosphate ions, the methosulfate ion, the tosylate ion.

Preferably, $R_3$, $R_4$ and $R_5$ denote, independently of each other, a hydrogen atom or a linear or branched $C_1$-$C_{30}$ alkyl radical.

More preferably, the monomer b) is a monomer of formula (b) for which, preferably still, m and n are equal to zero.

The vinyllactam or alkylvinyllactam monomer is preferably a compound of structure (d):

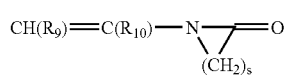

(d)

in which:

s denotes an integer ranging from 3 to 6, $R_9$ denotes a hydrogen atom or a $C_1$-$C_5$ alkyl radical, $R_{10}$ denotes a hydrogen atom or a $C_1$-$C_5$ alkyl radical, with the proviso that at least one of the radicals $R_9$ and $R_{10}$ denotes a hydrogen atom.

More preferably still, the monomer (d) is vinylpyrrolidone.

The poly(vinyllactam) polymers may also contain one or more additional, preferably cationic or nonionic, monomers.

As compounds which are more particularly preferred according to the invention, there may be mentioned the following terpolymers comprising at least:

a)—one monomer of formula (d), b)—one monomer of formula (a) in which p=1, q=0, $R_3$ and $R_4$ denote, independently of each other, a hydrogen atom or a $C_1$-$C_5$ alkyl radical and $R_5$ denotes a $C_9$-$C_{24}$ alkyl radical, and c)—a monomer of formula (b) in which $R_3$ and $R_4$ denote, independently of each other, a hydrogen atom or a $C_1$-$C_5$ alkyl radical.

More preferably still, terpolymers are used which comprise, by weight, 40 to 95% of monomer (d), 0.1 to 55% of monomer (b) and 0.25 to 50% of monomer (b).

Such polymers are described in particular in patent application WO 00/68282 the content of which forms an integral part of the invention.

As poly(vinyllactam) polymers, use is made in particular of the terpolymers vinylpyrrolidone/dimethylaminopropyl-methacrylamide/dodecyldimethylmethacrylamidopropylammonium tosylate, the terpolymers vinylpyrrolidone/dimethylaminopropylmethacrylamide/cocoyldimethylmethacrylamidopropylammonium tosylate, the terpolymers vinylpyrrolidone/dimethylaminopropyl-methacrylamide/lauryldimethylmethacrylamidopropylammonium tosylate or chloride. The terpolymer vinylpyrrolidone/dimethylaminopropylmethacrylamide/lauryldimethylmethacrylamidopropylammonium chloride is provided in water at 20% by the company ISP under the name STYLEZE W20.

The associative polyvinyllactam derivatives of the invention may also be nonionic copolymers of vinylpyrrolidone and hydrophobic monomers having a hydrophobic chain, of which there may be mentioned by way of example:

the products ANTARON V216® or GANEX V216® (vinylpyrrolidone/hexadecene copolymer) sold by the company I.S.P.

the products ANTARON V220® or GANEX V220® (vinylpyrrolidone/eicosene copolymer) sold by the company I.S.P.

Among the derivatives of associative unsaturated polyacids, there may be mentioned those containing at least one hydrophilic unit of the olefinic unsaturated carboxylic acid type, and at least one hydrophobic unit of the ($C_{10}$-$C_{30}$) alkyl ester of unsaturated carboxylic acid type.

These polymers are chosen in particular from those in which the hydrophilic unit of the olefinic unsaturated carboxylic acid type corresponds to the monomer of the following formula (e)

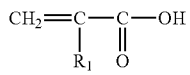

(e)

in which $R_1$ denotes H or $CH_3$ or $C_2H_5$, that is to say acrylic acid, methacrylic acid or ethacrylic acid units, and in which the hydrophobic unit of the ($C_{10}$-$C_{30}$)alkyl ester of unsaturated carboxylic acid type corresponds to the monomer of the following formula (f):

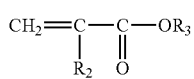

(f)

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}$-$C_{30}$, and preferably $C_{12}$-$C_{22}$, alkyl radical.

($C_{10}$-$C_{30}$)alkyl esters of unsaturated carboxylic acids comprise for example lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate, and dodecyl methacrylate.

Anionic polymers of this type are described and prepared for example according to patents U.S. Pat. Nos. 3,915,921 and 4,509,949.

In this type of anionic associative polymers, polymers are used more particularly which are formed from a mixture of monomers comprising:

(i) mainly acrylic acid, (ii) an ester of formula (f) described above and in which $R_2$ denotes H or $CH_3$, $R_3$ denoting an alkyl radical having from 12 to 22 carbon atoms, (iii) and a crosslinking agent which is a well known copolymerizable polyethylenically unsaturated monomer, such as diallyl phthalate, allyl (meth)acrylate, divinylbenzene, (poly)ethylene glycol dimethacrylate and methylenebisacrylamide.

Among this type of anionic associative polymers, preference is given to those consisting of 95 to 60% by weight of acrylic acid (hydrophilic unit), 4 to 40% by weight of $C_{10}$-$C_{30}$ alkyl acrylate (hydrophobic unit), and 0 to 6% by weight of crosslinking polymerizable monomer, or alternatively to those consisting of 98 to 96% by weight of acrylic acid (hydrophilic unit), 1 to 4% by weight of $C_{10}$-$C_{30}$ alkyl acrylate (hydrophobic unit), and 0.1 to 0.6% by weight of crosslinking polymerizable monomer such as those described above.

Among said polymers above, preference is given most particularly to the products sold by the company GOODRICH under the trade names PEMULEN TR1®, PEMULEN TR2®, CARBOPOL 1382®, and more preferably still PEMULEN TR1®, and the product sold by the company S.E.P.P.I.C. under the name COATEX SX®.

Among the derivatives of associative unsaturated polyacids, there may also be mentioned those comprising among their monomers a α,β-monoethylenically unsaturated carboxylic acid and an ester of a α,β-monoethylenically unsaturated carboxylic acid and of an oxyalkylenated fatty alcohol.

Preferably, these compounds also comprise, as monomer, an ester of a α,β-monoethylenically unsaturated carboxylic acid and of a $C_1$-$C_4$ alcohol.

By way of examples of this type of compounds, there may be mentioned ACUYLN 22® sold by the company ROHM and HAAS which is an oxyalkylenated methacrylate acid/ethyl acrylate/stearyl methacrylate terpolymer.

As regards the thickening polymers of the aminoplast-ether type, there may be mentioned any product derived from the condensation of an aldehyde with an amine or an amide, and any structural unit formed of an aminoplast residue and of a divalent hydrocarbon residue linked to the aminoplast residue by an ether bond.

The polymers with an aminoplast-ether backbone are preferably chosen from those containing at least one unit of the following structure (g):

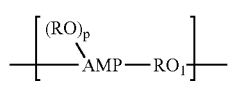

(g)

in which:
  AMP is an aminoplast residue with alkylene (or divalent alkyl) units,
  R denotes a hydrogen atom, a $C_1$-$C_4$ alkyl radical or a $C_1$-$C_4$ acyl radical,
  $RO_1$ is a divalent alkyleneoxy residue,
  p denotes a positive integer,
  the group(s) OR being linked to the alkylene units of the AMP residue.

Preferably, the polymers with an aminoplast-ether backbone are chosen from those containing at least one unit of the following structure (h):

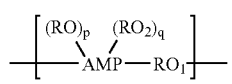

(h)

in which:
  AMP, R, $RO_1$ and p have the same meaning as above,
  $RO_2$ is a group different from RO linked to AMP by means of a heteroatom and comprising at least two carbon atoms, and
  q is a positive integer.

More preferably still, the polymers correspond to the following formulae (III) and (III)bis:

in which:
  AMP, R, $RO_1$, $RO_2$ p and q have the same meaning as above, $R_2$ or $R_3$, which are identical or different, represent a terminal group which may denote a hydrogen atom, a group $RO_1H$, a group $RO_2H$, a group AMP(OR)p or any monofunctional group such as alkyl, cycloalkyl, aryl, aralkyl, alkylaryl, alkyloxyalkyl, aryloxyalkyl, cycloalkoxyalkyl, a being a number greater than 1 and preferably greater than 2.

The aminoplast residues carrying their groups OR integrated into the polymers may be chosen, without limitation, from the following structures (1) to (12):

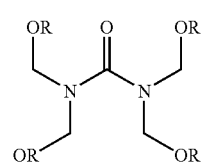

(1)

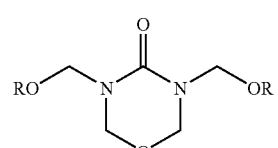

(2)

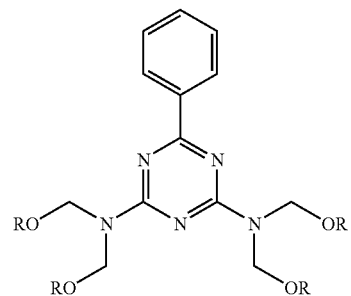

(3)

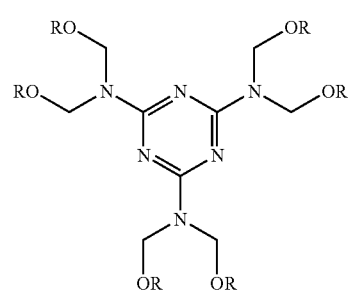

(4)

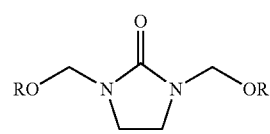

(5)

-continued

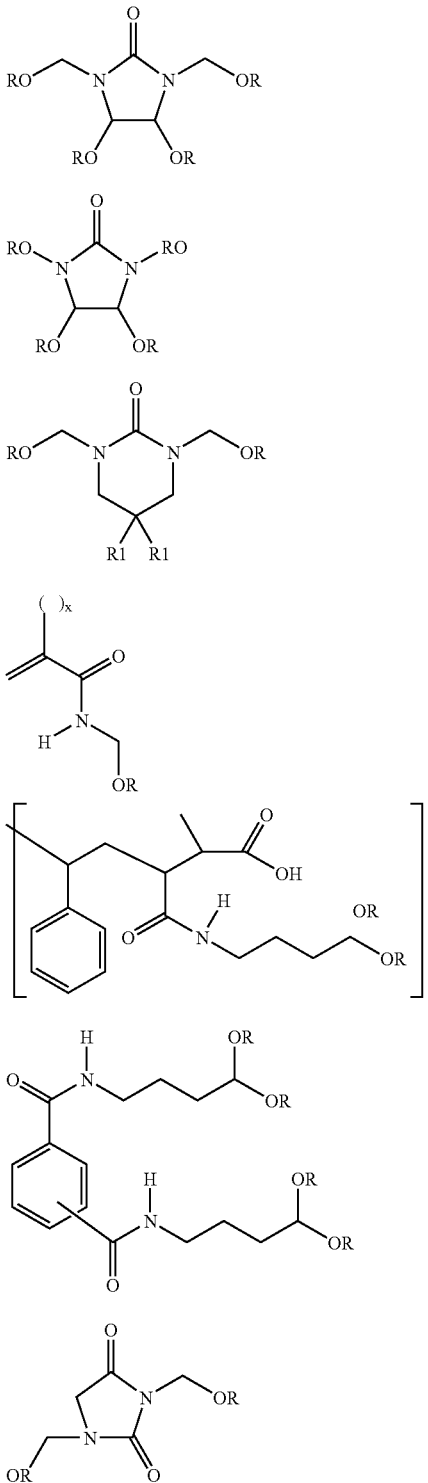

in which:
R has the same meaning as above,
$R_1$ denotes $C_1$-$C_4$ alkyl,
y is a number at least equal to 2,
x denotes 0 or 1.

Preferably, the aminoplast residue(s) carrying their groups OR are chosen from those of the following stucture (13):

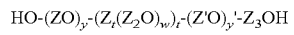

in which R, p and x have the same meanings as above.

The divalent alkyleneoxy residues are preferably those corresponding to the diols of the following general formula (14):

$$HO\text{-}(ZO)_y\text{-}(Z_t(Z_2O)_w)_t\text{-}(Z'O)_{y'}\text{-}Z_3OH \qquad (14),$$

y and y' being numbers ranging from 0 to 1000, t and w being numbers ranging from 0 to 10, Z, Z', $Z_2$ and $Z_3$ are $C_2$-$C_4$ alkylene radicals and preferably radicals —$CH_2$—$CH(Z_4)$- and —$CH_2$—$CH(Z_4)$-$CH_2$—, $Z_1$ being a branched or unbranched, aromatic or nonaromatic, linear or cyclic radical containing or not containing one or more heteroatoms and possessing from 1 to 40 carbon atoms, $Z_1$ denoting a hydrogen atom or a $C_1$-$C_4$ alkyl radical or a $C_1$-$C_3$ acyl radical, it being understood that at least one of the radicals $Z_4$ of the radicals Z, Z', $Z_2$ and $Z_3$ is different from an acyl radical.

Preferably, $Z_1$ denotes a hydrogen atom or a methyl radical.

More preferably still, t=0 and Z, Z' and $Z_3$ denote —$CH_2$—$CH_2$—, and at least one of y or y' is different from 0. The compounds of formula (14) are in this case polyethylene glycols.

The aminoplast-ether polymers of formula (g) are described in particular in patent U.S. Pat. No. 5,914,373 to which reference may be made for more details.

As polymers with an aminoplast-ether backbone of formula (g), there may be mentioned in particular the products Pure-Thix® L [PEG-180/Octoxynol-40/TMMG Copolymer (INCI name)], Pure-Thix M® [PEG-180/Laureth-50/TMMG Copolymer (INCI name)], Pure-Thix® HH [Polyether-1 (INCI name)]; Pure Thix TX-1442® [PEG-18/dodoxynol-5/PEG-25 tristyrylphenol/tetramethoxy methyl glycoluril copolymer] provided by the company Sud-Chemie.

The thickening polymers entering, as ingredient, into the composition according to the invention may also be chosen from the associative polymers containing at least one ethylenically unsaturated monomer having a sulfonic group, in free or partially or totally neutralized form and comprising at least one hydrophobic part.

Preferably, said polymers are partially or totally neutralized with an inorganic base (sodium hydroxide, potassium hydroxide, aqueous ammonia) or an organic base such as mono-, di- or triethanolamine, an aminomethylpropanediol, N-methylglucamine, basic amino acids such as arginine and lysine, and mixtures of these compounds.

These associative polymers may be crosslinked or not, and are preferably crosslinked polymers. In this case, the crosslinking agents being obtained from at least one monomer having at least two ethylenic unsaturations (carbon-carbon double bond).

The crosslinking monomers having at least two ethylenic unsaturations are chosen for example from diallyl ether, triallyl cyanurate, diallyl maleate, allyl (meth)acrylate, dipropylene glycol diallyl ether, polyglycol diallyl ethers, triethylene glycol divinyl ether, hydroquinone diallyl ether, tetraallyl oxethanoyl, tetra- or diethylene glycol di(meth)acrylate, triallylamine, tetraallylethylene-diamine, trimethylolpropane diallyl ether, trimethylolpropane triacrylate, methylenebis(meth)acrylamide or divinylbenzene, allyl ethers of alcohols of the sugar series, or other allyl or vinyl ethers of polyfunctional alcohols, and the allyl esters of the derivatives of phosphoric and/or vinylphosphonic acid, or mixtures of these compounds.

Use is made more particularly of methylenebisacrylamide, allyl methacrylate or trimethylolpropane triacrylate. The degree of crosslinking varies in general from 0.01 to 10% by mol, relative to the polymer.

The ethylenically unsaturated monomers having a sulfonic group are chosen in particular from vinylsulfonic acid, styrenesulfonic acid, (meth)acrylamido($C_1$-$C_{22}$)alkylsulfonic acids, N-($C_1$-$C_{22}$)alkyl(meth)acrylamido($C_1$-$C_{22}$)alkylsulfonic acids such as undecylacrylamidomethanesulfonic acid and their partially or totally neutralized forms.

More particularly, use may be made of the (meth)acrylamido($C_1$-$C_{22}$)alkylsulfonic acids such as for example acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid, 2-acrylamido-2,6-dimethyl-3-heptanesulfonic acid and their partially or totally neutralized forms.

2-Acrylamido-2-methylpropanesulfonic acid (AMPS) and its partially or totally neutralized forms are preferably used.

The amphiphilic polymers present in the composition according to the invention may also be chosen from the random amphiphilic polymers of AMPS which are modified by reaction with a $C_6$-$C_{22}$ n-monoalkylamine or di-n-alkylamine, and such as those described in application WO00/31154.

The hydrophobic monomers which constitute the hydrophobic part of the polymer are preferably chosen from the acrylates or acrylamides of the following formula (k):

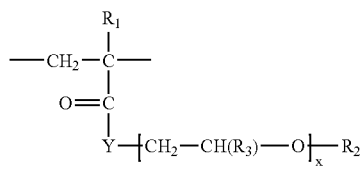

in which $R_1$ and $R_3$, which are identical or different, denote a hydrogen atom or a linear or branched $C_1$-$C_6$ alkyl radical (preferably methyl); Y denotes O or NH; $R_2$ denotes a hydrophobic hydrocarbon radical as defined above; x denotes a number of moles of alkylene oxide and varies from 0 to 100.

The radical $R_2$ is advantageously chosen from linear $C_6$-$C_{18}$ alkyl radicals (for example n-hexyl, n-octyl, n-decyl, n-hexadecyl, n-dodecyl), branched or cyclic alkyl radicals (for example cyclododecane ($C_{12}$) or adamantane ($C_{10}$)); perfluorinated $C_6$-$C_{18}$ alkyl radicals (for example the group of formula —($CH_2$)$_2$—$CF_2$)$_9$—$CF_3$); the cholesteryl radical ($C_{27}$) or a cholesterol ester residue such as the cholesteryl oxyhexanoate group; aromatic polycyclic groups such as naphthalene or pyrene. Among these radicals, the linear alkyl radicals and more particularly the n-dodecyl radical are more particularly preferred.

According to a particular embodiment of the invention, the monomer of formula (k) contains at least one alkylene oxide unit ($x \geqq 1$) and preferably one polyoxyalkylenated chain. The polyoxyalkylenated chain preferably consists of ethylene oxide units and/or propylene oxide units and more particularly still consists of ethylene oxide units. The number of oxyalkylenated units varies in general from 3 to 100 and more preferably from 3 to 50 and more preferably still from 7 to 25.

The copolymers may also contain other ethylenically unsaturated hydrophilic monomers chosen for example from (meth)acrylic acids and their β-substituted alkyl derivatives and their esters obtained with monoalcohols or mono- or polyalkylene glycols, (meth)acrylamides, vinylpyrrolidone, maleic anhydride, itaconic acid or maleic acid or mixtures of these compounds.

These copolymers are described in particular in the documents EP750899, U.S. Pat. No. 5,089,578, the following publications by Yotaro Morishima: "Self-assembling amphiphilic polyelectrolytes and their nanostructures—Chinese Journal of Polymer Science Vol. 18, No. 40, (2000), 323-336."; "Miscelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704"; "Solution properties of miscelle networks formed by nonionic moieties covalently bound to a polyelectrolyte: salt effects on rheological behaviour—Langmuir, 2000, Vol. 16, No. 12, 5324-5332"; "Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The distribution of the monomers in the copolymer may be random or block.

Among these polymers of this type, there may be mentioned more especially:

neutralized or nonneutralized, crosslinked or noncrosslinked copolymers containing from 15 to 60% by weight of AMPS units and from 40 to 85% by weight of ($C_8$-$C_{16}$) alkyl (meth) acrylamide units or ($C_8$-$C_{16}$) alkyl (meth)acrylate units relative to the polymer, such as those described in patent EP-A750 899;

terpolymers containing from 10 to 90 mol % of acrylamide units, from 0.1 to 10 mol % of AMPS units and from 5 to 80 mol % of n-($C_6$-$C_{18}$)alkylacrylamide units, such as those described in patent US-5089578, copolymers of totally neutralized AMPS and of dodecyl methacrylate and copolymers of AMPS and of n-dodecylmethacrylamide which are noncrosslinked and crosslinked, such as those described in the articles by Morishima cited above.

There may be mentioned more particularly the copolymers consisting of AMPS units of the following formula (I):

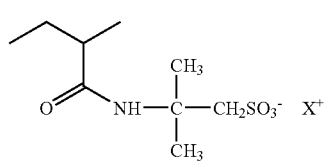

in which X⁺ has the same meaning as above, and of units of the following formula (1):

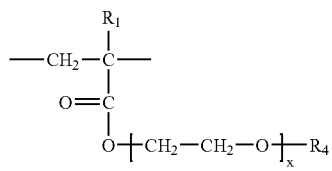

in which x denotes an integer varying from 3 to 100, preferably from 5 to 80 and more preferably from 7 to 25; $R_1$ has the same meaning as that indicated above in formula (j) and $R_4$ denotes a linear or branched $C_6$-$C_{22}$, and more preferably $C_{10}$-$C_{22}$, alkyl.

The particularly preferred polymers are those for which x=25, $R_1$ denotes methyl and $R_4$ represents n-dodecyl; they are described in the articles by Morishima mentioned above.

The polymers for which X⁺ denotes sodium or ammonium are more particularly preferred.

The polymers of the Genapol® range from the company Hoechst/Clariant may be used in the composition according to the invention.

The concentration of associative or nonassociative thickening polymer(s) present in the composition according to the invention may vary between 0.01 and 10% by weight, more particularly between 0.1 and 5% by weight, relative to the weight of the composition, and more advantageously still between 0.5 and 5% by weight relative to the weight of the composition.

Of course, persons skilled in the art will be careful to choose this or these optional additional compounds such that the advantageous properties intrinsically attached to the composition in accordance with the invention are not, or not substantially, impaired by the addition(s) envisaged.

The composition according to the invention may be provided in various forms, such as in the form of liquids, shampoos, creams, gels, or in any other appropriate form.

A particularly preferred form according to the present invention is a dyeing and/or lightening shampoo comprising, in a cosmetically acceptable aqueous medium, at least one direct dye as defined above, and at least one surfactant which is preferably nonionic.

The more particularly preferred nonionic surfactants are chosen from alkylpolyglucosides.

It is not impossible, even if this does not correspond to a preferred embodiment of the invention, for the composition to contain at least one oxidizing agent chosen for example from hydrogen peroxide, urea peroxide, alkali metal bromates, persalts such as perborates and persulfates, and enzymes such as peroxidases and oxidoreductases containing two or four electrons. The use of hydrogen peroxide or of enzymes is particularly preferred.

Another subject of the invention consists of a method for treating keratin fibers, in particular human keratin fibers.

According to a first variant, a composition as defined is applied to said fibers, dry or wet, for a sufficient time, after which the resulting fibers are rinsed, washed optionally with shampoo, rinsed again and dried or allowed to dry.

According to a second variant of the method, a composition as defined is applied to said fibers, dry or wet, without final rinsing.

The first variant can be used for any type of compositions, whether or not they comprise an oxidizing agent and/or a direct dye and/or an oxidation base optionally combined with a coupler.

The second variant is particularly appropriate for compositions not comprising an oxidation dye (oxidation base and optionally coupler) or an oxidizing agent.

In the case of the first variant of the method, the application time is usually sufficient to develop the desired coloration and/or lightening.

As a guide, the period for applying the composition is about 5 to 60 minutes and more particularly about 15 to 60 minutes.

Moreover, the temperature at which the method according to the invention is carried out is generally between room temperature (15 to 25° C.) and 60° C. and more particularly between 15 and 45° C.

In the case where the composition comprises an oxidizing agent, the method according to the invention comprises a preliminary step consisting in storing in a separate form, on the one hand, a composition comprising, in a cosmetically acceptable medium, at least one direct dye of formula (I), optionally at least one additional direct dye and/or optionally at least one oxidation base optionally combined with at least one coupler, and on the other hand, a composition comprising, in a cosmetically acceptable medium, at least one oxidizing agent, and then in mixing them at the time of use. Once this has been done, the method according to the invention is carried out in accordance with what was stated above.

Another subject of the invention is a multicompartment device comprising at least one compartment containing a composition comprising at least one direct dye of formula (I), and at least one other compartment containing a composition comprising at least one oxidizing agent. This device may be equipped with means which make it possible to deliver the desired mixture to the hair, such as the devices described in patent FR 2586913.

It should be noted that in the case where the composition contains at least one additional direct dye and/or at least one oxidation base optionally combined with at least one coupler, according to a first variant, this or these compound(s) is (are) in the first compartment of the device described above. According to a second variant, the additional direct dye and/or the oxidation base/coupler are stored in a third compartment.

It is specified that it would not be impossible to have a third variant combining the preceding two, in which the additional direct dye and/or the oxidation base and optionally the coupler would be partly in the first compartment with the direct dye of formula (I), and partly in a third compartment.

The examples which follow are intended to illustrate the invention without, however, limiting its scope.

EXAMPLE 1

The following composition is prepared:
Fluorescent dye (A) 1.73×102 mol/l
Distilled water qs 100%
The compound (A) has the following structure:

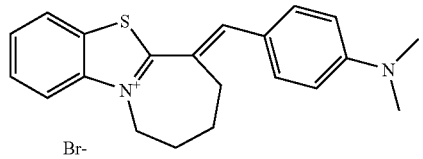

Br-

Bromide of 6-[p-(dimethylamino)benzylidene]-7,8,9,10-tetrahydro-6H-azepino[2,1-b]

The composition is applied to chestnut brown hair (tone height 4) for 20 minutes at room temperature. The bath ratio is set at 5. After dyeing, the locks are rinsed and dried.

A lightening effect is obtained which is fast to shampooing. Furthermore, the composition is stable.

EXAMPLE 2

The following composition is prepared:
Compound (B) $10^{-3}$ mol %
Distilled water qs 100%
The compound (B) has the following structure:

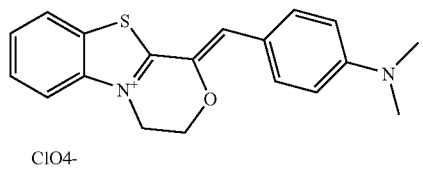

ClO4-

Perchlorate of 1H-[1,4]oxazino[3,4-b]benzothiazolium, 1-[[4-(dimethylamino)phenyl]methylene]-3,4-dihydro The composition is applied to natural gray hair for 20 minutes at room temperature. The bath ratio is set at 5. After dyeing, the locks are rinsed and dried.

The color obtained is fast to shampooing.
The composition is stable to storage.

EXAMPLE 3

The following composition is prepared:
Compound (B) $10^{-3}$ mol %
Distilled water qs 100%
The compound (B) has the following structure:

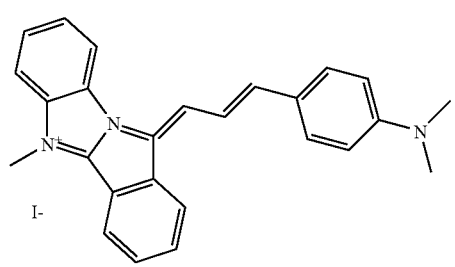

I-

Iodide of 11-[3-(4-dimethylaminophenyl)allylidene]-5-methyl-11H-benzo[4,5]imidazo[2,1-a]isoindol-5-ium The composition is applied to natural gray hair for 20 minutes at room temperature. The bath ratio is set at 5. After dyeing, the locks are rinsed and dried.

The color obtained is fast to shampooing.
The composition is stable to storage.

EXAMPLE 4

The following dyeing compositions are prepared:

| | |
|---|---|
| Methine direct dye of formula A, B or C | $10^{-3}$ mol % |
| Hydroxyethylcellulose sold by the company Aqualon under the name Natrosol 250 MR | 0.384% |
| Mixture of methyl, ethyl, propyl, butyl and isobutyl p-hydroxybenzoates sold by the company NIPA under the name NIPA ester 82121 | 0.032% |
| Alkyl($C_8$/$C_{10}$ 50/50) polyglucoside sold by the company SEPPIC under the name Oramix CG110 | 5% |
| Benzyl alcohol | 4% |
| Propylene glycol (8 EO) | 6% |
| Demineralized water qs | 100% |

Compounds (A), (B) and (C) are as defined above.

The dyeing composition containing (A) is applied to natural hair which is 90% white.

The bath ratio, the temperature and the leave-in time are 1, 33° C. and 30 minutes, respectively. After rinsing, shampooing and drying under a hood drier for 30 minutes, the hair has a very esthetic orange coloration.

The color obtained is fast to shampooing. The composition is stable to storage.

The dyeing composition containing (B) is applied to natural hair which is 90% white. The bath ratio, the temperature and the leave-in time are 1, 33° C. and 30 minutes, respectively. After rinsing, shampooing and drying under a hood drier for 30 minutes, the hair has a very esthetic red coloration.

The color obtained is fast to shampooing. The composition is stable to storage.

The dyeing composition containing (C) is applied to natural gray hair for 20 minutes at room temperature. The bath ratio is set at 5. After dyeing, the locks are rinsed and dried. The purple color obtained is fast to shampooing. The composition is stable to storage.

When X and/or X' denote a group containing a tertiary or quaternary amine, X and/or X' may represent one of the following formulae:

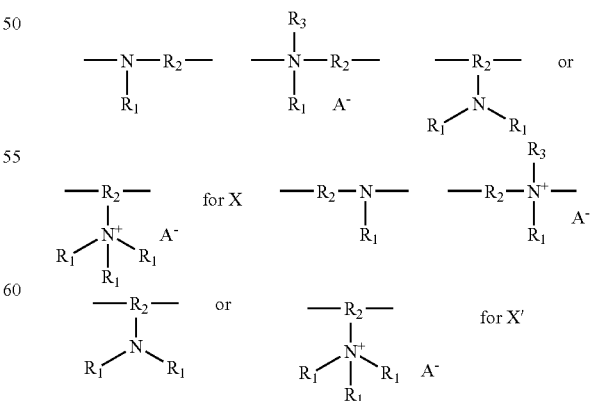

in which:

$R_2$ represents alinear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;

$R_1$ and $R_3$, which are identical or different, denote a llinear or branched, $C_1$-$C_{30}$ alkyl or alkenyl radical, an aryl radical, it being possible for at least one of the carbon atoms to be replaced by a heteroatom chosen from N, S, O, P;

$A^-$ is a physiologically acceptable counterion.

The groups L, L' and L" represent a group of formula:

$$-Z-\underset{O}{\overset{\|}{C}}-NH-R_4-NH-\underset{O}{\overset{\|}{C}}-Z-$$

More preferably still, the polymers correspond to the fallolwing formulae: (III) and (III)bis:

$$R_2\underbrace{\left[\overset{(RO)_p}{\underset{}{\diagdown}}\text{AMP}-RO_1\right]_o}R_3 \quad (i)$$

$$R_2\underbrace{\left[\overset{(RO)_p}{\underset{}{\diagdown}}\overset{(RO_2)_g}{\underset{}{\diagup}}\text{AMP}-RO_1\right]_o}R_3 \quad (i_{bis})$$

in which:
AMP, R, $RO_1$, $RO_2$ p and q have the same meaning as above, $R_2$ or $R_3$, which are identical or different, represent a terminal group which may denote a hydrogen atom, a group $RO_1H$, a group $RO_2H$, a group AMP(OR)p or any monofunctional group such as alkyl, cycloalkyl, aryl, aralkyl, alkylaryl, alkyloxyalkyl, aryloxyalkyl, cycloalkoxyalkyl, a being a number greater than 1 and preferably greater than 2.

The aminoplast residues carrying their groups OR integrated into the polymers may be chosen, without limitation, from the following structures (1) to (12):

x denotes 0 or 1.

Preferably, the aminoplast residue(s) carrying t h e i r groups OR are chosen from those of the following stucture (13):

(13)

in which R, p and x have the same meanings as above.

The divalent alkyleneoxy residues are preferably those corresponding to the diols of the following general formula (14):

$$HO-(ZO)_y-(Z_t(Z_2O)_w)_t-(Z'O)_{y'}-Z_3OH \quad (14)$$

y and y' being numbers ranging from 0 to 1000,
t and w being numbers ranging from 0 to 10,
Z, Z', $Z_2$ and $Z_3$ are $C_2$-$C_4$ alkylene radicals and preferably radicals $-CH_2-CH(_4)-$ and $-CH_2-CH(Z_4)-CH_2-$, $-Z_1$ being a branched or unbranched, aromatic or nonaromatic, linear or cyclic radical containing or not containing one or more heteroatoms and possessing from 1 to 40 carbon atoms, $Z_1$ denoting a hydrogen atom or a $C_1$-$C_4$ alkyl radical or a $C_1$-$C_3$ acyl radical, it being understood that at least one of the radicals $Z_4$ of the radicals Z, Z', $Z_2$ and $Z_3$ is different from an acyl radical.

Preferably, $Z_1$ denotes a hydrogen atom or a methyl radical.

The invention claimed is:

1. A composition comprising, in a cosmetically acceptable medium, at least one direct dye of the following formula (I):

(I)

wherein:
X is chosen from O, S, CRR' and $NR_8$;
W is chosen from $CR_9R_4$ and O;
$R_1$ and $R_2$, which may be identical or different, are chosen from hydrogen atoms, trihalomethyl groups, halogen atoms, $C_6$-$C_{30}$ aryl groups, cyano groups, sulfo groups, amino groups, acylamino groups, ($C_1$-$C_4$)alkoxycarbonyl groups, $C_1$-$C_6$ carboxyalkoxy groups, dialkylaminosulfonyl groups for which the alkyl radicals form a 5- or 6-membered ring with the nitrogen atom to which they are attached, and linear, branched or cyclic alkyl radicals comprising from 1 to 22 carbon atoms and optionally substituted with at least one group chosen from a hydroxyl group, a linear or branched $C_1$-$C_6$ alkoxy group, a $C_1$-$C_6$ cycloalkoxy group, an optionally substituted aryl group, a carboxyl group, a sulfo group and a halogen atom;

$R_1$ and $R_2$, with the carbon atoms to which they are attached, may form a fused aromatic ring, R and R' independently of each other, are chosen from $C_1$-$C_4$ alkyl radicals;

$R_9$ is chosen from a hydrogen atom and a $C_1$-$C_4$ alkyl radical;

$R_3$, $R'_3$ and $R_4$, independently of each other, are chosen from hydrogen atoms, $C_1$-$C_4$ alkyl radicals and ($C_2$-$C_6$) acyloxy radicals;

$R_3$ and $R_4$ can form, with each other and the carbon atoms bearing them, a $C_6$-$C_{30}$ aryl ring;

$R_8$ is a radical chosen from $C_1$-$C_6$ alkyl, ($C_2$-$C_4$)acylaminosulfonyl($C_1$-$C_6$)alkyl, ($C_1$-$C_6$)alkylsulfonylaminocarbonyl($C_1$-$C_6$)alkyl, ($C_1$-$C_6$)hydroxyalkyl, ($C_2$-$C_6$) acyloxy($C_1$-$C_6$)alkyl, ($C_1$-$C_6$)sulfatoalkyl and ($C_1$-$C_6$) cyanoalkyl radicals;

$R_5$ is chosen from a hydrogen atom and a linear or branched alkyl radical or a cycloalkyl radical comprising from 1 to 22 carbon atoms;

$R_7$ and $R_6$, independently of each other, are chosen from hydrogen atoms, linear or branched alkyl radicals, cycloalkyl radicals, alkoxy radicals, (di)alkylamino radicals, and thioalkyl radicals, comprising from 1 to 22 carbon atoms; phenyl radicals; phenoxy radicals; diphenylamino radicals; and halogen atoms;

two substituents $R_6$ or $R_7$ belonging to two different double bonds may form with each other a ring optionally substituted with at least one group chosen from phenyl and $C_1$-$C_4$ alkyl groups comprising at least one double bond, optionally fused with a phenyl ring, $R_7$ and optionally $R_6$ form(s) with Y an optionally fused heterocyclic residue comprising in total from 5 to 30 members and from 1 to 5 heteroatoms;

Y is a (di)alkylamino radical comprising identical or non-identical, linear or branched $C_1$-$C_{10}$ alkyl radicals optionally substituted with at least one radical chosen from ($C_1$-$C_4$)alkylsulfonylamino and ($C_1$-$C_4$)(di)alkylamino radicals; or a residue of a heterocyclic or $C_6$-$C_{30}$ aromatic ring comprising in total from 5 to 30 members and from 1 to 5 heteroatoms, which is optionally fused;

these rings being unsubstituted or substituted with at least one group chosen from $C_1$-$C_4$ alkyl, ($C_1$-$C_4$)alkoxy($C_1$-$C_4$)alkyl, amino, ($C_1$-$C_4$)dialkylamino, halogen, phenyl, carboxyl, ($C_1$-$C_4$)carboxyalkyl, ($C_1$-$C_4$)trialkylammonio($C_1$-$C_4$)alkyl, optionally substituted arylalkyl and haloalkyl groups;

n is an integer ranging from 1 to 3;

m is an integer equal to 0, 1, 2 or 3;

p is an integer equal to 0 or 1; and $A^-$ is an organic or inorganic anion.

2. The composition as claimed in claim 1, wherein m is an integer equal to 0 or 1.

3. The composition as claimed in claim 1, wherein $R'_3$ is a hydrogen atom.

4. The composition as claimed in claim 1, wherein $R_3$ or $R_4$, which may be identical or different, are chosen from hydrogen and from $C_1$-$C_4$ alkyl radicals.

5. The composition as claimed in claim 1, wherein the mineral anion is chosen from halides, sulfates, bisulfates, nitrates, phosphates, hydrogen phosphates, dihydrogen phosphates, boronates, carbonates, and bicarbonates;

the organic anion is chosen from those obtained from salts of saturated or unsaturated, aromatic or nonaromatic mono- or polycarboxylic, sulfonic or sulfuric acids, optionally substituted with at least one entity chosen from hydroxyl radicals, amino radicals, and halogen atoms.

6. The composition as claimed in claim 5, wherein the mineral anion is chosen from chloride, iodide, sulfate, methosulfate and/or ethosulfate.

7. The composition as claimed in claim 1, wherein the at least one direct dye is chosen from:

iodide of 1-[[3-[(3,4-dihydro[1,4]oxazino[3,4-b]benzothiazol-1-yl)methylene]-1-cyclohexen-1-yl]methylene]-3,4-dihydro perchlorate of pyrrolo[2,1-b]benzothiazolium, 2,3-dihydro-3-[(2,3,6,7-tetrahydro-1H,5H-benzo[ij]quinolizin-9-yl)methylene)]

bromide of 1H-pyrrolo[2,1-b]benzothiazolium, 3-[[3-[[3-(2-carboxyethyl5-phenyl-2(3H)-benzoxazolylidene]ethylidene]-5,5-dimethyl-1-cyclohexen-1-yl]methylene]-7-chloro-2,3-dihydro perchlorate of pyrido[2,1-b]benzothiazolium, 4-[(2,3-dihydro-1H-pyrido[2,1-b]benzothiazol-4-yl)methylene]-1,2,3,4-tetrahydro chloride of pyrido[2,1-b]benzothiazolium, 8-(carboxymethoxy)-4-[[4-[ethyl[2-[(methylsulfonyl)amino]ethyl]amino]phenyl]methylene]-1,2,3,4-tetrahydrosalt of naphtho[1',2':4,5]thiazolo[3,2-a]pyridinium, 8-[(10,11-dihydro-9-methyl-9H-naphtho[1',2':4,5]thiazolo[3,2-a]pyridin-8-yl)methylene]-8,9,10,11-tetrahydro-9-methylsalt of 1H-pyrrolo[2,1-b]benzothiazolium, 3-[1-(1,2-dihydropyrrolo[2,1-b]benzothiazol-3-yl)ethylidene]-2,3-dihydro iodide of pyrido[2,1-b]benzothiazolium, 4-[[3-[(2,3-dihydro-1H-pyrido[2,1-b]benzothiazol-4-yl)methylene]-1-cyclohexen-1-yl]methylene]-1,2,3,4-tetrahydro perchlorate of 3-[(1,2-dihydro-1-methylpyrrolo[2,1-b]benzothiazol-3-yl)methylene]-2,3-dihydro-1-methyl-1H-pyrrolo[2,1-b]benzothiazolium perchlorate of 1-ethyl-3-[(1-ethyl-1,2-dihydropyrrolo[2,1-b]benzothiazol-3-yl)methylene]-2,3-dihydro-1H-pyrrolo[2,1-b]benzothiazolium perchlorate of 3-[(1,2-dihydropyrrolo[2,1-b]benzothiazol-3-yl)methylene]-2,3-dihydro-1H-pyrrolo[2,1-b]benzothiazolium perchlorate of 4-[(2,3-dihydro-1-methyl-1H-pyrido[2,1-b]benzothiazol-4-yl)methylene]-1,2,3,4-tetrahydro-1-methylpyrido[2,1-b]benzothiazolium perchlorate of 1H-pyrrolo[2,1-b]benzothiazolium, 3-[[4-(dimethylamino)phenyl]methylene]-2,3-dihydro bromide of 6-[p-(dimethylamino)benzylidene]-7,8,9,10-tetrahydro-6H-azepino[2,1-b]

bromide of 4-[p-(dimethylamino)benzylidene]-1,2,3,4-tetrahydropyrido[2,1-b]

bromide of 1H-pyrrolo[2,1-b]benzothiazolium, 3-[[3-[(1,2-dihydropyrrolo[2,1-b]benzothiazol-3-yl)methylene]-1-cyclohexen-1-yl]methylene]-2,3-dihydro iodide of pyrido[2,1-b]benzothiazolium, 4-[[3-[(2,3-dihydro-1H-pyrido[2,1-b]benzothiazol-4-yl)methylene]-1-cyclopenten-1-yl]methylene]-1,2,3,4-tetrahydro iodide of 1H-[1,4]oxazino[3,4-b]benzothiazolium, 1-[[3-[(3,4-dihydro[1,4]oxazino[3,4-b]benzothiazol-1-yl)methylene]-1-cyclopenten-1-yl]methylene]-3,4-dihydro, 1H-pyrrolo[2,1-b]benzothiazolium, 3-[[3-[(1,2-dihydropyrrolo[2,1-b]benzothiazol-3-yl)methylene]-1-cyclopenten-1-yl]methylene]-2,3-dihydroperchlorate of 9H-naphtho[2',1':4,5]thiazolo[2,3-c][1,4]oxazinium, 11-[[4-(dimethylamino)phenyl]methylene]-8,1 1-dihydro-, salt of 1H-[1,4]oxazino[3,4-b]benzothiazolium, 1-[1-(3,4-dihydro-7-methyl[1,4]oxazino[3,4-b]benzothiazol-1-yl)ethylidene]-3,4-dihydro-7-methyl salt of 1H-[1,4]oxazino[3,4-b]benzothiazolium, 1-[(3,4-dihydro-7-methyl[1,4]oxazino[3,4-b]benzothiazol-1-yl)methylene]-3,4-dihydro-7-methyl salt of 1H-[1,4]oxazino[3,4-b]benzothiazolium, 1-[(3,4-dihydro4-methyl[1,4]oxazino[3,4-b]benzothiazol-1-yl)methylene]-3,4-dihydro-4-methyl methylbenzene sulfonate of 1H-[1,4]oxazino[3,4-b]benzothiazolium, 1-[(3,4-dihydro[1,4]oxazino[3,4-b]benzothiazol-1-yl)methylene]-3,4-dihydro 1H-[1,4]oxazino[3,4-b]benzothiazolium, 1-[[4-(dimethylamino)phenyl]methylene]-3,4-dihydro iodide of pyrido[2,1-b]benzothiazolium, 4-[1-(2,3-dihydro-3-methyl-1H-pyrido[2,1-b]benzothiazol-4-yl)ethylidene]-1,2,3,4-tetrahydro-3-methyl iodide of 1H-[1,4]oxazino[3,4-b]benzothiazolium, 1-[1-(3,4-dihydro-7-methyl[1,4]oxazino-[3,4-b]benzothiazol-1-yl)propylidene]-3,4-dihydro-7-methyl iodide of naphtho[1',2':4,5]thiazolo[3,2-a]pyridinium, 8-[(10,11-dihydro-9-methyl-9H-naphtho[1',2':4,5]thiazolo[3,2-a]pyridin-8-yl)methylene]-8,9,10,11-tetrahydro-9-methyl salt of pyrido[2,1-b]benzoxazolium, 4-[[3-[[3-[(3-carboxyphenyl)methyl]-1-ethyl-1,3-dihydro-5-(trifluoromethyl)-2H-benzimidazol-2-ylidene]ethylidene]-2-phenyl-cyclohexen-1-yl]methylene]-1,2,3,4-tetrahydro-8-phenyl tetrafluoroboronate of pyrido[2,1-b]benzoxazolium, 4-[(2,3-dihydro-1H-pyrido[2,1-b]benzoxazol-4-yl)methylene]-1,2,3,4-tetrahydro iodide of pyrido[2,1-b]benzoxazolium,4-[[3-[[3-[(3-carboxyphenyl)methyl]-1-ethyl-1,3-dihydro-5-(trifluoromethyly2H-benzimidazol-2-ylidene]ethylidene]-2-phenyl-1-cyclohexen-1-yl]methylene]-1,2,3,4-tetrahydro-8-phenyl iodide of naphth[2',3':4,5]oxazolo[3,2-a]pyridinium, 4-[(2,3-dihydro-1H-naphth[2',3':4,5]oxazolo[3,2-a]pyridin-4-yl)methylene]-1,2,3,4-tetrahydro bromide of pyrido[2,1-b]benzoxazolium, 4-[(2,3-dihydro-8-phenyl-1H-pyrido[2,1-b]benzoxazol-4-yl)methylene]-1,2,3,4-tetrahydro-8-phenyl iodide of naphth[2',3':4,5]oxazolo[3,2-a]pyridinium, 4-[p-(dimethylamino)benzylidene]-1,2,3,4-tetrahydro bromide of pyrido[2,1-b]benzoxazolium, 4-[(1,2-dihydropyrrolo[2,1-b]benzothiazol-3-yl)methylene]-1,2,3,4-tetrahydro-8-phenyl iodide of pyrido[2,1-b]benzothiazolium, 1,4-dihydro-4-(1H-pyrido[2,1-b]benzothiazol-4-ylmethylene)

perchlorate of benzothiazolo[3,2-b]isoquinolinium, 6-(1 1H-benzothiazolo[3,2-b]isoquinolin-6-ylmethylene)-6,11-dihydro iodide of pyrido[2,1-b]benzothiazolium, 4-[[4-(dimethylamino)phenyl]methylene]-1,2,3,4-tetrahydro-3-methyl perchlorate of pyrido[2,1-b]benzothiazolium, 4-[[3-[(2,3-dihydro-1H-pyrido[2,1-b]benzothiazol-4-yl)methylene]-5-methyl-1-cyclohexen-1-yl]methylene]-1,2,3,4-tetrahydrotetrafluoroborate of 1H-pyrrolo[2,1-b]benzothiazolium, 3-[[3-[(1,2-dihydropyrrolo[2,1-b]benzothiazol-3-yl)methylene]-2-phenyl-1-cyclohexen-1-yl]methylene]-2,3-dihydro salt of naphtho[1',2':4,5]thiazolo[3,2-a]pyridinium, 8-[(10,11-dihydro-9-methyl-9H-naphtho[1',2':4,5]thiazolo[3,2-a]pyridin-8-yl)methylene]-8,9,10,11-tetrahydro-9-methylperchlorate of 7,8,9,10-tetrahydro-6-[(7,8,9,10-tetrahydroazepino[2,1-b]benzothiazol-6-yl)methylene]-6H-azepino[2,1-b]benzothiazolium perchlorate of 3-[p-(dimethylamino)benzylidene]-1-ethyl-2,3-dihydro-1H-pyrrolo[2,1-b]

bromide of 4-[(2,3-dihydro-1H-pyrido[2,1-b]benzothiazol4-yl)methylene]-1,2,3,4-tetrahydropyrido[2,1-b]benzothiazolium 4-methylbenzenesulfonate of 1H-pyrrolo[2,1-b]benzothiazolium, 7-chloro-3-[(7-chloro-1,2-dihydropyrrolo[2,1-b]benzothiazol-3-yl)methylene]-2,3-dihydro 4-methylbenzenesulfonate of pyrido[2,1-b]benzothiazolium, 4-[1-(2,3-dihydro-1H-pyrido[2,1-b]benzothiazol-1-yl)ethylidene]-1,2,3,4-tetrahydrobromide of 9H-naphtho[2',1':4,5]thiazolo[2,3-c][1,4]oxazinium, 11-[(8,9-dihydronaphtho[2',1':4,5]thiazolo[2,3-c][1,4]oxazin-11-yl)methylene]-8,11-dihydro-, methylbenzenesulfonate of 1H-[1,4]oxazino[3,4-b]benzothiazolium, 7-chloro-1-[(7-chloro-3,4-dihydro[1,4]oxazino[3,4-b]benzothiazol-1-yl)methylene]-3,4-dihydro methylbenzenesulfonate of pyrido[2,1-b]benzothiazolium, 4-[1-(2,3-dihydro-1H-pyrido[2,1-b]benzothiazol-4-yl)propylidene]-1,2,3,4-tetrahydro bromide of 1H-pyrrolo[2,1-b]benzothiazolium, 3-[(2,3-dihydro-9,9-dimethyl-9H-pyrrolo[1,2-a]indol-1-yl)methylene]-2,3-dihydro-, 4-methylbenzenesulfonate of 1H-[1,4]oxazino[3,4-b]benzothiazolium, 1-[(3,4-dihydro-7-methyl[1,4]oxazino[3,4-b]benzothiazol-1-yl)methylene]-3,4-dihydro-7-methyl 4-methylbenzensulfonate of 1H-[1,4]oxazino[3,4-b]benzothiazolium, 1-[(3,4-dihydro-7-methyl[1,4]oxazino[3,4-b]benzothiazol-1-yl)methylene]-3,4-dihydro-7-methyl tetrafluoroborate of 1H-naphtho[2,3-d]pyrrolo[2,1-b]oxazolium, 2,3-dihydro-3-[[3-[[1-(2-methoxyethyl)naphth[1,2-d]oxazol-2-(1H)-ylidene]ethylidene]-5-phenyl-1-cyclohexen-1-yl]methylene]

bromide of 1H-pyrrolo[2,1-b]benzoxazolium, 3-[(1,2-dihydro-7-phenylpyrrolo[2,1-b]benzoxazol-3-yl)methylene]-2,3-dihydro-7-phenyl iodide of pyrido[2,1-b]benzoxazolium, 4-[p-(dimethylamino)benzylidene]-1,2,3,4-tetrahydro-8-phenyl perchlorate of benzothiazolo[3,2-b]isoquinolinium, 6-[[4-(dimethylamino)phenyl]-methylene]-6,1 1-dihydrohexafluorophosphate of 8H-benzo[e]pyrido[1,2-a]indolium, 9,10,11,12-tetrahydro-12,12-dimethyl-11-[[2-phenoxy-3-[(8,9,10,12-tetrahydro-12,12-dimethyl-benzo[e]pyrido[1,2-a]indol-11-yl)methylene]-1-cyclopenten-1-yl]methylene]

trifluoromethanesulfonate of pyrrolo[1,2-a]indolium, 1-[[3-[(2,9-dihydro-9,9-dimethyl-3H-pyrrolo[1,2-a]indol-1-yl)methylene]-2-[[5-(methylthio)-1,3,4-thiadiazol-2 -yl]thio]-1-cyclopenten-1-yl]methylene]-1,2,3,9-tetrahydro-9,9-dimethyl inner salt of pyrrolo[1,2-a]indolium, 3-ethyl-1,9-dihydro-2,9,9-trimethyl-1-[[5-[4-[2-phenyl-6-(4-sulfophenyl)thiopyrylium-4-yl]-1,3-butadienyl]selenophene-2-yl]methylene]-7-sulfo inner salt of pyrrolo[1,2-a]indolium, 3-ethyl-1,9-dihydro-2,9,9-trimethyl-1-[[5-[4-[2-phenyl-6-(4-sulfophenyl)thiopyrylium-4-yl]-1,3-butadienyl]-2-thienyl]methylene]-7-sulfo methanesulfonate of 6H-pyrido[1,2-a]indolium, 2-chloro-9-[[3-[(2-chloro-6,7,8,10-tetrahydro-10,10-dimethylpyrido[1,2-a]indol-9-yl)methylene]-2-(diphenylamino)-1-cyclopenten-1-yl]methylene]-7,8,9,10-tetrahydro-10,10-dimethyl 4-methylbenzenesulfonate of benzo[e]pyrrolo[1,2-a]indolium, 10-[[2-chloro-3-[(9,11-dihydro-11,11-dimethyl-8H-benzo[e]pyrrolo[1,2-a]indol-10-yl)methylene]-1-cyclohexen-1-yl]methylene]-8,9,10,11-tetrahydro-11,11-dimethyl perchlorate of 6H-pyrido[1,2-a]indolium, 7-(acetyloxy(-9-[[4-(dimethylamino)phenyl]-methylene]-7,8,9,10-tetrahydro-10,10-dimethyl perchlorate of 6H-pyrido[1,2-a]indolium, 7-(acetyloxy)-9-[[7-(acetyloxy)-6,7,8,10-tetrahydro-10,10-dimethylpyrido[1,2-a]indol-9-yl]methylene]-7,8,9,10-tetrahydro-10,10-dimethyl salt of 8H-benzo[e]pyrido[1,2-a]indolium, 9,10,11,12-tetrahydro-12,12-dimethyl-11-[(8,9,10,12-tetrahydro-12,12-dimethylbenzo[e]pyrido[1,2-a]indol-11-yl)methylene]

perchlorate of 6H-pyrido[1,2-a]indolium, 7,8,9,10-tetrahydro-10,10-dimethyl-9-[(6,7,8,10-tetrahydro-10,10-dimethylpyrido[1,2-a]indol-9-yl)methylene]

bromide of pyrrolo[1,2-a]indolium, 1-[(1,2-dihydropyrrolo[1,2-a]quinolin-3-yl)methylene]-1,2,3,9-tetrahydro-9,9-dimethyl iodide of pyrrolo[1,2-a]indolium, 1-[(2,9-dihydro-9,9-dimethyl-3H-pyrrolo[1,2-a]indol-1-yl)methylene]-1,2,3,9-tetrahydro-9,9-dimethyliodide of 11-[3-(4-dimethylaminophenyl)allyidene]-5-methyl-11H-benzo[4,5]imidazo[2,1-a]isoindol-5-ium perchlorate of pyrrolo[1,2-a]indolium,1-[[2-(diphenylamino)-3-[(7-fluoro-2,9-dihydro-9,9-dimethyl-3H-pyrrolo[1,2-a]indol-1-yl)methylene]-1-cyclohexen-1-yl]methylene]-7-fluoro-1,2,3,9-tetrahydro-9,9-dimethyl inner salt of pyrrolo[1,2-a]indolium, 1-[[2-chloro-3-[3-[2-phenyl-6-(4-sulfophenyl)thiopyrylium4-yl]-2-propenylidene]-1-cyclohexen-1-yl]methylene]-3-ethyl-1,9-dihydro-2,9,9-trimethyl-7-sulfo perchlorate of 6H-pyrido[1,2-a]indolium, 9-[[4-(dimethylamino)phenyl]methylene]-7,8,9,10-tetrahydro-7-hydroxy-10,10-dimethyl perchlorate of 8H-benzo[e]pyrido[1,2-a]indolium,11-[[4-(dimethylamino)phenyl]-methylene]-9,10,11,12-tetrahydro-12,12-dimethyl perchlorate of 6H-pyrido[1,2-a]indolium, 9-[[4-(dimethylamino)phenyl]methylene]-7,8,9,10-tetrahydro-10,10-dimethyl bromide of benzo[e]pyrrolo[1,2-a]indolium, 10-[(9,11-dihydro-11,11-dimethyl-8H-benzo[e]pyrrolo[1,2-a]indol-10-yl)methylene]-8,9,10,11-tetrahydro-11,11-dimethyl iodide of 6H-azepino[2,1-b]benzothiazolium, 7,8,9,10-tetrahydro-6-[[1-[3-(trimethylammonio)propyl]4(1H)-quinolinylidene]ethylidene]

iodide of pyrido[2,1-b]benzothiazolium, 1,2,3,4-tetrahydro4-[[1-(3-(trimethylammonio)propyl]-4(1H)-quinolinylidene]ethylidene]

iodide of naphtho[2,1-d]thiazolium, 3-(3-iodopropyl)-2-[3-[1-(3-iodopropyl)-4(1H)-quinolinylidene]-1-propenyl]

iodide of naphtho[2',1':4,5]thiazolo[3,2-a]pyridinium, 8,9,10,11-tetrahydro11-[[1-(3-iodopropyl)-4(1H)-quinolinylidene]ethylidene]

iodide of 1H-pyrrolo[2,1-b]benzothiazolium, 2,3-dihydro-3-[(1-methyl-4(1H)-quinolinylidene)ethylidene]

salt of naphtho[2,1-d]thiazolium, 3-[3-(trimethylammonio)propyl]-2-[3-[1-[3-(trimethylammonio)propyl]4(1H)-quinolinylidene]-1-propenyl]

salt of naphtho[2',1':4,5]thiazolo[3,2-a]pyridinium, 8,9,10,11-tetrahydro-11-[[1-[3-(trimethylammonio)propyl4(1H)-quinolinylidene]ethylidene]

iodide of benzimidazo[1,2-b]isoquinolinium, 6-[(3-ethyl-2-thiazolidinylidene)ethylidene]-6,11-dihydro-5-methyl iodide of 1H-[1,4]oxazino[4,3-a]benzimidazolium, 8-chloro-7-cyano-1-[(3-ethyl-2-thiazolidiylidene)ethylidene]-3,4-dihydro-10-methyl iodide of 1H-pyrrolo[1,2-a]benzimidazolium, 4-ethyl-3-[3-(4-ethyl-2,4-dihydro-1H-pyrrolo[1,2-a]benzimidazol-3-yl)-2-propenylidene]-2,3-dihydro iodide of pyrido[1,2-a]benzimidazolium, 7-bromo-5-ethyl-4-[(3-ethyl-5-methyl-2(3H)-benzoxazolylidene)ethylidene]-1,2,3,4-tetrahydro inner salt of 1H-pyrrolo[1,2-a]benzimidazolium, 6,7-dichloro-3-[(3-ethyl-2-selenazolidinylidene)ethylidene]-2,3-dihydro-4-[2-[(methylsulfonyl)amino]-2-oxoethyl]

iodide of 1H-pyrrolo[1,2-a]benzimidazolium, 4-[4-[(acetylamino)sulfonyl]butyl]-6,7-dichloro-3-[(3-ethyl-2-selenazolidinylidene)ethylidene]-2,3-dihydro inner salt of pyrido[1,2-a]benzimidazolium, 7,8-dichloro-4-[(3-ethyl-5-phenyl-2(3H)-benzoxazolylidene)ethylidene]-1,2,3,4-tetrahydro-5-[2-[(methylsulfonyl)amino]-2-oxoethyl]

iodide of 1H-pyrrolo[1,2-a]benzimidazolium, 8-chloro-4-ethyl-3-[(3-ethyl-2(3H)-benzoselenazolylidene)ethylidene]-2,3-dihydro iodide of 1H-pyrrolo[1,2-a]benzimidazolium, 7-chloro-6-(ethoxycarbonyl)-3-[(3-ethyl-2-thiazolidinylidene)ethylidene]-2,3-dihydro-4-methyl iodide of pyrido[1,2-a]benzimidazolium, 4-[(3-ethyl-2(3H benzoselenazolylidene)-ethylidene]-1,2,3,4-tetrahydro-5-methyl-7-(trifluoromethyl)

inner salt of pyrido[1,2-a]benzimidazolium, 4-[(5,6-dichloro-1,3-diethyl-1,3-dihydro-2H-benzimidazol-2-ylidene)ethylidene]-1,2,3,4-tetrahydro-5-[3-(sulfooxy)propyl]

iodide of pyrido[1,2-a]benzimidazolium, 7,8-dichloro4-[(5-chloro-1,3-diethyl-1,3-dihydro-2H-benzimidazol-2-ylidene)ethylidene]-5-ethyl-1,2,3,4-tetrahydro iodide of pyrido[1,2-a]benzimidazolium, 7-chloro-4-[(5-chloro-1,3-diethyl-1,3-dihydro-2H-benzimidazol-2-ylidene)ethylidene]-5-ethyl-1,2,3,4-tetrahydro iodide of pyrido[1,2-a]benzimidazolium, 5-[4-[(acetylamino)sulfonyl]butyl]-4-[(5,6-dichloro-1,3-diethyl-1,3dihydro-2H-benzimidazol-2-ylidene)ethylidene]-1,2,3,4-tetrahydro iodide of 1H-pyrrolo[1,2-a]benzimidazolium, 3-[(5,6-dichloro-1,3-diethyl-1,3-dihydro-2H-benzimidazol-2-ylidene)ethylidene]-4-ethyl-7-fluoro-2,3-dihydro iodide of 1H-pyrrolo[1,2-a]benzimidazolium, 7-chloro-3-[(5-chloro-1,3-diethyl-1,3-dihydro-2H-benzimidazol-2-ylidene)ethylidene]-4-ethyl-2,3-dihydro bromide of 1H-pyrrolo[1,2-a]benzimidazolium, 7-cyano-4-(2-cyanoethyl)-3-[(5,6-dichloro-1,3-diethyl-1,3-dihydro-2H-benzimidazol-2-ylidene)ethylidene]-2,3-dihydro iodide of 1H-pyrrolo[1,2-a]benzimidazolium, 6,7-dichloro-3-[(5,6dichloro-1,3-diethyl-1,3-dihydro-2H-benzimidazol-2-ylidene)ethylidene]-4-ethyl-2,3-dihydro inner salt of 1H-pyrrolo[1,2-a]benzimidazolium, 6-cyano-3-[(5-cyano-1,3-diethyl-1,3-dihydro-2H-benzimidazol-2-ylidene)ethylidene]-2,3-dihydro4-[2-[(methylsulfonyl)amino]-2-oxoethyl]

iodide of 1H-[1,4]oxazino[4,3-a]benzimidazolium, 8-chloro-1-[(5-chloro-1,3-diethyl-1,3-dihydro-2H-benzimidazol-2-ylidene)ethylidene]-10-ethyl-3,4-dihydro iodide of pyrido[1,2-a]benzimidazolium, 7,8-dichloro-4-[(5,6-dichloro-1,3-diethyl-1,3-dihydro-2H-benzimidazol-2-ylidene)ethylidene]-1,2,3,4-tetrahydro-5-(2-hydroxyethyl)

salt of pyrido[1,2-a]benzimidazolium, 4-[(5,6-dichloro-1,3-diethyl-1,3-dihydro-2H-benzimidazol-2-ylidene)ethylidene]-5-ethyl-1,2,3,4-tetrahydro-7-(1-piperidinylsulfonyl)

iodide of pyrido[1,2-a]benzimidazolium, 4-[(5,6-dichloro-1,3-diethyl-1,3-dihydro-2H-benzimidazol-2-ylidene)ethylidene]-5-ethyl-1,2,3,4-tetrahydro iodide of 1H-pyrrolo[1,2-a]benzimidazolium, 3-[(5-cyano-1,3-diethyl-1,3-dihydro-2H-benzimidazol-2-ylidene)ethylidene]-4-ethyl-2,3-dihydro iodide of 1H-pyrrolo[1,2-a]benzimidazolium, 3-[(5-chloro-1,3-diethyl-1,3-dihydro-2H-benzimidazol-2-ylidene)ethylidene]-4-ethyl-6-fluoro-2,3-dihydro iodide of 1H-pyrrolo[1,2-a]benzimidazolium, 6-chloro-3-[(5-chloro-1,3-diethyl-1,3-dihydro-2H-benzimidazol-2-ylidene)ethylidene]-4-ethyl-2,3-dihydro iodide of 1H-[1,4]oxazino[4,3-a]benzimidazolium, 7,8-dichloro-10-ethyl-1-[(3-ethyl-5,6-dimethyl-2(3H)-benzoxazolylidene)ethylidene]-3,4-dihydro iodide of 1H-[1,4]oxazino[4,3-a]benzimidazolium, 7,8-dichloro-10-ethyl-1-[(3-ethyl-5,6-dimethyl-2(3H benzoxazolylidene)ethylidene]-3,4-dihydro iodide of 1H-pyrrolo[1,2-a]benzimidazolium, 4-[2-(acetyloxy)ethyl]-6-cyano-3-[(3-ethyl-5,6-dimethyl-2(3H benzoxazolylidene)ethylidene]-2,3-dihydro iodide of 1H-[1,4]oxazino[4,3-a]benzimidazolium, 8-chloro-10-ethyl-1-[(3-ethyl-5,6-dimethyl-2(3H benzoxazolylidene)ethylidene]-3,4-dihydro iodide of pyrido[1,2-a]benzimidazolium, 5-ethyl-4-[(3-ethyl-5,6-dimethyl-2(3H)-benzoxazolylidene)ethylidene]-7-fluoro-1,2,3,4-tetrahydro iodide of 1H-pyrrolo[1,2-a]benzimidazolium, 6-(ethoxycarbonyl)-3-[(3-ethyl-5,6-dimethyl-2(3H benzoxazolylidene)ethylidene]-2,3-dihydro-4-methyl perchlorate of 1H-pyrrolo[1,2-a]benzimidazolium, 4-ethyl-3-[(3-ethyl-5-methyl-2(3H)-benzoxazolylidene)ethylidene]-7-fluoro-2,3-dihydro iodide of 1H-pyrrolo[1,2-a]benzimidazolium, 6,7-dichloro4-ethyl-3-[(3-ethyl-5,6-dimethyl-2(3H benzoxazolylidene)ethylidene]-2,3-dihydro iodide of 1H-pyrrolo[1,2-a]benzimidazolium, 6-chloro-4-ethyl-3-[(3-ethyl-5-methyl-2(3H)-benzoxazolylidene)ethylidene]-2,3-dihydro iodide of pyrido[1,2-a]benzimidazolium, 7,8-dichloro-5-ethyl-4-[(3-ethyl-5,6-dimethyl-2(3H)-benzoxazolylidene)ethylidene]-1,2,3,4-tetrahydro iodide of pyrido[1,2-a]benzimidazolium, 7-chloro-5-ethyl-4-[(3-ethyl-5-methyl-2(3H)-benzoxazolylidene)ethylidene]-1,2,3,4-tetrahydro iodide of 1H-pyrrolo[1,2-a]benzimidazolium, 8-(ethoxycarbonyl)-3-[(3-ethyl-5,6-dimethyl-2(3H benzoxazolylidene)ethylidene]-2,3-dihydro-4-methyl iodide of 1H-pyrrolo[1,2-a]benzimidazolium, 6-bromo-7-cyano-4-ethyl-3-[(3-ethyl-5,6-dimethyl-2(3H benzoxazolylidene)ethylidene]-2,3-dihydro perchlorate of 1H-pyrrolo[1,2-a]benzimidazolium, 4-[2-(acetyloxy)ethyl]-7-cyano-3-[(3-ethyl-5-methyl-2(3H)-benzoxazolylidene)ethylidene]-2,3-dihydro perchlorate of 1H-pyrrolo[1,2-a]benzimidazolium, 4-[2-(acetyloxy)ethyl]-3-[(3-ethyl-5-methyl-2(3H)-benzoxazolylidene)ethylidene]-2,3-dihydro iodide of 1H-pyrrolo[1,2-a]benzimidazolium, 6-cyano4-ethyl-3-[(3-ethyl-5,6-dimethyl-2(3H)-benzoxazolylidene)ethylidene]-2,3-dihydroiodide of 1H-[1,4]oxazino[4,3-a]benzimidazolium, 8-cyano-10-ethyl-1-[(3-ethyl-5,6-dimethyl-2(3H)-benzoxazolylidene)ethylidene]-3,4-dihydro iodide of 1H-pyrrolo[1,2-a]benzimidazolium, 6-carboxy-3-[(3-ethyl-5,6-dimethyl-2(3H)-benzoxazolylidene)ethylidene]-2,3-dihydro-4-methyl iodide of 1H-pyrrolo[1,2-a]benzimidazolium, 3-[(3-ethyl-5-methyl-2(3H)-benzoxazolylidene)ethylidene]-2,3-dihydro4-methyl-6-(1-pyrrolidinylsulfonyl)

perchlorate of 1H-pyrrolo[1,2-a]benzimidazolium, 4-ethyl-3-[(3-ethyl-5-methyl-2(3H)-benzoxazolylidene)ethylidene]-2,3-dihydro iodide of 1H-pyrrolo[1,2-a]benzimidazolium, 8-chloro-4-ethyl-3-[(3-ethyl-2-selenazolidinylidene)ethylidene]-2,3-dihydro iodide of pyrido[1,2-a]benzimidazolium, 5-ethyl-4-[(3-ethyl-2-thiazolidinylidene)ethylidene]-1,2,3,4-tetrahydro-7-(trifluoromethyl)

iodide of pyrido[1,2-a]benzimidazolium, 4-[(3-ethyl-2-thiazolidinylidene)ethylidene]-1,2,3,4-tetrahydro-5-methyl-7-(trifluoromethyl)

inner salt of 1H-pyrrolo[1,2-a]benzimidazolium, 7-bromo-6-(ethoxycarbonyl)-3-[(3-ethyl-2-thiazolidinylidene)ethylidene]-2,3-dihydro-4-[2-[(methylsulfonyl)amino]-2-oxoethyl]-, bromide of 1H-pyrrolo[1,2-a]benzimidazolium, 4-[4-[(acetylamino)sulfonyl]butyl]-7-bromo-6-(ethoxycarbonyl)-3-[(3-ethyl-2-thiazolidinylidene)ethylidene]-2,3-dihydro iodide of 1H-pyrrolo[1,2-a]benzimidazolium, 6-carboxy-3-[(3-ethyl-2-thiazolidinylideney)-ethylidene]-2,3-dihydro-4-methyl iodide of 1H-pyrrolo[1,2-a]benzimidazolium, 6-cyano4-ethyl-3-[(3-ethyl-2-thiazolidinylidene)ethylidene]-2,3-dihydro iodide of pyrido[1,2-a]benzimidazolium, 5-ethyl-4-[(3-ethyl-2-thiazolidinylidene)ethylidene]-1,2,3,4-tetrahydro-7-(1-piperdinylsulfonyl)

iodide of pyrido[1,2-a]benzimidazolium, 7-bromo-5-ethyl-4-[(3-ethyl-2-thiazolidinylidene)ethylidene]-1,2,3,4-tetrahydro iodide of pyrido[1,2-a]benzimidazolium, 7,8-dichloro-5-ethyl-4-[(3-ethyl-2-thiazolidinylidene)ethylidene]-1,2,3,4-tetrahydro iodide of pyrido[1,2-a]benzimidazolium, 7-chloro-5-ethyl-4-[(3-ethyl-2-thiazolidinylidene)-ethylidene]-1,2,3,4-tetrahydro iodide of 1H-naphtho[2,3-d]pyrrolo[1,2-a]imidazolium, 4-ethyl-3-[(3-ethyl-2-thiazolidinylidene)ethylidene]-2,3-dihydro iodide of 1H-pyrrolo[1,2-a]benzimidazolium, 3-[(3-ethyl-2-thiazolidinylidene)ethylidene]-2,3-dihydro4-methyl-6-(1-pyrrolidinylsulfonyl)

inner salt of 1H-pyrrolo[1,2-a]benzimidazolium, 7-chloro-6-(ethoxycarbonyl)-3-[(3-ethyl-2-thiazolidinylidene)ethylidene]-2,3-dihydro4-[2-[(methylsulfonyl)amino]-2-oxoethyl]- bromide of 1H-pyrrolo[1,2-a]benzimidazolium, 4-[4-[(acetylamino)sulfonyl]butyl]-7-chloro-6-(ethoxycarbonyl)-3-[(3-ethyl-2-thiazolidinylidene)ethylidene]-2,3-dihydro iodide of 1H-pyrrolo[1,2-a]benzimidazolium, 6-(ethoxycarbonyl)-3-[(3-ethyl-2-thiazolidinylidene)ethylidene]-2,3-dihydro-4-methyl iodide of 1H-pyrrolo[1,2-a]benzimidazolium, 4-ethyl-3-[(3-ethyl-2-thiazolidinylidene)ethylidene]-6-fluoro-2,3-dihydro iodide of 1H-pyrrolo[1,2-a]benzimidazolium, 8-chloro-4-ethyl-3-[(3-ethyl-2-thiazolidinylidene)ethylidene]-2,3-dihydro iodide of 1H-pyrrolo[1,2-a]benzimidazolium, 7-chloro-4-ethyl-3-[(3-ethyl-2-thiazolidinylidene)ethylidene]-2,3-dihydro iodide of 1H-[1,4]oxazino[4,3-a]benzimidazolium, 8-cyano-10-ethyl-1-[(3-ethyl-2-thiazolidinylidene)ethylidene]-3,4-dihydro iodide of 1H-[1,4]oxazino[4,3-a]benzimidazolium, 8-chloro-10-ethyl-1-[(3-ethyl-2-thiazolidinylidene)ethylidene]-3,4-dihydro iodide of pyrido[1,2-a]benzimidazolium, 7chloro-8-cyano-5-ethyl-4-[(3-ethyl-2-thiazolidinylidene)ethylidene]-1,2,3,4-tetrahydro iodide of pyrido[1,2-a]benzimidazolium, 8-cyano-5-ethyl-4-[(3-ethyl-2-thiazolidinylidene)-ethylidene]-1,2,3,4-tetrahydro iodide of 1H-pyrrolo[1,2-a]benzimidazolium, 6-chloro-4-ethyl-3[(3-ethyl-2-thiazolidinylidene)ethylidene]-2,3-dihydro iodide of 1H-pyrrolo[1,2-a]benzimidazolium, 6-bromo-7-cyano-4-ethyl-3-[(3-ethyl-2-thiazolidinylidene)ethylidene]-2,3-dihydro iodide of 1H-pyrrolo[1,2-a]benzimidazolium, 7-cyano-4-ethyl-3-[(3-ethyl-2-thiazolidinylidene)ethylidene]-6-fluoro-2,3dihydro bromide of 1-H-pyrrolo[1,2-a]benzimidazolium, 4[-4-[(acetylamino)sulfonyl]butyl]-6,7-dichloro-3-[(3-ethyl-2-selenazolidinylidene)ethylidene]-2,3-dihydro iodide of benzimidazo[1,2-b]isoquinolinium, 6-[(5,6-dichloro-1,3-diethyl-1,3-dihydro-2H-benzimidazol-2-ylidene)ethylidene]-6,11-dihydro-5-methyl iodide of 1H-[1,4]oxazino[4,3-a]benzimidazolium, 7,8-dichloro-10-ethyl-1-[(3-ethyl-2-thiazolidinylidene)ethylidene]-3,4-dihydro iodide of 1H-pyrrolo[1,2-a]benzimidazolium, 7-amino-3-[(5,6-dichloro-1,3-diethyl-1,3-dihydro-2H-benzimidazol-2-ylidene)ethylidene]-2,3-dihydro-4-methyl, iodide of pyrido[1,2-a]benzimidazolium, 7,8-dichloro-4-[(5,6-dichloro-1,3-diethyl-1,3-dihydro-2H-benzimidazol-2-ylidene)ethylidene]-5-ethyl-1,2,3,4-tetrahydro iodide of 1H-naphtho[2,3-d]pyrrolo[1,2-a]imidazolium, 3-[(5,6-dichloro-1,3-diethyl-1,3-dihydro-2H-benzimidazol-2-ylidene)ethylidene]4-ethyl-2,3-dihydro iodide of 1H-pyrrolo[1,2-a]benzimidazolium, 7-(acetylamino)-3-[(5,6-dichloro-1,3-diethyl-1,3-dihydro-2H-benzimidazol-2-ylidene)ethylidene]4-ethyl-2,3-dihydro iodide of 1H-pyrrolo[1,2-a]benzimidazolium, 7-chloro-3-[(5,6-dichloro-1,3-diethyl-1,3-dihydro-2H-benzimidazol-2-ylidene)ethylidene]-4-ethyl-2,3-dihydro iodide of pyrido[1,2-a]benzimidazolium, 7-bromo4-[(5-chloro-1,3-diethyl-1,3-dihydro-2H-benzimidazol-2-ylidene)ethylidene]-5-ethyl-1,2,3,4-tetrahydro iodide of pyrido[1,2-a]benzimidazolium, 4-[(5-chloro-1,3-diethyl-1,3-dihydro-2H-benzimidazol-2-ylidene)ethylidene]-5-ethyl-7-fluoro-1,2,3,4-tetrahydro iodide of 1H-pyrrolo[1,2-a]benzimidazolium, 3-[(5-cyano-1,3-diethyl-1,3-dihydro-2H-benzimidazol-2-ylidene)ethylidene]-4-ethyl-7-fluoro-2,3-dihydro iodide of 1H-pyrrolo[1,2-a]benzimidazolium, 3-[(5,6-dichloro-1,3-diethyl-1,3-dihydro-2H-benzimidazol-2-ylidene)ethylidene]-4-ethyl-2,3-dihydro iodide of benzimidazo[1,2-b]isoquinolinium, 6-[(3-ethyl-5,6-dimethyl-2(3H)-benzoxazolylidene)ethylidene]-6,11-dihydro-5-methyl iodide of 1H-naphtho[2,3-d]pyrrolo[1,2-a]imidazolium, 4-ethyl-3-[(3-ethyl-5-methyl-2(3H)-benzoxazolylidene)ethylidene]-2,3-dihydro iodide of 1H-pyrrolo[1,2-a]benzimidazolium, 4-ethyl-3-[(3-ethyl-5,6-dimethyl-2(3H)-benzoxazolylidene)ethylidene]-6-fluoro-2,3-dihydro iodide of 1H-pyrrolo[1,2-a]benzimidazolium, 7chloro-4-ethyl-3-[(3-ethyl-5-methyl-2(3H)-benzoxazolylidene)ethylidene]-2,3-dihydro iodide of 1H-naphtho[2,3-d]pyrrolo[1,2-a]imidazolium, 4-ethyl-3-[(3-ethyl-5,6-dimethyl-2(3H)-benzoxazolylidene)ethylidene]-2,3-dihydro iodide of 1H-pyrrolo[1,2-a]benzimidazolium, 4-ethyl-3-[(3-ethyl-5,6-dimethyl-2(3H)-benzoxazolylidene)ethylidene]-2,3-dihydro iodide of 1H-pyrrolo[1,2-a]benzimidazolium, 6-carboxy-7chloro-3-[(3-ethyl-5,6-dimethyl-2(3H)-benzoxazolylidene)ethylidene]-2,3-dihydro-4-methyl iodide of 1H-pyrrolo[1,2-a]benzimidazolium, 8-carboxy-3-[(3-ethyl-5,6-dimethyl-2(3H)-benzoxazolylidene)ethylidene]-2,3-dihydro-4-methyl iodide of 1H-pyrrolo[1,2-a]benzimidazolium, 7-chloro-6-(ethoxycarbonyl)-3-[(3-ethyl-5,6-dimethyl-2(3H)-benzoxazolylidene)ethylidene]-2,3-dihydro-4-methyl iodide of 1H-pyrrolo[1,2-a]benzimidazolium, 6-chloro-7-cyano4-ethyl-3-[(3-ethyl-2-thiazolidinylidene)ethylidene]-2,3-dihydro inner salt of 1H-pyrrolo[1,2-a]benzimidazolium, 7-bromo-6-(ethoxycarbonyl)-3-[(3-ethyl-2-thiazolidinylidene)ethylidene]-2,3-dihydro4-[3-(sulfooxy)propyl]

iodide of pyrido[1,2-a]benzimidazolium, 7-bromo-8-cyano-5-ethyl-4-[(3-ethyl-2-thiazolidinylidene)ethylidene]-1,2,3,4-tetrahydro iodide of 1H-pyrrolo[1,2-a]benzimidazolium, 4-ethyl-3-[(3-ethyl-2-thiazolidinylidene)ethylidene]-2,3-dihydro-6-methyl inner salt of pyrido[1,2-a]benzimidazolium, 7,8-dichloro-4-[(3-ethyl-2-thiazolidinylidene)ethylidene]-1,2,3,4-tetrahydro-5-[2-[(methylsulfonyl)amino]-2-oxoethyl]- iodide of pyrido[1,2-a]benzimidazolium, 5-ethyl-4-[(3-ethyl-2-thiazolidinylidene)ethylidene]-1,2,3,4-tetrahydro inner salt of 1H-pyrrolo[1,2-a]benzimidazolium, 7-chloro-6-(ethoxycarbonyl)-3-[(3-ethyl-2-thiazolidinylidene)ethylidene]-2,3-dihydro-4-[3-sulfooxy)propyl iodide of 1H-pyrrolo[1,2-a]benzimidazolium, 8-carboxy-3-[(3-ethyl-2-thiazolidinylideney)-ethylidene]-2,3-dihydro-4-methyl iodide of 1H-pyrrolo[1,2-a]benzimidazolium, 6,7-dichloro4-ethyl-3-[(3-ethyl-2-thiazolidinylidene)ethylidene]-2,3-dihydro iodide of 1H-pyrrolo[1,2-a]benzimidazolium, 4-ethyl-3-[(3-ethyl-2-thiazolidinylidene)-ethylidene]-2,3-dihydro iodide of pyrido[1,2-a]benzimidazolium, 8-cyano-5-ethyl-4-[(3-ethyl-2-thiazolidinylidene)-ethylidene]-7-fluoro-1,2,3,4-tetrahydro iodide of pyrido[1,2-a]benzimidazolium, 7-cyano-5-ethyl-4-[(3-ethyl-2-thiazolidinylidene)-1,2,3,4-tetrahydro perchlorate of 1H-pyrrolo[1,2-a]benzimidazolium, 4-[2-(acetyloxy)ethyl]-7-cyano-3-[(3-ethyl-2-thiazolidinylidene)ethylidene]-2,3-dihydro.

8. The composition as claimed in claim 7, wherein the at least one direct dye is a chloride salt.

9. The composition as claimed in claim 1, wherein the at least one direct dye is present in an amount ranging from 0.01 to 20% by weight relative to the total weight of the composition.

10. The composition as claimed in claim 9, wherein the at least one direct dye is present in an amount ranging from 0.1 to 5% by weight relative to the total weight of the composition.

11. The composition as claimed in claim 1, wherein the cosmetically acceptable medium comprises water or a mixture of water and at least one organic solvent.

12. The composition as claimed in claim 1, further comprising at least one additional direct dye chosen from nonionic, cationic and anionic direct dyes.

13. The composition as claimed in claim 12, wherein the at least one additional direct dye is chosen from nitrobenzene dyes, azo dyes, anthraquinone dyes, naphthoquinonedyes, benzoquinone dyes, indigoid dyes, derivatives of triarylmethane, and natural dyes.

14. The composition as claimed in claim 12, wherein the at least one additional direct dye is present in an amount ranging from 0.0005 to 12% by weight relative to the total weight of the composition.

15. The composition as claimed in claim 1, further comprising at least one surfactant.

16. The composition as claimed in claim 15, wherein the at least one surfactant is nonionic.

17. The composition as claimed in claim 15, wherein the at least one surfactant is present in an amount ranging from 0.01 to 50% by weight relative to the total weight of the composition.

18. The composition as claimed in claim 1, further comprising at least one nonassociative thickening polymer.

19. The composition as claimed in claim 18, further comprising at least one nonassociative thickening polymer is chosen from crosslinked homopolymers of acrylic acid, crosslinked homopolymers of 2-acrylamido-2-methylpropanesulfonic acid and their crosslinked copolymers of acrylamide, homopolymers of ammonium acrylate or copolymers of ammonium acrylate and acrylamide, nonionic guar gums, microbial biopolysaccharide gums, plant exudates gums, hydroxypropyl celluloses, carboxymethyl celluloses, pectins and alginates.

20. The composition as claimed in claim 1, further comprising at least one associative thickening polymer.

21. The composition as claimed in claim 1, further comprising at least one associative thickening polymer is chosen from associative polyurethanes, associative derivatives of cellulose, associative vinyllactams, associative unsaturated polyacids, associative aminoplast-ethers, crosslinked homopolymers of 2-acrylamido-2-methylpropanesulfonic acid and their crosslinked copolymers of acrylamide, associative polymers or copolymers comprising at least one ethylenically unsaturated monomer with a sulfonic group.

22. The composition as claimed in claim 1, wherein the associative or nonassociative thickening polymer is present in an amount ranging from 0.01 and 10% by weight relative to the total weight of the composition.

23. The composition as claimed in claim 22, wherein the associative or nonassociative thickening polymer is present in an amount ranging from 0.1 to 5% by weight relative to the total weight of the composition.

24. The composition as claimed in claim 1, in the form of a coloring shampoo.

25. The composition as claimed in claim 1, wherein the composition comprises at least one oxidation base.

26. The composition as claimed in claim 25, wherein the at least one oxidation base is combined with at least one coupler.

27. The composition as claimed in claim 25, wherein the composition comprises at least one oxidation base chosen from para-phenylenediamines, bisphenylalkylenediamines, para-aminophenols, ortho-aminophenols and heterocyclic bases and their addition salts with an acid or with an alkaline agent.

28. The composition as claimed in claim 27, wherein the at least one oxidation base is present in an amount ranging from 0.0005 to 12% by weight relative to the total weight of the composition.

29. The composition as claimed in claim 27, further comprising at least one coupler chosen from meta-phenylenediamines, meta-aminophenols, meta-diphenols and heterocyclic couplers or their addition salts with an acid or with an alkaline agent.

30. The composition as claimed in claim 29, wherein the at least one coupler is present in an amount ranging from 0.0001 to 10% by weight relative to the total weight of the dyeing composition.

31. The composition as claimed in claim 1, further comprising at least one oxidizing agent.

32. The composition as claimed in claim 31, wherein the oxidizing agent is chosen from hydrogen peroxide, urea peroxide, alkali metal bromates, persalts, and enzymes containing 2 or 4 electrons.

33. A method for treating keratin fibers, comprising:
appying a composition to keratin fibers that are wet or dry for a time sufficient to develp a coloration;
rinsing the keratin fibers;
optionally washing the keratin fivers with shampoo and rinsing the fibers a second time; and
drying the keratin fibers or leaving the keratin fibers to dry;
wherein the composition comprises, in a cosmetically acceptable medium, at least one direct dye of the following formula (I):

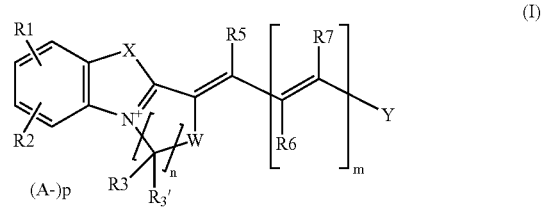

wherein:
X is chosen from O, S, CRR' and $NR_8$;
W is chosen from $CR_9R_4$ and O;
$R_1$ and $R_2$, which may be identical or different, are chosen from hydrogen atoms, trihalomethyl groups, halogen atoms, $C_6$-$C_{30}$ aryl groups, cyano groups, sulfo groups, amino groups, acylamino groups, ($C_1$-$C_4$)alkoxycarbonyl groups, $C_1$-$C_6$ carboxyalkoxy groups, dialkylaminosulfonyl groups for which the alkyl radicals form a 5- or 6-membered ring with the nitrogen atom to which they are attached, linear, branched or cyclic alkyl radical comprising from 1 to 22 carbon atoms and optionally substituted with at least one group chosen from a hydroxyl group, a linear or branched $C_1$-$C_6$ alkoxy group, a $C_1$-$C_6$ cycloalkoxy group, an optionally substituted aryl group, a carboxyl group, a sulfo group and a halogen atom;
$R_1$, and $R_2$, together with the carbon atoms to which they are attached, may optionally form a fused aromatic ring;
R and R' are independently chosen from $C_1$-$C_4$ alkyl radicals;
$R_9$ is chosen from a hydrogen atom and a $C_1$-$C_4$ alkyl radical;
$R_3$, $R'_3$ and $R_4$ are independently chosen from hydrogen atoms, $C_1$-$C_4$ alkyl radicals and ($C_2$-$C_6$)acyloxy radicals;

$R_3$ and $R_4$ can form, with each other and the carbon atoms bearing them, a $C_6$-$C_{30}$ aryl ring;

$R_8$ is a radical chosen from $C_1$-$C_6$ alkyl, $(C_2$-$C_4)$acylaminosulfonyl$(C_1$-$C_6)$alkyl, $(C_1$-$C_6)$alkylsulfonylaminocarbonyl$(C_1$-$C_6)$alkyl, $(C_1$-$C_6)$hydroxyalkyl, $(C_2$-$C_6)$ acyloxy$(C_1$-$C_6)$alkyl, $(C_1$-$C_6)$sulfatoalkyl and $(C_1$-$C_6)$ cyanoalkyl radicals;

$R_5$ is chosen from a hydrogen atom, a linear or branched alkyl radical or a cycloalkyl radical comprising from 1 to 22 carbon atoms;

$R_7$ and $R_6$ are independently chosen from hydrogen atoms, linear or branched alkyl radicals, cycloalkyl radicals, alkoxy radicals, (di)alkylamino radicals, thioalkyl radicals, comprising from 1 to 22 carbon atoms; phenyl radicals; phenoxy radicals; diphenylamino radicals; and halogen atoms;

two substituents $R_6$ or $R_7$ belonging to two different double bonds may form with each other a ring optionally substituted with at least one group chosen from phenyl and $C_1$-$C_4$ alkyl groups comprising at least one double bond, optionally fused with a phenyl ring, $R_7$ and optionally $R_6$ form(s) with Y an optionally fused heterocyclic residue comprising in total from 5 to 30 members and from 1 to 5 heteroatoms;

Y is a (di)alkylamino radical comprising identical or non-identical, linear or branched $C_1$-$C_{10}$ alkyl radicals optionally substituted with at least one group chosen from $(C_1$-$C_4)$alkylsulfonylamino groups, and $(C_1$-$C_4)$ (di)alkylamino radicals; or a residue of a heterocyclic or $C_6$-$C_{30}$ aromatic ring comprising in total from 5 to 30 members and from 1 to 5 heteroatoms, which is optionally fused;

these rings being unsubstituted or substituted with at least one group chosen from $C_1$-$C_4$ alkyl, $(C_1$-$C_4)$alkoxy$(C_1$-$C_4)$alkyl, amino, $(C_1$-$C_4)$dialkylamino, halogen, phenyl, carboxyl, $(C_1$-$C_4)$carboxyalkyl, $(C_1$-$C_4)$trialkylammonio$(C_1$-$C_4)$alkyl, optionally substituted arylalkyl and haloalkyl groups;

n is an integer ranging from 1 to 3;

m is an integer equal to 0, 1, 2 or 3;

p is an integer equal to 0 or 1; and $A^-$ is an organic or inorganic anion.

34. The method of claim 33, wherein the keratin fibers are human keratin fibers.

35. The method of claim 33, wherein the keratin fibers are not rinsed a second time.

36. A multi-compartment kit for dyeing and lightening hair, comprising:

at least one first compartment comprising a composition comprising at least one oxdizing agent; and at least one second compartment comprising a composition comprising, in a cosmetically acceptable medium, at least one direct dye of the following formula (I):

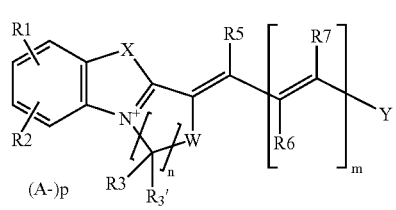

(I)

wherein:

X is chosen from O, S, CRR' and $NR_8$;

W is chosen from $CR_9R_4$ and O;

$R_1$ and $R_2$, which may be identical or different, are chosen from hydrogen atoms, trihalomethyl groups, halogen atoms, $C_6$-$C_{30}$ aryl groups, cyano groups, sulfo groups, amino groups, acylamino groups, $(C_1$-$C_4)$alkoxycarbonyl groups, $C_1$-$C_6$ carboxyalkoxy groups, dialkylaminosulfonyl groups for which the alkyl radicals form a 5- or 6-membered ring with the nitrogen atom to which they are attached, and linear, branched or cyclic alkyl radicals comprising from 1 to 22 carbon atoms and optionally substituted with at least one group chosen from a hydroxyl group, a linear or branched $C_1$-$C_6$ alkoxy group, a $C_1$-$C_6$ cycloalkoxy group, an optionally substituted aryl group, a carboxyl group, a sulfo group and a halogen atom;

$R_1$ and $R_2$, with the carbon atoms to which they are attached, may form a fused aromatic ring, R and R' independently of each other, are chosen from $C_1$-$C_4$ alkyl radicals;

$R_9$ is chosen from a hydrogen atom and a $C_1$-$C_4$ alkyl radical;

$R_3$, $R'_3$ and $R_4$, independently of each other, are chosen from hydrogen atoms, $C_1$-$C_4$ alkyl radicals and $(C_2$-$C_6)$ acyloxy radicals;

$R_3$ and $R_4$ can form, with each other and the carbon atoms bearing them, a $C_6$-$C_{30}$ aryl ring;

$R_8$ is a radical chosen from $C_1$-$C_6$ alkyl, $(C_2$-$C_4)$acylaminosulfonyl$(C_1$-$C_6)$alkyl, $(C_1$-$C_6)$alkylsulfonylaminocarbonyl$(C_1$-$C_6)$alkyl, $(C_1$-$C_6)$hydroxyalkyl, $(C_2$-$C_6)$ acyloxy$(C_1$-$C_6)$alkyl, $(C_1$-$C_6)$sulfatoalkyl and $(C_1$-$C_6)$ cyanoalkyl radicals;

$R_5$ is chosen from a hydrogen atom and a linear or branched alkyl radical or a cycloalkyl radical comprising from 1 to 22 carbon atoms;

$R_7$ and $R_6$, independently of each other, are chosen from hydrogen atoms, linear or branched alkyl radicals, cycloalkyl radicals, alkoxy radicals, (di)alkylamino radicals, a nd thioalkyl radicals, comprising from 1 to 22 carbon atoms; phenyl radicals; phenoxy radicals; diphenylamino radicals; and halogen atoms;

two substituents $R_6$ or $R_7$ belonging to two different double bonds may form with each other a ring optionally substituted with at least one group chsoen from phenyl and $C_1$-$C_4$ alkyl groups containing at least one double bond, optionally fused with a phenyl ring, $R_7$ and optionally $R_6$ form(s) with Y an optionally fused heterocyclic residue comprising in total from 5 to 30 members and from 1 to 5 heteroatoms;

Y is a (di)alkylamino radical comprising identical or non-identical, linear or branched $C_1$-$C_{10}$ alkyl radicals optionally substituted with at least one radical chosen from $(C_1$-$C_4)$alkylsulfonylamino and $(C_1$-$C_4)$(di)alkylamino radicals; or a residue of a heterocyclic or $C_6$-$C_{30}$ aromatic ring comprising in total from 5 to 30 members and from 1 to 5 heteroatoms, which is optionally fused;

these rings being unsubstituted or substituted with at least one group chosen from $C_1$-$C_4$ alkyl, $(C_1$-$C_4)$alkoxy$(C_1$-$C_4)$alkyl, amino, $(C_1$-$C_4)$dialkylamino, halogen, phenyl, carboxyl, $(C_1$-$C_4)$carboxyalkyl, $(C_1$-$C_4)$trialkylammonio$(C_1$-$C_4)$alkyl, optionally substituted arylalkyl and haloalkyl groups;

n is an integer ranging from 1 to 3;

m is an integer equal to 0, 1, 2 or 3;

p is an integer equal to 0 or 1; and $A^-$ is an organic or inorganic anion.

37. A method for treating keratin fibers, comprising: applying to said keratin fibers an agent for lightening and/or dyeing keratin fibers; wherein the agent comprises, in a cosmetically acceptable medium, at least one direct dye of the following formula (I):

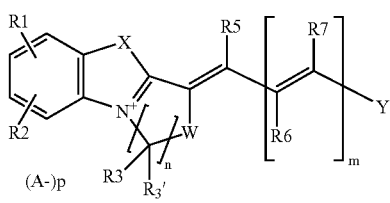

wherein:
X is chosen from O, S, CRR' and $NR_8$;
W is chosen from $CR_9R_4$ and O;
$R_1$ and $R_2$, which may be identical or different, are chosen from hydrogen atoms, trihalomethyl groups, halogen atoms, $C_6$-$C_{30}$ aryl groups, cyano groups, sulfo groups, amino groups, acylamino groups, ($C_1$-$C_4$)alkoxycarbonyl groups, $C_1$-$C_6$ carboxyalkoxy groups, dialkylaminosulfonyl groups for which the alkyl radicals form a 5- or 6-membered ring with the nitrogen atom to which they are attached, and linear, branched or cyclic alkyl radicals comprising from 1 to 22 carbon atoms and optionally substituted with at least one group chosen from a hydroxyl group, a linear or branched $C_1$-$C_6$ alkoxy group, a $C_1$-$C_6$ cycloalkoxy group, an optionally substituted aryl group, a carboxyl group, a sulfo group and a halogen atom;
$R_1$ and $R_2$, with the carbon atoms to which they are attached, may form a fused aromatic ring,
R and R' independently of each other, are chosen from $C_1$-$C_4$ alkyl radicals;
$R_9$ is chosen from a hydrogen atom and a $C_1$-$C_4$ alkyl radical;
$R_3$, $R'_3$ and $R_4$, independently of each other, are chosen from hydrogen atoms, $C_1$-$C_4$ alkyl radicals and ($C_2$-$C_6$) acyloxy radicals;
$R_3$ and $R_4$ can form, with each other and the carbon atoms bearing them, a $C_6$-$C_{30}$ aryl ring;
$R_8$ is a radical chosen from $C_1$-$C_6$ alkyl, ($C_2$-$C_4$)acylaminosulfonyl($C_1$-$C_6$)alkyl, ($C_1$-$C_6$)alkylsulfonylaminocarbonyl($C_1$-$C_6$)alkyl, ($C_1$-$C_6$)hydroxyalkyl, ($C_2$-$C_6$) acyloxy($C_1$-$C_6$)alkyl, ($C_1$-$C_6$)sulfatoalkyl and ($C_1$-$C_6$) cyanoalkyl radicals;
$R_5$ is chosen from a hydrogen atom and a linear or branched alkyl radical or a cycloalkyl radical comprising from 1 to 22 carbon atoms;
$R_7$ and $R_6$, independently of each other, are chosen from hydrogen atoms, linear or branched alkyl radicals, cycloalkyl radicals, alkoxy radicals, (di)alkylamino radicals, and thioalkyl radicals, comprising from 1 to 22 carbon atoms; phenyl radicals; phenoxy radicals; diphenylamino radicals; and halogen atoms;
two substituents $R_6$ or $R_7$ belonging to two different double bonds may form with each other a ring optionally substituted with at least one group chosen from phenyl and $C_1$-$C_4$ alkyl groups containing at least one double bond, optionally fused with a phenyl ring,
$R_7$ and optionally $R_6$ form(s) with Y an optionally fused heterocyclic residue comprising in total from 5 to 30 members and from 1 to 5 heteroatoms;
Y is a (di)alkylamino radical comprising identical or non-identical, linear or branched $C_1$-$C_{10}$ alkyl radicals optionally substituted with at least one radical chosen from ($C_1$-$C_4$)alkylsulfonylamino and ($C_1$-$C_4$)(di)alkylamino radicals; or a residue of a heterocyclic or $C_6$-$C_{30}$ aromatic ring comprising in total from 5 to 30 members and from 1 to 5 heteroatoms, which is optionally fused;
these rings being unsubstituted or substituted with at least one group chosen from $C_1$-$C_4$ alkyl, ($C_1$-$C_4$)alkoxy($C_1$-$C_4$)alkyl, amino, ($C_1$-$C_4$)dialkylamino, halogen, phenyl, carboxyl, ($C_1$-$C_4$-)carboxyalkyl, ($C_1$-$C_4$)trialkylammonio($C_1$-$C_4$)alkyl, optionally substituted arylalkyl and haloalkyl groups;
n is an integer ranging from 1 to 3;
m is an integer equal to 0, 1, 2 or 3;
p is an integer equal to 0 or 1; and
$A^-$ is an organic or inorganic anion.

* * * * *

UNITED STATES PATENT AND TRADEMARK OFFICE
CERTIFICATE OF CORRECTION

PATENT NO. : 7,425,221 B2
APPLICATION NO. : 11/223149
DATED : September 16, 2008
INVENTOR(S) : Lagrange It is certified that error appears in the above-identified patent and that said Letters Patent is hereby corrected as shown below:

In claim 7, column 129, lines 58-61, "3-[[3-[[3-(2-carboxyethyl5-phenyl-2(3H)-benzoxazolylidene]ethylidene]-5,5-dimethyl-1-cyclohexen-1-yl]methylene]-7-chloro-2,3-dihydro" should read --3-[[3-[[3-(2-carboxyethyl)-5-phenyl-2(3H)-benzoxazolylidene]ethylidene]-5,5-dimethyl-1-cyclohexen-1-yl]methylene]-7-chloro-2,3-dihydro--.

In claim 7, column 130, lines 45-46, "11-[[4-(dimethylamino)phenyl]methylene]-8,11-dihydro-," should read --11-[[4-(dimethylamino)phenyl]methylene]-8,11-dihydro-,--.

In claim 7, column 130, lines 53-55, "1-[(3,4-dihydro4-methyl[1,4]oxazino[3,4-b]benzothiazol-1-yl)methylene]-3,4-dihydro-4-methyl" should read --1-[(3,4-dihydro-4-methyl[1,4]oxazino[3,4-b]benzothiazol-1-yl)methylene]-3,4-dihydro-4-methyl--.

In claim 7, column 131, lines 13-17, "pyrido[2,1-b]benzoxazolium,4-[[3-[[3-[(3-carboxyphenyl)methyl]-1-ethyl-1,3-dihydro-5-(trifluoromethyly2H-benzimidazol-2-ylidene]ethylidene]-2-phenyl-1-cyclohexen-1-yl]methylene]-1,2, 3,4-tetrahydro-8-phenyl" should read --pyrido[2,1-b]benzoxazolium, 4-[[3-[[3-[(3-carboxyphenyl)methyl]-1-ethyl-1,3-dihydro-5-(trifluoromethyl)-2H-benzimidazol-2-ylidene]ethylidene]-2-phenyl-1-cyclohexen-1-yl]methylene]-1,2,3,4-tetrahydro-8-phenyl--.

In claim 7, column 131, lines 32-34, "6-(1 1H-benzothiazolo[3,2-b]isoquinolin-6-ylmethylene)-6,11-dihydro" should read --6-(11H-benzothiazolo[3,2-b]isoquinolin-6-ylmethylene)-6,11-dihydro--.

In claim 7, column 131, lines 56-58, "4-[(2,3-dihydro-1H-pyrido[2,1-b]benzothiazol4-yl)methylene]-1,2,3,4-tetrahydropyrido[2,1-b]benzothiazolium" should read --4-[(2,3-dihydro-1H-pyrido[2,1-b]benzothiazol-4-yl)methylene]-1,2,3,4-tetrahydropyrido[2,1-b]benzothiazolium--.

In claim 7, column 132, lines 29-30, "6-[[4-(dimethylamino)phenyl]methylene]-6,1 1-dihydro-" should read --6-[[4-(dimethylamino)phenyl]methylene]-6,11-dihydro- --.

UNITED STATES PATENT AND TRADEMARK OFFICE
CERTIFICATE OF CORRECTION

PATENT NO. : 7,425,221 B2
APPLICATION NO. : 11/223149
DATED : September 16, 2008
INVENTOR(S) : Lagrange It is certified that error appears in the above-identified patent and that said Letters Patent is hereby corrected as shown below:

In claim 7, column 132, lines 38-41, "1-[[3-[2,9-dihydro-9,9-dimethyl-3H-pyrrolo[1,2-a]indol-1-yl)methylene]-2-[[5-(methylthio)-1,3,4-thiadiazol-2 -yl]thio]-1-cyclopenten-1-yl]methylene]-1,2,3,9-tetrahydro-9,9-dimethyl" should read --1-[[3-[(2,9-dihydro-9,9-dimethyl-3H-pyrrolo[1,2-a]indol-1-yl)methylene]-2-[[5-(methylthio)-1,3,4-thiadiazol-2-yl]thio]-1-cyclopenten-1-yl]methylene]-1,2,3,9-tetrahydro-9,9-dimethyl--.

In claim 7, column 133, lines 14-15, "11-[3-(4-dimethylaminophenyl)allyidene]-5-methyl-11H-benzo[4,5]imidazo[2,1-a]isoindol-5-ium" should read --11-[3-(4-dimethylaminophenyl)allylidene]-5-methyl-11H-benzo[4,5]imidazo[2,1-a]isoindol-5-ium--.

In claim 7, column 133, lines 21-24, "l-[[2-chloro-3-[3-[2-phenyl-6-(4-sulfophenyl)thiopyrylium4-yl]-2-propenylidene]-1-cyclohexen-1-yl]methylene]-3-ethyl-l,9-dihydro-2,9,9-trimethyl-7-sulfo" should read --1-[[2-chloro-3-[3-[2-phenyl-6-(4-sulfophenyl)thiopyrylium-4-yl]-2-propenylidene]-1-cyclohexen-1-yl]methylene]-3-ethyl-1,9-dihydro-2,9,9-trimethyl-7-sulfo--.

In claim 7, column 133, lines 39-41, "7,8,9,10-tetrahydro-6-[[1-[3-(trimethylammonio)propyl]4(1H)-quinolinylidene]ethylidene]" should read --7,8,9,10-tetrahydro-6-[[1-[3-(trimethylammonio)propyl]-4(1H)-quinolinylidene]ethylidene]--.

In claim 7, column 133, lines 42-44, "1,2,3,4-tetrahydro4-[[1-(3-(trimethylammonio)propyl]-4(1H)-quinolinylidene]ethylidene]" should read --1,2,3,4-tetrahydro-4-[[1-(3-(trimethylammonio)propyl]-4(1H)-quinolinylidene]ethylidene]--.

In claim 7, column 133, lines 48-50, "8,9, 10,11-tetrahydro11-[[1-(3-iodopropyl)-4(1H)-quinolinylidene]ethylidene]" should read --8,9,10,11-tetrahydro-11-[[1-(3-iodopropyl)-4(1H)-quinolinylidene]ethylidene]--.

In claim 7, column 133, lines 53-55, "3-[3-(trimethylammonio)propyl]-2-[3-[1-[3-(trimethylammonio)propyl]4 (1H)-quinolinylidene]-1-propenyl]" should read --3-[3-(trimethylammonio)propyl]-2-[3-[1-[3-(trimethylammonio)propyl]-4(1H)-quinolinylidene]-1-propenyl]--.

UNITED STATES PATENT AND TRADEMARK OFFICE
CERTIFICATE OF CORRECTION

PATENT NO.       : 7,425,221 B2
APPLICATION NO.  : 11/223149
DATED            : September 16, 2008
INVENTOR(S)      : Lagrange It is certified that error appears in the above-identified patent and that said Letters Patent is hereby corrected as shown below:

In claim 7, column 133, lines 63-64, "8-chloro-7-cyano-1-[(3-ethyl-2-thiazolidiylidene)-ethylidene]-3,4-dihydro-10-methyl" should read --8-chloro-7-cyano-1-[(3-ethyl-2-thiazolidinylidene)ethylidene]-3,4-dihydro-10-methyl--.

In claim 7, column 134, lines 29-31, "7,8-dichloro4-[(5-chloro-1,3-diethyl-1,3-dihydro-2H-benzimidazol-2-ylidene)ethylidene]-5-ethyl-1,2,3,4-tetrahydro" should read --7,8-dichloro-4-[(5-chloro-1,3-diethyl-1,3-dihydro-2H-benzimidazol-2-ylidene)ethylidene]-5-ethyl-1,2,3,4-tetrahydro--.

In claim 7, column 134, lines 35-38, "5-[4-[(acetylamino)sulfonyl]butyl]-4-[(5,6-dichloro-1,3-diethyl-1, 3dihydro-2H-benzimidazol-2-ylidene)ethylidene]-1,2,3,4-tetrahydro" should read --5-[4-[(acetylamino)sulfonyl]butyl]-4-[(5,6-dichloro-1,3-diethyl-1,3-dihydro-2H-benzimidazol-2-ylidene)ethylidene]-1,2,3,4-tetrahydro--.

In claim 7, column 134, lines 49-52, "6,7-dichloro-3-[(5,6dichloro-1,3-diethyl-1,3-dihydro-2H-benzimidazol-2-ylidene)ethylidene]-4-ethyl-2,3-dihydro" should read --6,7-dichloro-3-[(5,6-dichloro-1,3-diethyl-1,3-dihydro-2H-benzimidazol-2-ylidene)ethylidene]-4-ethyl-2,3-dihydro--.

In claim 7, column 134, lines 53-56, "6-cyano-3-[(5-cyano-1,3-diethyl-1,3-dihydro-2H-benzimidazol-2-ylidene)ethylidene]-2,3-dihydro4-[2-[(methylsulfonyl)amino]-2-oxoethyl]" should read --6-cyano-3-[(5-cyano-1,3-diethyl-1,3-dihydro-2H-benzimidazol-2-ylidene)ethylidene]-2,3-dihydro-4-[2-[(methylsulfonyl)amino]-2-oxoethyl]--.

In claim 7, column 135, lines 16-18, "7,8-dichloro-10-ethyl-1-[(3-ethyl-5,6-dimethyl-2(3H benzoxazolylidene)ethylidene]-3,4-dihydro" should read --7,8-dichloro-10-ethyl-1-[(3-ethyl-5,6-dimethyl-2(3H)-benzoxazolylidene)ethylidene]-3,4-dihydro--.

In claim 7, column 135, lines 19-21, "4-[2-(acetyloxy)ethyl]-6-cyano-3-[(3-ethyl-5,6-dimethyl-2(3H benzoxazolylidene)ethylidene]-2,3-dihydro" should read --4-[2-(acetyloxy)ethyl]-6-cyano-3-[(3-ethyl-5,6-dimethyl-2(3H)-

UNITED STATES PATENT AND TRADEMARK OFFICE
CERTIFICATE OF CORRECTION

PATENT NO.       : 7,425,221 B2
APPLICATION NO.  : 11/223149
DATED            : September 16, 2008
INVENTOR(S)      : Lagrange It is certified that error appears in the above-identified patent and that said Letters Patent is hereby corrected as shown below:

benzoxazolylidene)ethylidene]-2,3-dihydro--.

In claim 7, column 135, lines 23-24, "8-chloro-10-ethyl-1-[(3-ethyl-5,6-dimethyl-2(3H benzoxazolylidene)ethylidene]-3,4-dihydro" should read --8-chloro-10-ethyl-1-[(3-ethyl-5,6-dimethyl-2(3H)-benzoxazolylidene)ethylidene]-3,4-dihydro--.

In claim 7, column 135, lines 28-30, "6-(ethoxycarbonyl)-3-[(3-ethyl-5,6-dimethyl-2(3H benzoxazolylidene)ethylidene]-2,3-dihydro-4-methyl" should read --6-(ethoxycarbonyl)-3-[(3-ethyl-5,6-dimethyl-2(3H)-benzoxazolylidene)ethylidene]-2,3-dihydro-4-methyl--.

In claim 7, column 135, lines 35-37, "6,7-dichloro4-ethyl-3-[(3-ethyl-5,6-dimethyl-2(3H benzoxazolylidene)ethylidene]-2,3-dihydro" should read --6,7-dichloro-4-ethyl-3-[(3-ethyl-5,6-dimethyl-2(3H)-benzoxazolylidene)ethylidene]-2,3-dihydro--.

In claim 7, column 135, lines 47-49, "8-(ethoxycarbonyl)-3-[(3-ethyl-5,6-dimethyl-2(3H benzoxazolylidene)ethylidene]-2,3-dihydro-4-methyl" should read --8-(ethoxycarbonyl)-3-[(3-ethyl-5,6-dimethyl-2(3H)-benzoxazolylidene)ethylidene]-2,3-dihydro-4-methyl--.

In claim 7, column 135, lines 50-52, "6-bromo-7-cyano-4-ethyl-3-[(3-ethyl-5,6-dimethyl-2(3H benzoxazolylidene)ethylidene]-2,3-dihydro" should read --6-bromo-7-cyano-4-ethyl-3-[(3-ethyl-5,6-dimethyl-2(3H)-benzoxazolylidene)ethylidene]-2,3-dihydro--.

In claim 7, column 135, lines 59-61, "6-cyano4-ethyl-3-[(3-ethyl-5,6-dimethyl-2(3H)-benzoxazolylidene)ethylidene]-2,3-dihydroiodide" should read --6-cyano-4-ethyl-3-[(3-ethyl-5,6-dimethyl-2(3H)-benzoxazolylidene)ethylidene]-2,3-dihydroiodide--.

In claim 7, column 136, lines 1-3, "3-[(3-ethyl-5-methyl-2(3H)-benzoxazolylidene)ethylidene]-2,3-dihydro4-methyl-6-(1-pyrrolidinylsulfonyl)" should read --3-[(3-ethyl-5-methyl-2(3H)-benzoxazolylidene)ethylidene]-2,3-dihydro-4-methyl-6-(1-pyrrolidinylsulfonyl)--.

In claim 7, column 136, lines 24-26, "6-carboxy-3-[(3-ethyl-2-thiazolidinylideney)-ethylidene]-2,3-dihydro-4-methyl" should read --6-carboxy-3-[(3-ethyl-2-

UNITED STATES PATENT AND TRADEMARK OFFICE
CERTIFICATE OF CORRECTION

PATENT NO. : 7,425,221 B2
APPLICATION NO. : 11/223149
DATED : September 16, 2008
INVENTOR(S) : Lagrange It is certified that error appears in the above-identified patent and that said Letters Patent is hereby corrected as shown below:

thiazolidinylidene)ethylidene]-2,3-dihydro-4-methyl--.

In claim 7, column 136, lines 27-29, "6-cyano4-ethyl-3-[(3-ethyl-2-thiazolidinylidene)-ethylidene]-2,3-dihydro" should read --6-cyano-4-ethyl-3-[(3-ethyl-2-thiazolidinylidene)ethylidene]-2,3-dihydro--.

In claim 7, column 136, lines 45-47, "3-[(3-ethyl-2-thiazolidinylidene)ethylidene]-2,3-dihydro4-methyl-6-(1-pyrrolidinylsulfonyl)" should read --3-[(3-ethyl-2-thiazolidinylidene)ethylidene]-2,3-dihydro-4-methyl-6-(1-pyrrolidinylsulfonyl)--.

In claim 7, column 136, lines 48-50, "7-chloro-6-(ethoxycarbonyl)-3-[(3-ethyl-2-thiazolidinylidene)ethylidene]-2,3-dihydro4-[2-[(methylsulfonyl)amino]-2-oxoethyl]-" should read --7-chloro-6-(ethoxycarbonyl)-3-[(3-ethyl-2-thiazolidinylidene)ethylidene]-2,3-dihydro-4-[2-[(methylsulfonyl)amino]-2-oxoethyl]--.

In claim 7, column 137, lines 7-9, "7chloro-8-cyano-5-ethyl-4-[(3-ethyl-2-thiazolidinylidene)ethylidene]-1,2,3,4-tetrahydro" should read --7-chloro-8-cyano-5-ethyl-4-[(3-ethyl-2-thiazolidinylidene)ethylidene]-1,2,3,4-tetrahydro--.

In claim 7, column 137, lines 22-24, "4[-4-[(acetylamino)sulfonyl]butyl]-6,7-dichloro-3-[(3-ethyl-2-selenazolidinylidene)ethylidene]-2,3-dihydro" should read --4-[4-[(acetylamino)sulfonyl]butyl]-6,7-dichloro-3-[(3-ethyl-2-selenazolidinylidene)ethylidene]-2,3-dihydro--.

In claim 7, column 137, lines 40-43, "7-(acetylamino)-3-[(5,6-dichloro-1,3-diethyl-1,3-dihydro-2H-benzimidazol-2-ylidene)ethylidene]4-ethyl-2,3-dihydro" should read --7-(acetylamino)-3-[(5,6-dichloro-1,3-diethyl-1,3-dihydro-2H-benzimidazol-2-ylidene)ethylidene]-4-ethyl-2,3-dihydro--.

In claim 7, column 137, lines 47-49, "7-bromo4-[(5-chloro-1,3-diethyl-1,3-dihydro-2H-benzimidazol-2-ylidene)ethylidene]-5-ethyl-1,2,3,4-tetrahydro" should read --7-bromo-4-[(5-chloro-1,3-diethyl-1,3-dihydro-2H-benzimidazol-2-ylidene)ethylidene]-5-ethyl-1,2,3,4-tetrahydro--.

In claim 7, column 138, lines 1-3, "7chloro-4-ethyl-3-[(3-ethyl-5-methyl-2(3H)-benzoxazolylidene)ethylidene]-2,3-dihydro" should read --7-chloro-4-ethyl-3-[(3-ethyl-

UNITED STATES PATENT AND TRADEMARK OFFICE
CERTIFICATE OF CORRECTION

PATENT NO. : 7,425,221 B2
APPLICATION NO. : 11/223149
DATED : September 16, 2008
INVENTOR(S) : Lagrange It is certified that error appears in the above-identified patent and that said Letters Patent is hereby corrected as shown below:

5-methyl-2(3H)-benzoxazolylidene)ethylidene]-2,3-dihydro--.
In claim 7, column 138, lines 10-12, "6-carboxy-7chloro-3-[(3-ethyl-5,6-dimethyl-2(3H)-benzoxazolylidene)ethylidene]-2,3-dihydro-4-methyl" should read --6-carboxy-7-chloro-3-[(3-ethyl-5,6-dimethyl-2(3H)-benzoxazolylidene)ethylidene]-2,3-dihydro-4-methyl--.

In claim 7, column 138, lines 19-21, "6-chloro-7-cyano4-ethyl-3-[(3-ethyl-2-thiazolidinylidene)ethylidene]-2,3-dihydro" should read --6-chloro-7-cyano-4-ethyl-3-[(3-ethyl-2-thiazolidinylidene)ethylidene]-2,3-dihydro--.

In claim 7, column 138, lines 23-25, "7-bromo-6-(ethoxycarbonyl)-3-[(3-ethyl-2-thiazolidinylidene)ethylidene]-2,3-dihydro4-[3-(sulfooxy)propyl]" should read --7-bromo-6-(ethoxycarbonyl)-3-[(3-ethyl-2-thiazolidinylidene)ethylidene]-2,3-dihydro-4-[3-(sulfooxy)propyl]--.

In claim 7, column 138, lines 41-43, "8-carboxy-3-[(3-ethyl-2-thiazolidinylideney)-ethylidene]-2,3-dihydro-4-methyl" should read --8-carboxy-3-[(3-ethyl-2-thiazolidinylidene)ethylidene]-2,3-dihydro-4-methyl--.

In claim 7, column 138, lines 44-46, "6,7-dichloro4-ethyl-3-[(3-ethyl-2-thiazolidinylidene)ethylidene]-2,3-dihydro" should read --6,7-dichloro-4-ethyl-3-[(3-ethyl-2-thiazolidinylidene)ethylidene]-2,3-dihydro--.

In claim 13, column 139, line 9, "naphthoquinonedyes," should read --naphthoquinone dyes,--.

In claim 33, column 140, line 24, "fivers" should read --fibers--.

In claim 33, column 140, line 22, "develp" should read --develop--.

In claim 36, column 142, line 40, "a nd" should read --and--.

UNITED STATES PATENT AND TRADEMARK OFFICE
CERTIFICATE OF CORRECTION

PATENT NO. : 7,425,221 B2
APPLICATION NO. : 11/223149
DATED : September 16, 2008
INVENTOR(S) : Lagrange It is certified that error appears in the above-identified patent and that said Letters Patent is hereby corrected as shown below:

In claim 36, column 142, line 45, "chsoen" should read --chosen--.

In claim 37, column 144, line 14, "a nd" should read --and--.

Signed and Sealed this

Seventh Day of April, 2009

JOHN DOLL
*Acting Director of the United States Patent and Trademark Office*